United States Patent
Huang et al.

(10) Patent No.: US 12,171,729 B2
(45) Date of Patent: Dec. 24, 2024

(54) FORMULATIONS OF TERAMEPROCOL AND TEMOZOLOMIDE AND THEIR USE IN STIMULATION OF HUMORAL IMMUNITY IN TUMORS

(71) Applicants: The Johns Hopkins University, Baltimore, MD (US); Academia Sinica, Taipei (TW); National Yang Ming Chiao Tung University, Hsinchu (TW)

(72) Inventors: Ru Chih C. Huang, Baltimore, MD (US); Jong Ho Chun, Baltimore, MD (US); Yu-Ling Lin, Taipei (TW); Yu-Chuan Liang, Taipei (TW); Kuang-Wen Liao, Hsinchu (TW); Tiffany Jackson, Baltimore, MD (US); David Mold, Baltimore, MD (US); Chien-Hsien Lai, Baltimore, MD (US)

(73) Assignees: The Johns Hopkins University, Baltimore, MD (US); Academia Sinica, Taipei (TW); National Yang Ming Chiao Tung University, Hsinchu (TW)

( * ) Notice: Subject to any disclaimer, the term of this patent is extended or adjusted under 35 U.S.C. 154(b) by 0 days.

(21) Appl. No.: 17/779,048

(22) PCT Filed: Nov. 25, 2020

(86) PCT No.: PCT/US2020/062288
§ 371 (c)(1),
(2) Date: May 23, 2022

(87) PCT Pub. No.: WO2021/108601
PCT Pub. Date: Jun. 3, 2021

(65) Prior Publication Data
US 2022/0409552 A1 Dec. 29, 2022

Related U.S. Application Data

(60) Provisional application No. 63/081,098, filed on Sep. 21, 2020, provisional application No. 62/939,823, filed on Nov. 25, 2019.

(51) Int. Cl.
*A61K 31/05* (2006.01)
*A61K 9/00* (2006.01)
(Continued)

(52) U.S. Cl.
CPC ............ *A61K 31/05* (2013.01); *A61K 9/0053* (2013.01); *A61K 31/09* (2013.01); *A61K 31/444* (2013.01);
(Continued)

(58) Field of Classification Search
CPC ...... A61K 31/05; A61K 31/09; A61K 31/444; A61K 31/495; A61P 35/00
See application file for complete search history.

(56) References Cited

U.S. PATENT DOCUMENTS 5,939,098 A * 8/1999 Reidenberg .......... A61K 31/415
514/183
6,346,524 B1  2/2002 Ragab
(Continued)

FOREIGN PATENT DOCUMENTS

WO   WO-2007101111 A2 *  9/2007  ............. A61K 31/03

OTHER PUBLICATIONS

Reagan-Shaw (FASEBJ vol. 22 pp. 659-661 published 2007) (Year: 2007).*
(Continued)

*Primary Examiner* — Theodore R. Howell
*Assistant Examiner* — George W Kosturko
(74) *Attorney, Agent, or Firm* — Casimir Jones, S.C.; David A. Fazzolare

(57) ABSTRACT

The present invention provides novel pharmaceutical formulations comprising derivatives of NDGA, including $M_4N$ (tetra-0-methyl nordihydroguaiaretic acid) and temozolomide and their use in the inhibition and treatment of neo-
(Continued)

plastic diseases, including glioblastoma multiforme, lung and other cancers.

21 Claims, 46 Drawing Sheets

(51) Int. Cl.
| | |
|---|---|
| A61K 31/09 | (2006.01) |
| A61K 31/444 | (2006.01) |
| A61K 31/495 | (2006.01) |
| A61K 47/14 | (2017.01) |
| A61K 47/22 | (2006.01) |
| A61P 35/00 | (2006.01) |

(52) U.S. Cl.
CPC ............ *A61K 31/495* (2013.01); *A61K 47/14* (2013.01); *A61K 47/22* (2013.01); *A61P 35/00* (2018.01)

(56) References Cited

U.S. PATENT DOCUMENTS

| | | | |
|---|---|---|---|
| 7,741,357 | B1 | 6/2010 | Huang et al. |
| 7,871,642 | B2 | 1/2011 | Supersaxo et al. |
| 8,318,815 | B2 | 11/2012 | Huang et al. |
| 8,440,648 | B2 | 5/2013 | Frazer et al. |
| 9,067,875 | B2 | 6/2015 | Chen et al. |
| 9,084,779 | B2 | 7/2015 | Huang et al. |
| 9,539,299 | B2 | 1/2017 | Sugiyama et al. |
| 9,877,978 | B2 | 1/2018 | Huang et al. |
| RE46,907 | E | 6/2018 | Huang et al. |
| 2002/0197266 | A1 | 12/2002 | Debinski |
| 2011/0014192 | A1 | 1/2011 | Huang et al. |
| 2011/0091375 | A1 | 4/2011 | Weichselbaum et al. |
| 2015/0018302 | A1 | 1/2015 | Huang et al. |
| 2018/0078546 | A1 | 3/2018 | Ugwu et al. |
| 2018/0079754 | A1 | 3/2018 | Emrick et al. |
| 2019/0111040 | A1 | 4/2019 | Huang et al. |

OTHER PUBLICATIONS

Grossman (NeuroOncology vol. 14 pp. 511-517 published 2012). (Year: 2012).*
Moody (Experimental Lung Research vol. 24 pp. 617-628 published 1998) (Year: 1998).*
International Search Report and Written Opinion for PCT/US20/62288. Mailed Mar. 17, 2021. 27 pages.
Carvalho et al., KRAS Oncogenic Signaling Extends beyond Cancer Cells to Orchestrate the Microenvironment. Cancer Res. Jan. 1, 2018;78(1):7-14.
Casbon et al., Invasive breast cancer reprograms early myeloid differentiation in the bone marrow to generate immunosuppressive neutrophils. PNAS, 2015. 112(6). E566-E575.
Galan-Cobo et al., LKB1 and KEAP1/NRF2 Pathways Cooperatively Promote Metabolic Reprogramming with Enhanced Glutamine Dependence in KRAS-Mutant Lung Adenocarcinoma. Cancer Res. Jul. 1, 2019;79(13):3251-3267.
Hanahan et al., Hallmarks of cancer: the next generation. Cell. Mar. 4, 2011;144(5):646-74.
Johnson et al., Somatic activation of the K-ras oncogene causes early onset lung cancer in mice. Nature. Apr. 26, 2001;410(6832):1111-6.
Kull et al., Mixtures of quaternary ammonium compounds and long-chain fatty acids as antifungal agents. Appl Microbiol. Nov. 1961;9(6):538-41.
Pinto et al., KRAS-Driven Lung Adenocarcinoma and B Cell Infiltration: Novel Insights for Immunotherapy. Cancers (Basel). Aug. 9, 2019;11(8):1145. 1-15.
Tao et al., Oncogenic KRAS confers chemoresistance by upregulating NRF2. Cancer Res. Dec. 15, 2014;74(24):7430-41.
Wuts. Protective Groups in Organic Synthesis. John Wiley & Sons Inc. 2014. TOC only. 9 pages.
Bindea et al., Spatiotemporal dynamics of intratumoral immune cells reveal the immune landscape in human cancer. Immunity. Oct. 17, 2013;39(4):782-95.
Carmi et al., Allogeneic IgG combined with dendritic cell stimuli induce antitumour T-cell immunity. Nature. May 7, 2015;521(7550):99-104.
Castro-Gamero et al., Tetra-O-methyl nordihydroguaiaretic acid, an inhibitor of Sp1-mediated survivin transcription, induces apoptosis and acts synergistically with chemo-radiotherapy in glioblastoma cells. Invest New Drugs. Aug. 2013;31(4):858-70.
Chang et al., Reversal of multidrug resistance by two nordihydroguaiaretic acid derivatives, M4N and maltose-M3N, and their use in combination with doxorubicin or paclitaxel. Cancer Chemother Pharmacol. Nov. 2006;58(5):640-53.
Chang et al., Tetra-O-methyl nordihydroguaiaretic acid induces growth arrest and cellular apoptosis by inhibiting Cdc2 and survivin expression. Proc Natl Acad Sci U S A. Sep. 7, 2004;101(36):13239-44.
Chen et al., Antiviral activities of methylated nordihydroguaiaretic acids. 2. Targeting herpes simplex virus replication by the mutation insensitive transcription inhibitor tetra-O-methyl-NDGA. J Med Chem. Jul. 30, 1998;41(16):3001-7.
Coquet et al., IL-21 is produced by NKT cells and modulates NKT cell activation and cytokine production. J Immunol. Mar. 1, 2007;178(5):2827-34.
Craigo et al., Inhibition of human papillomavirus type 16 gene expression by nordihydroguaiaretic acid plant lignan derivatives. Antiviral Res. Jul. 2000;47(1):19-28.
De Felice et al., New Approaches in Glioblastoma Multiforme: The Potential Role of Immune- check Point Inhibitors. Curr Cancer Drug Targets. 2017;17(3):282-289.
Duan et al., AID expression increased by TNF-α is associated with class switch recombination of Igα gene in cancers. Cell Mol Immunol. Jul. 2016;13(4):484-91.
Fadul et al., Immune modulation effects of concomitant temozolomide and radiation therapy on peripheral blood mononuclear cells in patients with glioblastoma multiforme. Neuro Oncol. Apr. 2011;13(4):393-400.
Faje et al., High-dose glucocorticoids for the treatment of ipilimumab-induced hypophysitis is associated with reduced survival in patients with melanoma. Cancer. Sep. 15, 2018;124(18):3706-3714.
Gnabre et al., Inhibition of human immunodeficiency virus type 1 transcription and replication by DNA sequence-selective plant lignans. Proc Natl Acad Sci U S A. Nov. 21, 1995;92(24):11239-43.
Heller et al., Tetra-O-methyl nordihydroguaiaretic acid induces G2 arrest in mammalian cells and exhibits tumoricidal activity in vivo. Cancer Res. Jul. 15, 2001;61(14):5499-504.
Hwu et al., Antiviral activities of methylated nordihydroguaiaretic acids. 1. Synthesis, structure identification, and inhibition of tat-regulated HIV transactivation. J Med Chem. Jul. 30, 1998;41(16):2994-3000.
Karnell et al., The Interplay of IL-21 and BAFF in the Formation and Maintenance of Human B Cell Memory. Front Immunol. Jan. 24, 2012;3:2. 1-9.
Kim et al., Macrophage-derived BAFF induces AID expression through the p38MAPK/CREB and JNK/AP-1 pathways. J Leukoc Biol. Mar. 2011;89(3):393-8.
Kimura et al., Tetra-O-Methyl Nordihydroguaiaretic Acid Broadly Suppresses Cancer Metabolism and Synergistically Induces Strong Anticancer Activity in Combination with Etoposide, Rapamycin and UCN-01. PLoS One. Feb. 17, 2016;11(2):e0148685. 1-28.
Lang. The Influence of Invariant Natural Killer T Cells on Humoral Immunity to T-Dependent and -Independent Antigens. Front Immunol. Feb. 22, 2018;9:305. 1-7.
Lee et al., Cell-surface major vault protein promotes cancer progression through harboring mesenchymal and intermediate circulating tumor cells in hepatocellular carcinomas. Sci Rep. Oct. 16, 2017;7(1):13201. 1-15.
Li et al., Serum IL-21 levels decrease with glucocorticoid treatment in myasthenia gravis Serum IL-21 levels decrease with glucocorticoid treatment in myasthenia gravis. Neurol Sci. Jan. 2014;35(1):29-34.

(56) References Cited

OTHER PUBLICATIONS

Lim et al., Current state of immunotherapy for glioblastoma. Nat Rev Clin Oncol. Jul. 2018;15(7):422-442.
Milicevic et al., T cells are required for the peripheral phase of B-cell maturation. Immunology. Nov. 2005;116(3):308-17.
Navarro et al., Alteration of major vault protein in human glioblastoma and its relation with EGFR and PTEN status. Neuroscience. Jun. 25, 2015;297:243-51.
Okazaki et al., Histone chaperone Spt6 is required for class switch recombination but not somatic hypermutation. Proc Natl Acad Sci U S A. May 10, 2011;108(19):7920-5.
Ouadani et al., Activation induced cytidine deaminase mutant (AID-His130Pro) from Hyper IgM 2 patient retained mutagenic activity on SHM artificial substrate. Mol Immunol. Nov. 2016;79:77-82.
Park et al., Systemic treatment with tetra-O-methyl nordihydroguaiaretic acid suppresses the growth of human xenograft tumors. Clin Cancer Res. Jun. 15, 2005;11(12):4601-9.
Parrish-Novak et al., Interleukin 21 and its receptor are involved in NK cell expansion and regulation of lymphocyte function. Nature. Nov. 2, 2000;408(6808):57-63.
Pellicci et al., A natural killer T (NKT) cell developmental pathway iInvolving a thymus-dependent NK1.1(−)CD4(+) CD1d-dependent precursor stage. J Exp Med. Apr. 1, 2002;195(7):835-44.
Puga et al., B cell-helper neutrophils stimulate the diversification and production of immunoglobulin in the marginal zone of the spleen. Nat Immunol. Dec. 25, 2011;13(2):170-80.
Schalper et al., Neoadjuvant nivolumab modifies the tumor immune microenvironment in resectable glioblastoma. Nat Med. Mar. 2019;25(3):470-476.
Simard et al., Analysis of the role of IL-21 in development of murine B cell progenitors in the bone marrow. J Immunol. May 1, 2011;186(9):5244-53.
Thompson et al., The Inflammatory Cytokine IL-21 is Expressed by Splenic Neutrophils in Response to Transplantation of Allogeneic Cells. SOJ Immunol. 2016;4(1):1-9.
Wang et al., Amplification of IL-21 signalling pathway through Bruton's tyrosine kinase in human B cell activation. Rheumatology (Oxford). Aug. 2015;54(8):1488-97.
Wang et al., Tumor Evolution of Glioma-Intrinsic Gene Expression Subtypes Associates with Immunological Changes in the Microenvironment. Cancer Cell. Jul. 10, 2017;32(1):42-56.e6.
Wu et al., The Biological Effects of IL-21 Signaling on B-Cell-Mediated Responses in Organ Transplantation. Front Immunol . Aug. 23, 2016;7:319. 1-10.
Hu et al., Acidosis enchances the self-renewal and mitochondrial respiration of stem cell-like glioma cells through CYP24A1-ediated reduction of vitamin D. 2018 Sep. 29; 14 pages.

* cited by examiner

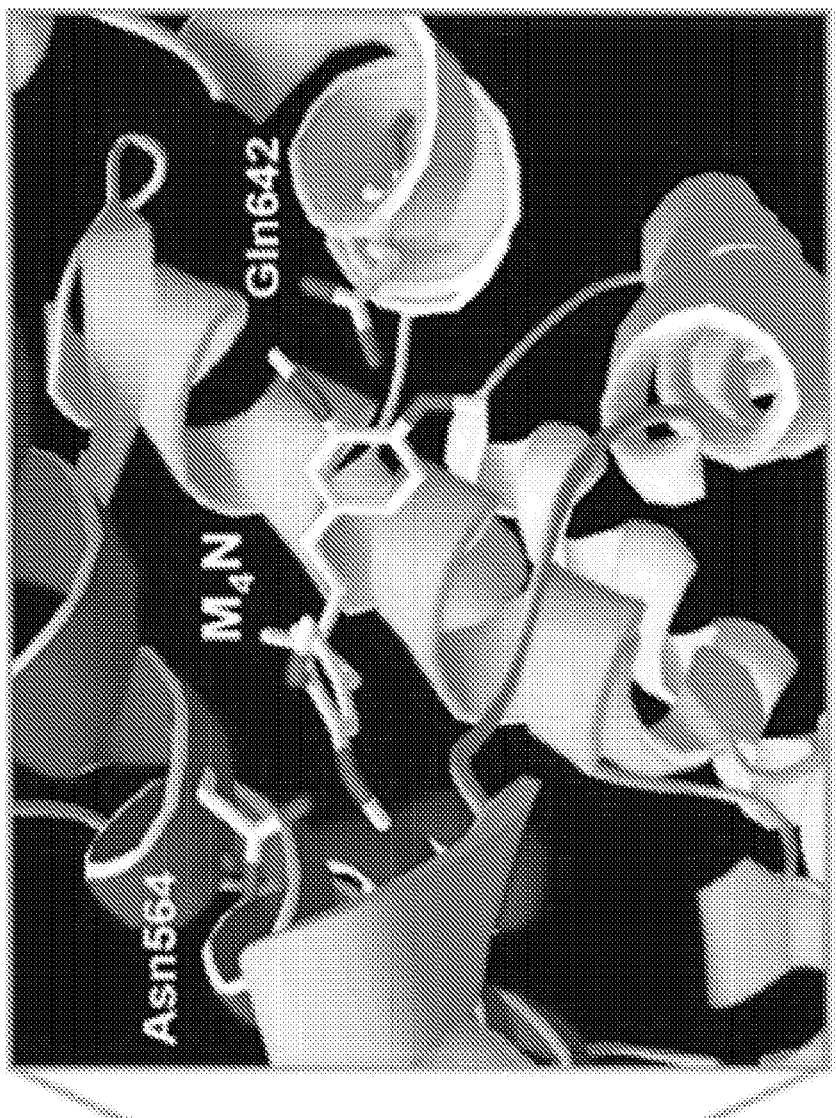
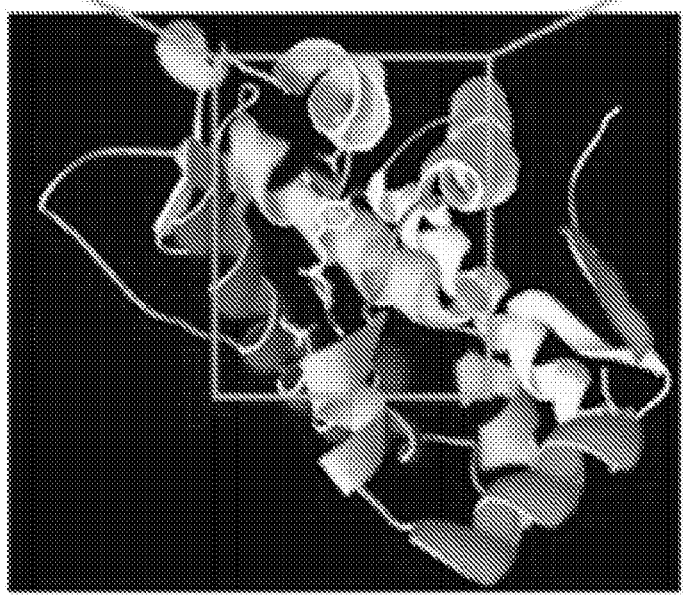
Fig. 1K

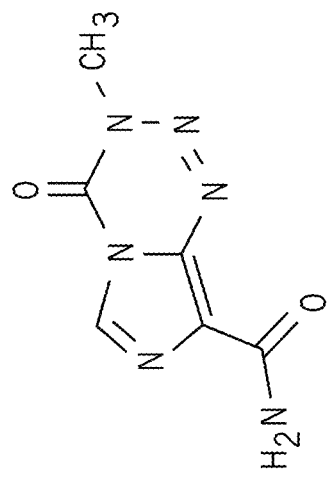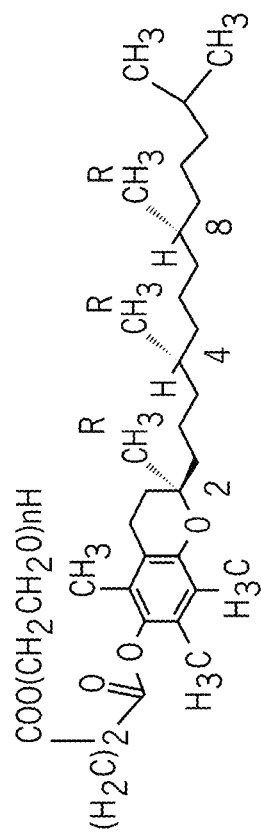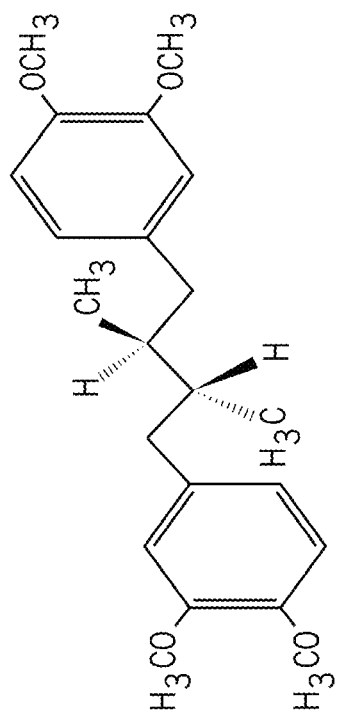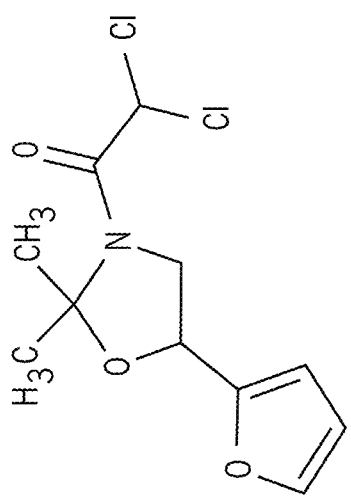
Fig. 2

|  | | | Fold-Change | |
|---|---|---|---|---|
| Biochemical Name (Sub Pathways in Bold Type) | EM + TMZ-1/2 | EM + MT 1/2 | EM + TMZ-1/2 | EM + MT-1/2 |
|  | (A) | (B) | (A/B) | (B/A) |
| Gbr/Ser/Thr: | | | | |
| betaine-aldehyde | 1.4350 | 2.6388 | | 1.83 |
| serine | 0.8329 | 0.6997 | 1.20 | |
| N-acetylserine | 1.1027 | 0.7948 | 1.38 | |
| theronine | 0.7892 | 0.6127 | 1.24 | |
| N-acetyltheronine | 0.7582 | 0.6631 | 1.14 | |
| Alanine/Aspertate | | | | |
| alanine | 0.8237 | 0.7092 | 1.16 | |
| N-acetylaspartate (NAA) | 0.6991 | 1.6428 | | 2.50 |
| Glutamate | | | | |
| 4-hydroxyglutamate | 0.8710 | 0.6410 | 1.35 | |
| gamma-carboxyglutamate | 0.7632 | 0.6759 | 1.13 | |
| glutamate, gamma methyl-ester | 0.7379 | 0.6324 | 1.17 | |
| pyroglutamine* | 0.6887 | 0.5234 | 1.31 | |
| N-acetyl-ap-glu (NAAG) | 1.1888 | 1.0309 | 1.15 | |
| beta-citylglutamate | 0.8310 | 0.5846 | 1.42 | |
| gamma-aminobutyrate | 0.7555 | 0.5653 | 1.36 | |
| Histidine | | | | |
| histidine | 0.9038 | 0.6639 | 1.36 | |
| 1-methylhistidine | 0.3390 | 0.2325 | 1.45 | |
| 2-methylhistidine | 0.5237 | 0.5232 | 1.00 | |
| imidzaola lactate | 0.9425 | 0.6844 | 1.37 | |
| anserine | 0.8537 | 0.7330 | 1.16 | |
| histamine | 3.5327 | 0.5812 | 1.36 | |
| 1-methylhistamine | 1.3666 | 0.8309 | 1.64 | |
| 1-methyl-4-imidazoleacatate | 2.1349 | 1.2379 | 1.72 | |
| N-acetylhistamine | 1.4159 | 0.9343 | 1.51 | |
| Lysine | | | | |
| N6-acetyllysine | 0.8191 | 0.7310 | 1.12 | |
| 5-hydroxylysine | 0.9335 | 0.8586 | 1.09 | |
| fructoselysine | 0.4263 | 0.3975 | 1.07 | |
| 6-oxopiperidine-2-carboxylate | 0.6335 | 0.3323 | 1.90 | |
| 5-aminovalerate | 0.8826 | 0.7667 | 1.15 | |
| N,N,N-trimethyl-5-aminovalerate | 0.7375 | 0.5832 | 1.26 | |

Fig. 4A

| Biochemical Name (Sub Pathways in Bold Type) | EM + TMZ- 1/2 (A) | EM + MT 1/2 (B) | Fold-Change EM + TMZ- 1/2 (A/B) | Fold-Change EM + MT- 1/2 (B/A) |
|---|---|---|---|---|
| Phenylalanine | | | | |
| phenylalanine | 0.8093 | 0.6861 | 1.18 | |
| N-acetylphenylalanine | 0.6062 | 0.5476 | 1.11 | |
| 1-carboxyethylphenylalanine | 0.2713 | 0.1366 | 1.98 | |
| phenyllactate (PLA) | 0.8018 | 0.7987 | 1.00 | |
| Tyrosine | | | | |
| tyrosine | 0.7832 | 0.7092 | 1.19 | |
| 1-carboxyethyltyrosine | 0.4297 | 0.2768 | 1.55 | |
| phenol sulfate | 0.6596 | 0.3567 | 1.84 | |
| 3-methoxytyrosine | 0.6494 | 0.5501 | 1.18 | |
| o-Tyrosine | 0.8035 | 0.5742 | 1.39 | |
| O-methyltyrosine | 0.9549 | 0.8243 | 1.16 | |
| Tryptophan | | | | |
| tryptophan | 0.7211 | 0.5368 | 1.34 | |
| N-acetyltryptophan | 0.6150 | 0.5232 | 1.17 | |
| c-glycosyltryptophan | 0.6959 | 0.5702 | 1.22 | |
| kynurenate | 0.5621 | 0.4617 | 1.28 | |
| N-formylapthtrplitc acid | 0.8233 | 0.7262 | 1.13 | |
| 5-hydroxyindoleacetate | 2.6173 | 1.7424 | 1.50 | |
| indolelactate | 0.7122 | 0.6934 | 1.03 | |
| indolepropionate | 0.7066 | 0.5221 | 1.35 | |
| 3-indoxyl sulfate | 0.9497 | 0.5794 | 1.63 | |
| Glutathione | | | | |
| glutathione, reduced | 2.9119 | 1.4382 | 2.02 | |
| glutathione, oxidized | 1.7158 | 1.0585 | 1.62 | |
| 2-hydroxybutyrate 2-hydroxyisobutyrate | 0.4417 | 0.2531 | 1.74 | |
| gamma-glutamylcine | 0.5433 | 0.4621 | 1.18 | |
| gamma-glutamylhistidine | 0.3947 | 0.2301 | 1.71 | |
| gamma-glutamylisoleucine | 0.3818 | 0.1974 | 1.93 | |
| gamma-glutamylleucine | 0.4663 | 0.2826 | 1.65 | |
| gamma-glutamyl-alpha-lysine | 0.5903 | 0.3987 | 1.48 | |
| gamma-glutamylmethionine | 0.9246 | 0.5031 | 1.83 | |
| gamma-glutamylphenylalanine | 0.5198 | 0.3225 | 1.61 | |
| gamma-glutamyltheromine | 0.5156 | 0.3493 | 1.47 | |

Fig. 4A (cont.)

| Biochemical Name (Sub Pathways in Bold Type) | EM + TMZ-1/2 (A) | EM + MT 1/2 (B) | Fold-Change EM + TMZ-1/2 (A/B) | Fold-Change EM + MT-1/2 (B/A) |
|---|---|---|---|---|
| Leuc / Isoleud / Valine | | | | |
| leucine | 0.7897 | 0.6651 | 1.19 | |
| 1-carboxyechylleucine | 0.2817 | 0.1624 | 1.73 | |
| 4-metyl-2-oxopentanoate | 0.7450 | 0.6397 | 1.16 | |
| beta-hydroxyisovalerylcarnitine | 0.7581 | 0.5902 | 1.28 | |
| ethylmalonate | 0.4706 | 0.3357 | 1.40 | |
| methylsuccinate | 0.6137 | 0.9908 | | 1.52 |
| valine | 0.7635 | 0.6007 | 1.27 | |
| N-acetylaniline | 0.5494 | 0.4196 | 1.30 | |
| 1-carboxyethylvaline | 0.2786 | 0.1586 | 1.75 | |
| 3-methyl-2-oxobutyrate | 0.9240 | 0.7242 | 1.27 | |
| S-adenosylhomocysteine | 0.3186 | 0.1848 | 1.72 | |
| cystathionine | 0.6137 | 0.3666 | 1.67 | |
| cysteine | 1.2608 | 0.6830 | 1.84 | |
| S-methylcysteine | 0.6378 | 0.5115 | 1.25 | |
| S-methylcysteine sulfoxide | 0.3103 | 0.2157 | 1.43 | |
| cysteine s-sulfate | 0.7277 | 0.6243 | 1.16 | |
| cystine | 0.4212 | 0.3096 | 1.36 | |
| cysteine sulfinic acid | 0.7579 | 0.5992 | 1.26 | |
| hypotaurine | 0.9714 | 0.8433 | 1.15 | |
| Urea Cycle-Arg / Pro | | | | |
| arginine | 0.9154 | 0.7819 | 1.17 | |
| argininosuccinate | 0.3471 | 0.2287 | 1.52 | |
| citrulline | 0.6143 | 0.4959 | 1.24 | |
| homocitrulline | 0.4392 | 0.2986 | 1.47 | |
| proline | 0.7293 | 0.6238 | 1.17 | |
| dimethylarginine (SDMA- ADMA) | 0.7503 | 0.6769 | 1.11 | |
| N-methylproline | 0.8026 | 0.6872 | 1.17 | |
| N-monomethylarginine | 0.8861 | 0.7519 | 1.18 | |
| N-acetyl-isonutrpine | 1.2001 | 0.7712 | 1.56 | |
| spermidine | 1.3221 | 0.7648 | 1.72 | |
| N(1)-acetyspermidine | 0.9386 | 0.5947 | 1.57 | |
| N(S)-acetyspermidine | 0.5813 | 0.2774 | 2.09 | |
| spermine | 1.4814 | 0.7266 | 2.05 | |

Fig. 4B

|  | | Fold-Change | |
|---|---|---|---|---|
| Biochemical Name (Sub Pathways in Bold Type) | EM + TMZ- 1/2 | EM + MT 1/2 | EM + TMZ- 1/2 | EM + MT- 1/2 |
|  | (A) | (B) | (A/B) | (B/A) |
| Dipeptide | | | | |
| alanylleucine | 0.8396 | 0.3091 | 2.71 | |
| glycylleucine | 1.0075 | 0.5727 | 1.75 | |
| glycylalanine | 1.5621 | 0.8388 | 1.86 | |
| histidylalanine | 1.5389 | 0.7754 | 1.98 | |
| leucylglycine | 1.7561 | 1.1642 | 1.50 | |
| phenylalanylalanine | 1.986 | 0.7283 | 2.45 | |
| phenylalanylglycine | 0.9430 | 0.5007 | 1.88 | |
| N-acetylaspartate (NAA) | 1.0718 | 0.6510 | 1.64 | |
| 4-hydroxyglutamate | 0.9013 | 0.2616 | 3.49 | |
| legacyglutamine* | 1.7695 | 0.6635 | 2.67 | |
| Glycolysis | | | | |
| pyruvate | 1.2342 | 1.0076 | 1.20 | |
| lactate | 0.3394 | 0.2019 | 1.68 | |
| N-acetylglucosamine 6-phosphate | 0.6226 | 0.4160 | 1.49 | |
| N-acetylglucosamine 1-phosphate | 0.4200 | 0.2060 | 2.04 | |
| anthronate* | 0.7184 | 0.5766 | 1.24 | |
| N-acetylglucosamine N-acetylgalactosamine | 0.8427 | 0.8153 | 1.01 | |
| N-glycolyneuraminate | 0.8520 | 0.9478 | | 1.11 |
| Adv. Glyca End-product | | | | |
| N6-carboxymethyllysine | 0.6226 | 0.4160 | 1.39 | |
| TCA-Cycle | | | | |
| citrate | 1.2534 | 1.1555 | 1.08 | |
| alpha-ketoglutarate | 0.8218 | 0.6694 | 1.22 | |
| succinylcarnitine (CD4-DC) | 0.5608 | 0.3537 | 1.55 | |
| succinate | 0.7248 | 0.7146 | 1.04 | |
| fumarate | 0.5507 | 0.4316 | 1.27 | |
| malate | 0.5855 | 0.4827 | 1.21 | |
| itaconate | 1.9525 | 3.6971 | | 1.99 |
| Fatty Acid Synthesis | | | | |
| malonylcarnitine | 0.9689 | 0.6845 | 1.10 | |
| Fatty Acid Metabolism | | | | |
| acetylcarnitine (C2) | 0.8615 | 0.5295 | 1.62 | |
| hexanoylcarnitine (C6) | 1.1042 | 0.7093 | 1.55 | |

Fig. 4B (cont.)

|  | | | Fold-Change | |
|---|---|---|---|---|
| Biochemical Name (Sub Pathways in Bold Type) | EM + TMZ-1/2 | EM + MT-1/2 | EM + TMZ-1/2 | EM + MT-1/2 |
| | (A) | (B) | (A/B) | (B/A) |
| Fatty Acid Metabolism | | | | |
| octanoylcarnitine (C8) | 1.3281 | 0.6971 | 1.90 | |
| decanoylcarnitine (C10) | 0.9581 | 0.6605 | 1.45 | |
| lauroylcarnitine (C12) | 1.1015 | 0.5750 | 1.91 | |
| stearoylcarnitine (C18) | 1.1045 | 0.7539 | 1.46 | |
| arachidonoylcarnitine (C20)* | 1.3888 | 0.9697 | .43 | |
| behenoylcarnitine (22)* | 1.0225 | 0.6536 | 1.56 | |
| lignoceroylcarnitine (24)* | 0.9422 | 0.5897 | 1.59 | |
| butenoylcarnitine (C4:1) | 0.6382 | 0.3904 | 1.61 | |
| (R) 3-hydroxybutyrylcarnitine | 1.9295 | 0.9893 | 1.95 | |
| (S) 3-hydroxybutyrylcarnitine | 0.8169 | 0.5259 | 1.55 | |
| 3-hydroxyhexanoylcarnitine (1) | 0.7351 | 0.5391 | 1.36 | |
| 3-hydroxyhexanoylcarnitine (2) | 0.5939 | 0.3732 | 1.59 | |
| 3-hydroxydecanoylcarnitine | 0.7097 | 0.3080 | 2.30 | |
| 3-hydroxypalmitoylcarnitine | 0.5768 | 0.2926 | 1.97 | |
| 1-stearoyl-2-oleoyl-GPI (18:0/18:1)* | 1.0351 | 0.5017 | 2.62 | |
| 1-(1-eny-stearoyl)-2-oleoyl-GPE (P-18:0/18:2)* | 1.7950 | 0.7516 | 2.39 | |
| 1-(1-eny-stearoyl)-2-linoleoyl-GPE-(P-18:0/18:2)* | 1.5739 | 0.8216 | 1.91 | |
| Purine Metabolism | | | | |
| inosine | 0.7199 | 0.1499 | 4.80 | |
| hypoxanthine | 0.7135 | 0.1944 | 3.67 | |
| xanthine | 0.7178 | 0.3177 | 2.25 | |
| 2'-deoxyinosine | 0.3537 | 0.1174 | 3.01 | |
| adenosine 3',5' diphosphate | 1.0865 | 0.4207 | 2.58 | |
| N6-methyladenosine | 0.8023 | 0.5885 | 1.36 | |
| guanosine | 0.7627 | 0.2133 | 3.57 | |
| 2'deoxyguanosine | 0.4079 | 0.1613 | .52 | |
| uridine-2',3'-cyclic-monophasphate | 2.5325 | 1.5980 | 1.58 | |
| cytidine 2',3'-cylic-monophasphate | 2.0211 | 1.4509 | 1.39 | |

Fig. 4C

| Biochemical Name (Sub Pathways in Bold Type) | EM + TMZ- 1/2 | EM + MT 1/2 | Fold-Change EM + TMZ- 1/2 | Fold-Change EM + MT- 1/2 |
|---|---|---|---|---|
| | (A) | (B) | (A/B) | (B/A) |
| Ascorbate and Aldarate | | | | |
| ascorbate (Vitamin C) | 3.0294 | 0.2826 | 10.71 | |
| dehydroascorbate | 0.5292 | 0.3055 | 1.73 | |
| 2-O-methylascorbic acid | 0.9124 | 0.7802 | 1.16 | |
| threonate | 0.4923 | 0.5997 | | 1.21 |
| oxalate (ethanedioate) | 0.9927 | 1.0039 | | 1.01 |
| gulonate* | 0.5429 | 0.8159 | | 1.50 |
| Tocopherol-Metabolism | | | | |
| alpha-tocopherol | 1.5141 | 0.4307 | 3.51 | |
| gamma-tocotrienol | 2.4784 | 0.8537 | 2.90 | |
| gamma-tocopherol/beta-tocopherol | 1.2332 | 0.7413 | 1.66 | |
| Hemoglo and Porphyrin | | | | |
| heme | 2.7709 | 1.7554 | 1.57 | |
| pyrraline | 0.4532 | 0.1822 | 2.48 | |
| dimethyl sulfone | 1.3303 | 0.9648 | 1.37 | |
| thioproline | 0.9364 | 0.3376 | 2.77 | |

Fig. 4C (cont.)

| EM + TMZ ½ | EM + M₄N + TMZ ½ |
|---|---|
| + ↑ (above 1.20) | + ↑ (above 1.20) |
| Total number is about 100 biochemicals | 1. Betaine aldehyde – 1.83<br>2. N-acetylaspartate (NAA) – 2.30<br>3. Methylsuccinate – 1.61<br>4. Itaconate – 1.89<br>5. Gulonate – 1.50 |

| BIOCHEMICAL | SUPER PATHWAY | SUB PATHWAY |
|---|---|---|
| Betaine Aldehyde | Amino Acid | Glycine, Serine and Threonine Metabolism |
| N-acetylaspartate (NAA) | Amino Acid | Alanine and Aspartate Metabolism |
| Methylsuccinate | Amino Acid | Leucine, Isoleucine and Valine Metabolism |
| Itaconate | Energy | TCA Cycle |
| Gulonate* | Cofactors and Vitamins | Ascorbate and Aldarate Metabolism |

*Fig. 5B*

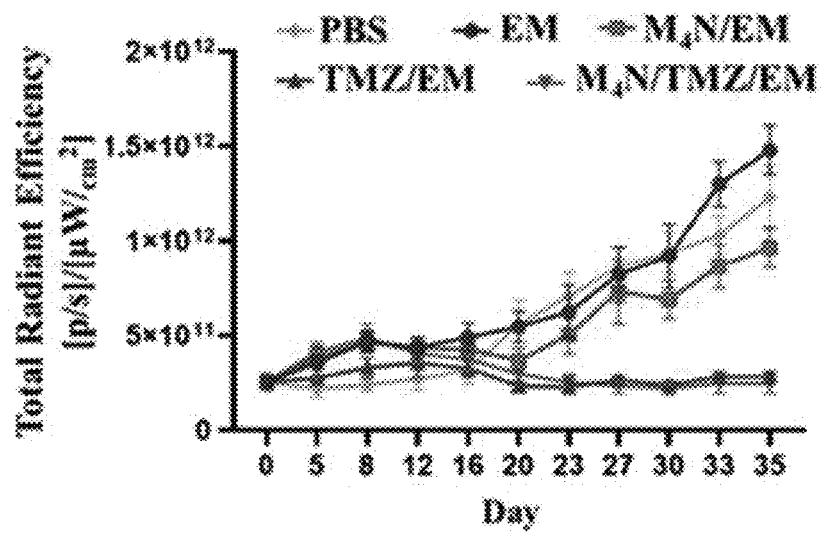
Fig. 7A
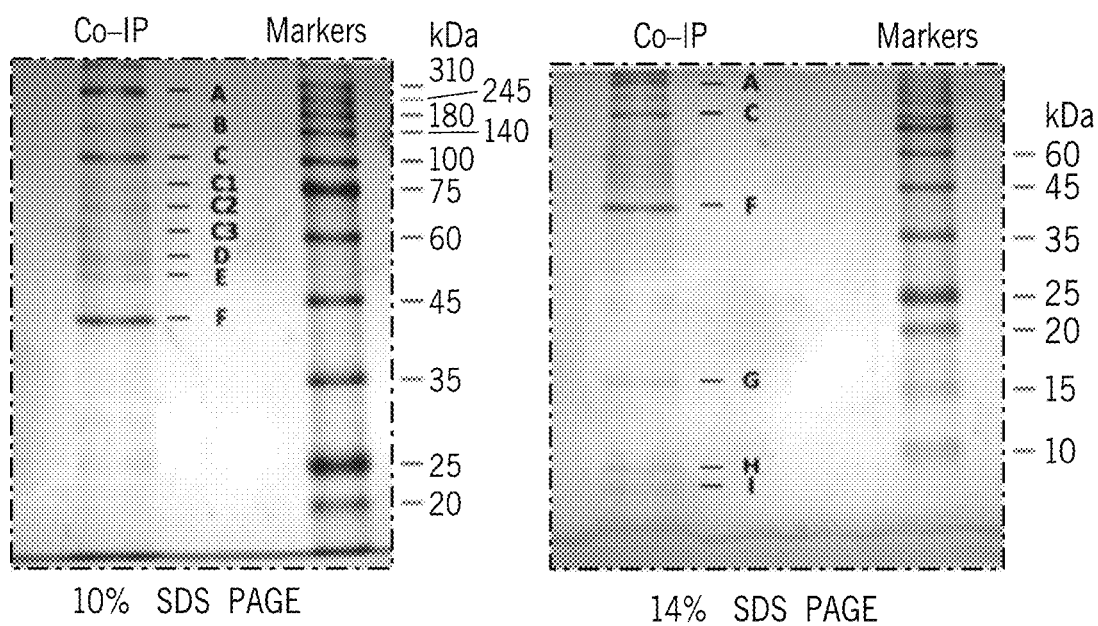
Fig. 7B
Fig. 7C

| Band | SDS MWT (kDa) | Symbol | Protein | MWT (kDa) |
|---|---|---|---|---|
| A | 245 | MYH9 | Myosin Heavy Chain 9 | 226.5 |
| B | 140 | MPRIP | Myosin phosphatase Rho-interacting protein | 116.5 |
| C | 100 | MVP | Major Vault Protein | 99.3 |
| C1 | 75 | LIMA1 | LIM domain and actin-binding protein 1 | 85.2 |
| C2 | 70 | RBM14 | RNA-binding protein 14 | 69.4 |
| C3 | 60 | DDX5 | ATP-Dependent RNA Helicase DDX5 | 69.4 |
| D | 50 | NONO | Non-POU domain-containing octamer-binding protein | 54.2 |
| E | 47.5 | TUBB | Tubulin beta chain | 49.6 |
| F | 40 | ACTB | Actin Beta | 41.7 |
| G | 15 | RPS18 | 40S Ribosomal Protein S18 | 17.7 |
| H | 9 | RPS27 | 40S Ribosomal Protein S27 | 9.5 |
| I | 8 | NDUFA4 | NDUFA4, Mitochondrial Complex Associated | 9.4 |

*Fig. 7G*

| Group Number | Treatment label | Dose/mouse/day | Animal Number |
|---|---|---|---|
| 1 | EM | Miglyol 812 N + Vitamin E TPGS NF (EM formulation) | 10, 19, 21 |
| 2 | M₄N/EM | M₄N (303 mg / kg)<br>(6.06 mg per 20 g of mouse body weight) | 2, 3, 4 |
| 3 | TMZ/EM | TMZ (5 mg / kg) | 6, 8, 13 |
| 4 | M₄N/TMZ/EM | M₄N (303 mg / kg)<br>(6.06 mg per 20 g of mouse body weight)<br>TMZ (5 mg / kg)<br>(0.1 mg per 20 g of mouse body weight) | 5, 7, 9, 14, 15<br>1, 11, 17, 23 |

*Fig. 10A*

| Group Number | Treatment label | Dose/mouse/day | Animal Number |
|---|---|---|---|
| 1 | EM | Miglyol 812 N + Vitamin E TPGS NF (EM formulation) | 1-1, 1-2, 1-3, 1-4, 1-5 |
| 2 | $M_4N$/EM | $M_4N$ (303 mg / kg)<br>(6.06 mg per 20 g of mouse body weight) | 2-1, 2-2, 2-3, 2-4, 2-5 |
| 3 | TMZ/EM | TMZ (5 mg / kg) | 3-1, 3-2, 3-3, 3-4, 3-5, 8-1, 8-2, 8-3 |
| 4 | $M_4N$/TMZ/EM | $M_4N$ (303 mg / kg)<br>(6.06 mg per 20 g of mouse body weight)<br>TMZ (5 mg / kg)<br>(0.1 mg per 20 g of mouse body weight) | 4-1, 4-2, 4-3, 4-4, 4-5, 9-1, 9-2, 9-3, 9-4 |
| 5 | $TMZ_{1/2}$/EM | TMZ (2.5 mg / kg) | 5-1, 5-2, 5-3, 5-4, 5-5 |
| 6 | $M_4N$/$TMZ_{1/2}$/EM | $M_4N$ (303 mg / kg)<br>(6.06 mg per 20 g of mouse body weight)<br>TMZ (2.5 mg / kg)<br>(0.05 mg per 20 g of mouse body weight) | 6-1, 6-2, 6-3, 6-4, 6-5 |

Fig. 10B

H: heart
S: spine
Arrow: lung tumor

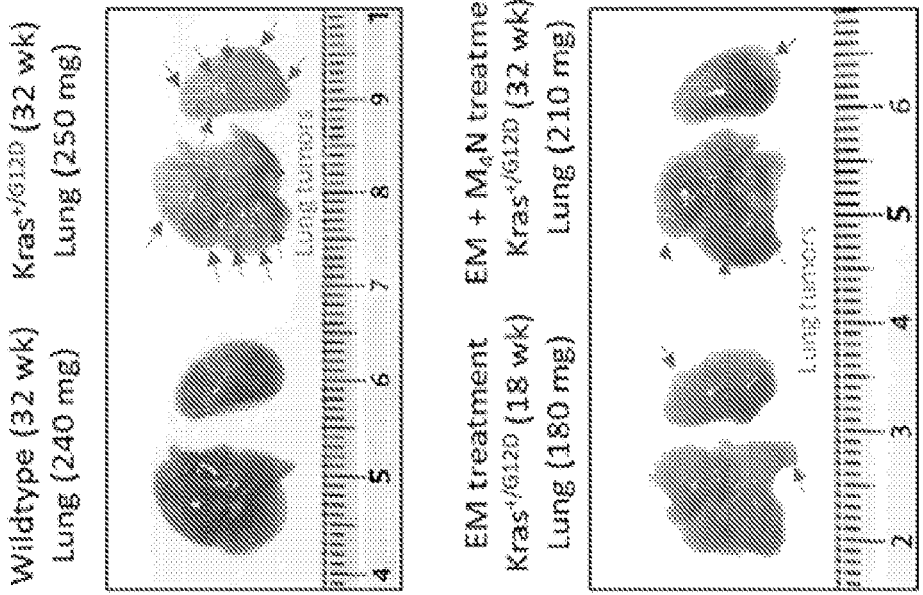
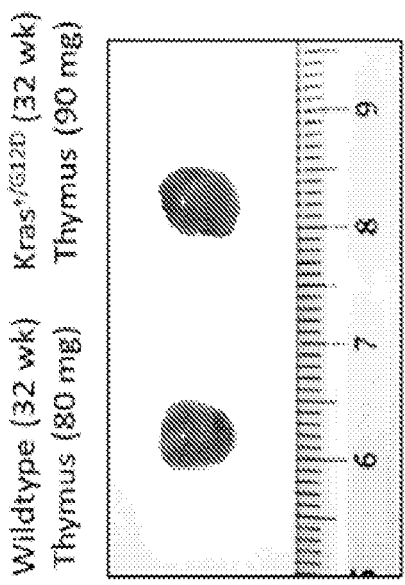
Fig. 15B
Fig. 15C

FORMULATIONS OF TERAMEPROCOL AND TEMOZOLOMIDE AND THEIR USE IN STIMULATION OF HUMORAL IMMUNITY IN TUMORS

CROSS-REFERENCE TO RELATED APPLICATIONS

The present invention claims the priority benefit of U.S. Provisional Patent Application No. 62/939,823, filed Nov. 25, 2019, and U.S. Provisional Patent Application No. 63/081,098, filed Sep. 21, 2020, each of which is incorporated herein by reference in its entirety.

BACKGROUND

The plant lignan nordihydroguaiaretic acid (NDGA) is extracted from the resin of the leaves of *Larrea tridentata*, a desert bush indigenous to the southwestern United States and Mexico. Derivatives of NDGA can inhibit the production of human immunodeficiency virus (HIV), herpes simplex virus (HSV), and human papillomavirus (HPV) transcripts by the deactivation of their Sp1-dependent promoters. Isolation and purification of plant lignans, however, is labor intensive and costly.

Tetra-O-methyl nordihydroguaiaretic acid ($M_4N$, Terameprocol) is the synthetic tetra-methylated derivative of NDGA. The chemical structure of $M_4N$ was designed to make it pharmacologically distinct from NDGA. $M_4N$ has been shown to possess antiviral and anti-cancer activities in cultured cells, in mouse models, and in human xenografts in nude mice. $M_4N$ causes cell cycle arrest at the G2 phase of the cell cycle most likely by suppressing Sp-1 regulated cdk expression. $M_4N$ has been administered to subjects in Phase I clinical trials orally and by intravenous infusion.

$M_4N$ is able to induce cell cycle arrest in mammalian cell lines as a transcription inhibitor. It selectively reduces transcription of growth-related genes that have promoters controlled by the Sp1 factor, such as cdc2, survivin, and VEGP. By blocking production of cdc2 and VEGF, $M_4N$ inhibits tumor growth and starves tumors by restricting growth of their blood supply.

$M_4N$ has been shown to arrest growth of a variety of human cells in vitro, the majority of which are part of the National Cancer Institute (NCI) panel of 60 cancer cell lines, including solid tumor cell lines (e.g., bladder, breast, colorectal, liver, lung, ovarian, pancreatic, prostate, and cervical carcinomas), and erythroleukemia cells. In vivo, $M_4N$ also decreases tumor cell growth and exhibits antitumor activity in a large number of tumor xenograft models, including human bladder, breast, colorectal liver, ovarian, pancreatic, prostate, and cervical carcinomas, and erythroleukemia, without apparent toxicity.

Further, $M_4N$ does not appear to be toxic to animals. For example, $M_4N$ retention in mouse organs following oral administration has been studied after short-term and long-term feeding and the results showed essentially no toxic effects even at concentrations as high as 906 µg/g of tissue. On daily (1 mg/day) IV injection of $M_4N$ for days, $M_4N$ accumulated in blood and tumors to levels above 1 mM in nude mice carrying human tumor xenografts.

$M_4N$ has some favorable therapeutic qualities in that it exhibits efficacy against several tumors by inhibiting cell growth. In human clinical trials, however, treatment with $M_4N$ in a short period of time and at low concentration does not generally eradicate disease and, upon cessation of treatment with $M_4N$, tumors are capable of growing back.

Malignant gliomas, including the most common type glioblastoma (GBM), are histologically heterogeneous and invasive tumors known as the most devastating neoplasms with high morbidity and mortality. About 24,000 new cases of adult primary malignant gliomas and an additional 3,000 pediatric gliomas are expected to be diagnosed in the United States in 2015. Despite multimodal treatment including surgery, radiotherapy, and chemotherapy, the disease recurs and is fatal. The overall survival of patients with newly diagnosed GBM is 42.4% at 6 months, 17.7% at 1 year, and only 3.3% at 2 years. Aside from poor survival, deficits in cognitive development also have been described thoroughly among children treated with radiation and systemic chemotherapy for brain tumors.

Given its public health importance, new treatment strategies to prolong patients' survival while minimizing the side effects and also improving the quality of life for patients with malignant gliomas is of interest. The unique anatomical, physiological and pathological feature of gliomas greatly limits the effectiveness of conventional radiotherapy and chemotherapy. The blood-brain barrier (BBB), a physiological barrier that protects the brain from toxic chemicals, presents the major obstacle for entrance of many therapeutically active compounds and nanoparticle-based drug delivery systems into brain. Systemic chemotherapy with paclitaxel (PTX) and other drugs did not show meaningful clinical benefit with regard to the survival of patients. In addition, the high level of P-glycoproteins in the BBB also has been reported to inhibit the brain penetration and pharmacological activities of many drugs. For this reason, most clinical trials and practices have been focusing on the use of BBB penetrable chemotherapeutics that are mainly alkylating agents that kill cells by attaching an alkyl group to DNA. Another characteristic feature of malignant gliomas is their ability to infiltrate and invade into neighboring tissues. Such local invasion remains an important cause of mortality and presents a great challenge for current clinical treatments, such as surgical intervention.

For most malignant gliomas, maximal surgical resection is usually performed whenever possible. Advances, such as MRI-guided neuronavigation, intraoperative MRI, functional MRI, intraoperative mapping, and fluorescence-guided surgery have improved the safety of surgery and increased the extent of resection that can be achieved. Malignant gliomas, however, cannot be completely eliminated surgically because of their infiltrative nature. After standard radiotherapy, 90% of the tumors recur at the original site and no significant benefit in survival was observed with increased dosages. Systemic chemotherapy, as an adjuvant therapy, prolongs the survival of glioma patients by a couple of months. The survival rate at 2 years among the patients who received radiotherapy and chemotherapy, e.g., temozolomide (TMZ), was greater than the rate among the patients who received radiotherapy alone (26.5% vs. 10.4%). Due to the systemic exposure, however, TMZ dosage is limited by the hematological toxicity, specifically thrombocytopenia and neutropenia.

SUMMARY

In some aspects, the presently disclosed subject matter provides a composition comprising an effective amount of a derivative of nordihydroguaiaretic acid (NDGA) of formula I:

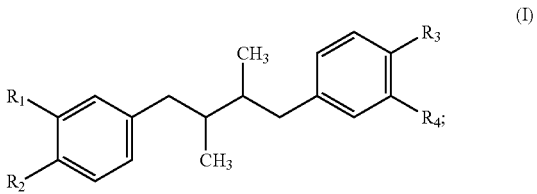

wherein $R_1$, $R_2$, $R_3$, and $R_4$ are each independently selected from the group consisting of straight-chain or branched lower alkyl, hydroxyl, alkoxyl, an amino acid residue, a substituted amino acid residue, a nitrogen-containing 5- or 6-membered heterocyclic ring or a saccharide residue; the amino acid residue, substituted amino acid residue, nitrogen-containing 5- or 6-membered heterocyclic ring or saccharide residue being optionally joined to the phenyl ring of the NDGA derivative by a linker of an oxygen atom and from 1 to 10 carbon atoms; and an effective amount of temozolomide (TMZ) dissolved or suspended in a formulation comprising at least one hydrophobic non-aqueous media and at least one hydrophilic non-aqueous media.

In some aspects, the NDGA derivative is tetra-o-methyl nordihydroguaiaretic acid ($M_4N$) or maltose-$M_3N$. In some aspects, the NDGA derivative has the following formula (II):

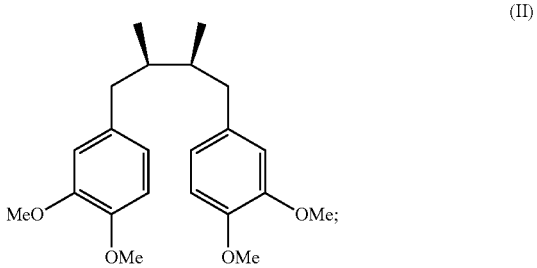 [SMILES: COc1ccc(C[C@@H](C)[C@@H](C)Cc2ccc(OC)c(OC)c2)cc1OC]

or a salt, solvate, or stereoisomer thereof. In some aspects, the NDGA derivative is $P_4N$ (tetrapiperidino NDGA, meso-2,3-dimethyl-1,4-bis(3,4-[2-(piperidino)ethoxyphenyl])butane tetrakishydrochloride salt) having the following formula:

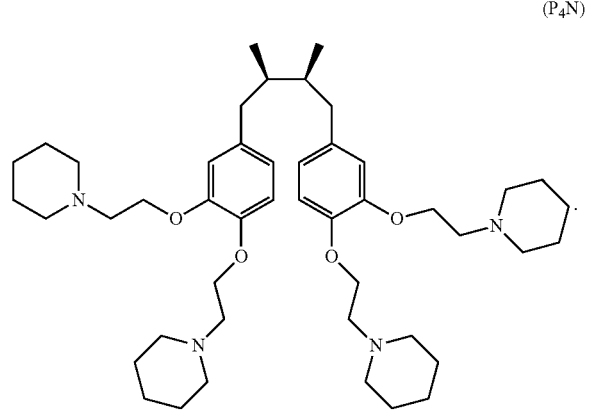 [SMILES: C[C@H](Cc1ccc(OCCN2CCCCC2)c(OCCN2CCCCC2)c1)[C@@H](C)Cc1ccc(OCCN2CCCCC2)c(OCCN2CCCCC2)c1]

In some aspects, the amount of temozolomide in the composition is between about 50 mg/m² to about 200 mg/m². In some aspects, the dosage of the NDGA derivative is between about 0.1 mg/kg to about 10 mg/kg. In some aspects, the concentration of the NDGA derivative is between about 0.01 μM to about 50 μM. In some aspects, the dosage of the NDGA derivative is between about 100 mg/kg to about 1000 mg/kg, or between about 300 mg/kg to about 600 mg/kg.

In some aspects, the hydrophobic non-aqueous media are selected from the group consisting of arachis oil, castor oil, cottonseed oil, maize (corn) oil, olive oil, sesame oil, soybean oil, sunflower oil, a medium-chain triglyceride, a caprylic/capric triglyceride, a propylene glycol diester of caprylic/capric acid, propylene glycol monolaurate, fractionated coconut oil, caprylic/capric/diglyceryl succinate, a medium-chain diester of propylene glycol, a partial ester of a diglyceride with a natural fatty acid, and a medium-chain mono- or di-glyceride. In particular aspects, the hydrophobic non-aqueous media is a fractionated coconut oil.

In some aspects, the hydrophilic non aqueous media are selected from the group consisting of a linoleoyl macrogolglyceride, a PEG-8 caprylic/capric glyceride, lauric acid, propylene glycol laurate, oleic acid, PEG MW>4000, polyglycerol dioleate, polyoxyethylene-polyoxypropylene copolymer, partial glycerides of hydroxylated unsaturated fatty acids, a PEG-6 caprylic/capric glycerides, polyoxyethylene glyceryl trioleate, polyoxyethylene(20)sorbitan monooleate, D-α-tocopheryl polyethylene glycol succinate (Vitamin E TPGS), hydrogenated polyoxyl castor oil, glycerin (with a content>5%), glycofurol 75, PEG MW<4000, N-methyl-2-pyrrollidone, propylene glycol, sorbitan monooleate, and diethylene glycol monoethylether. In particular aspects, the hydrophilic non aqueous media is Vitamin E TPGS.

In some aspects, the presently disclosed subject matter provides a use of the presently disclosed compositions, to increase expression of IL-21 in one or more tissues of a subject having a tumor.

In some aspects, the presently disclosed subject matter provides a use of the presently disclosed compositions to increase B cell proliferation and differentiation in one or more tissues of a subject having a tumor.

In some aspects, the presently disclosed subject matter provides a use of the presently disclosed compositions to increase secretion of anti-tumor immunoglobulins in one or more tissues of a subject having a tumor. In particular aspects, the anti-tumor immunoglobulins are of the IgA and IgG2a subtypes.

In some aspects, the presently disclosed subject matter provides a use of the presently disclosed compositions to suppress one or more major reprogrammed metabolic pathways of a tumor in a subject in need thereof including major reprogrammed metabolic pathways affecting the TCA cycle, fatty acid synthesis, and fatty acid metabolism.

In some aspects, the presently disclosed subject matter provides a use of the presently disclosed compositions to treat a glioblastoma in a subject in need thereof.

In some aspects, the presently disclosed subject matter provides a use of the presently disclosed compositions to treat lung cancer in a subject in need thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 3A:
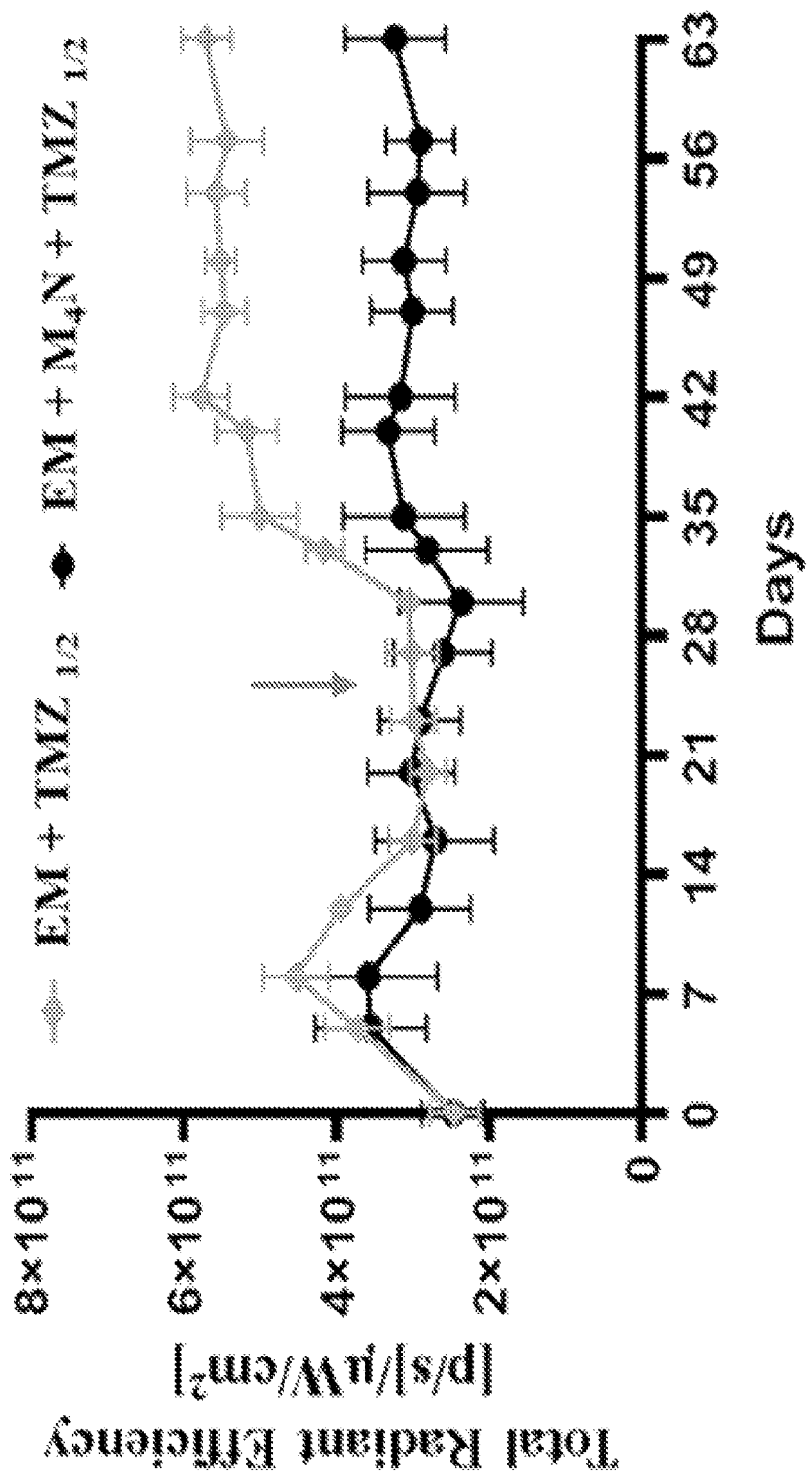
Figure 3B:
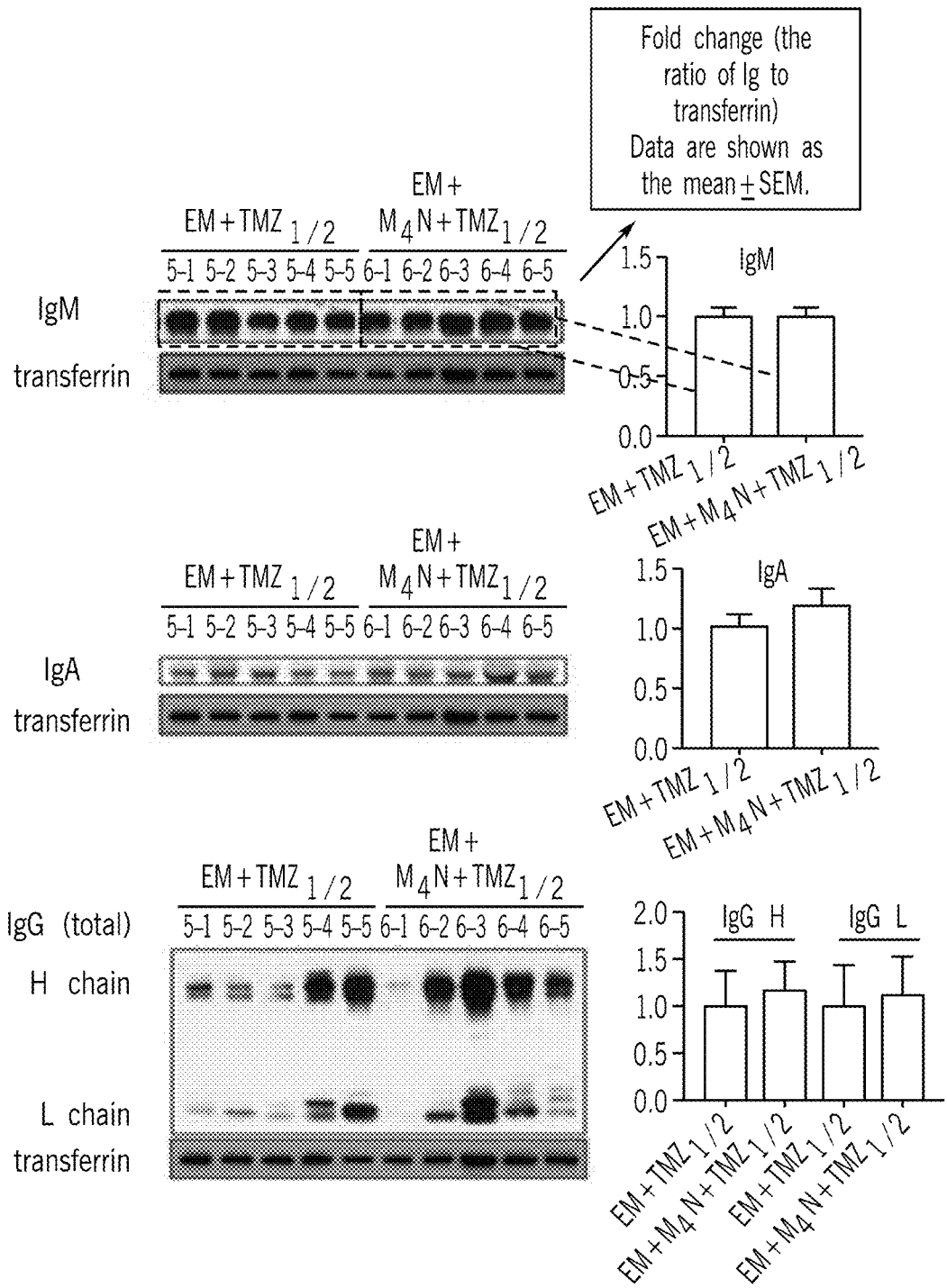
Figure 3B:
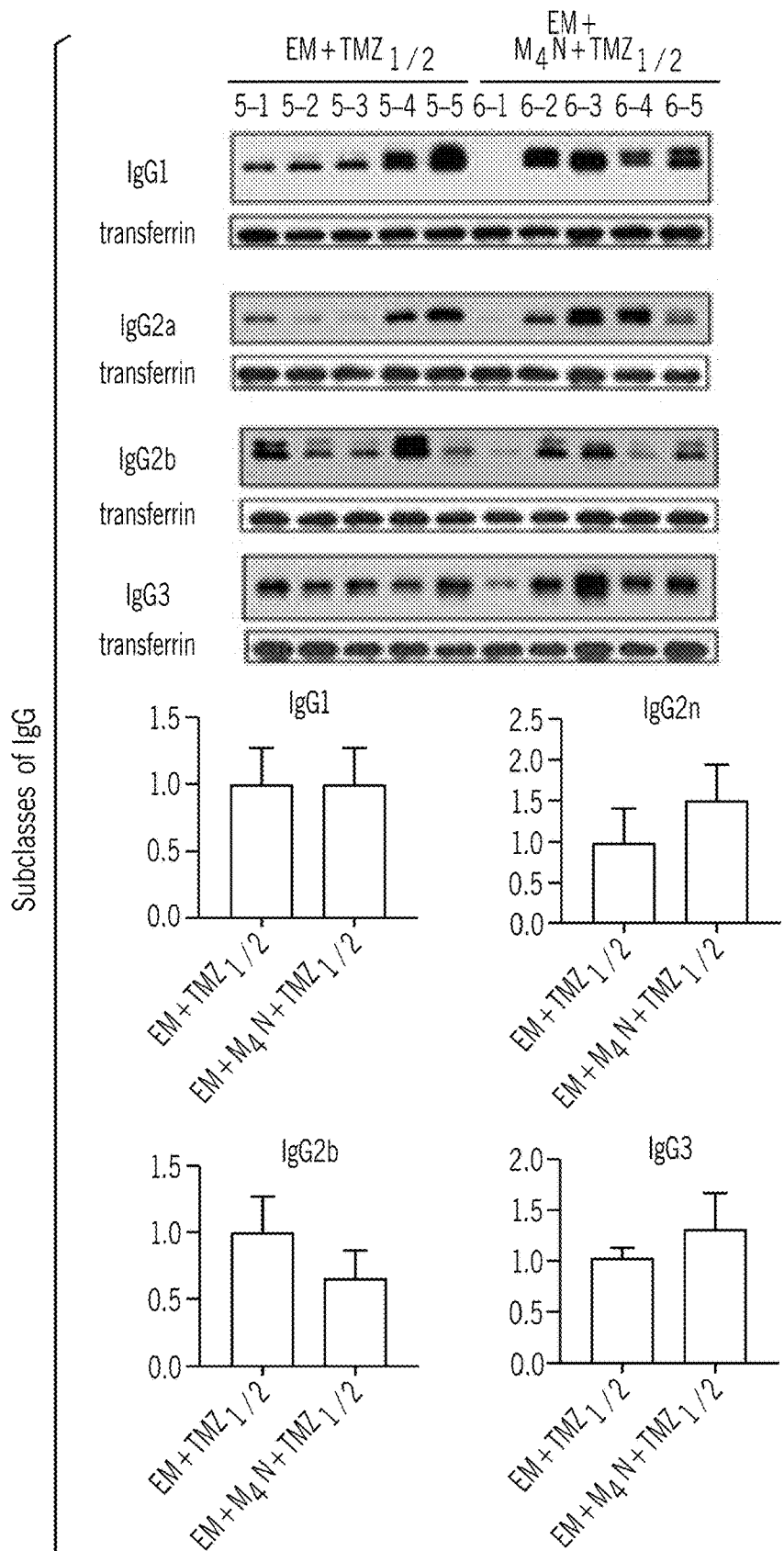
Figure 5A:
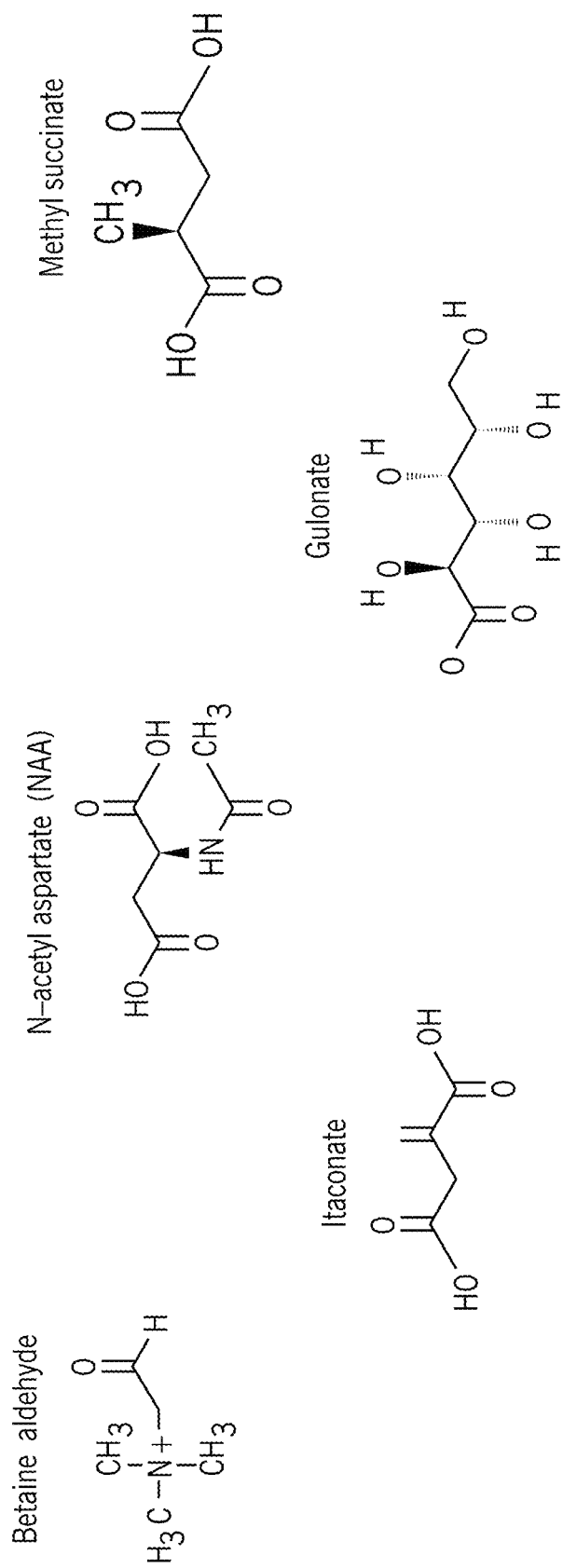
Figure 6A:
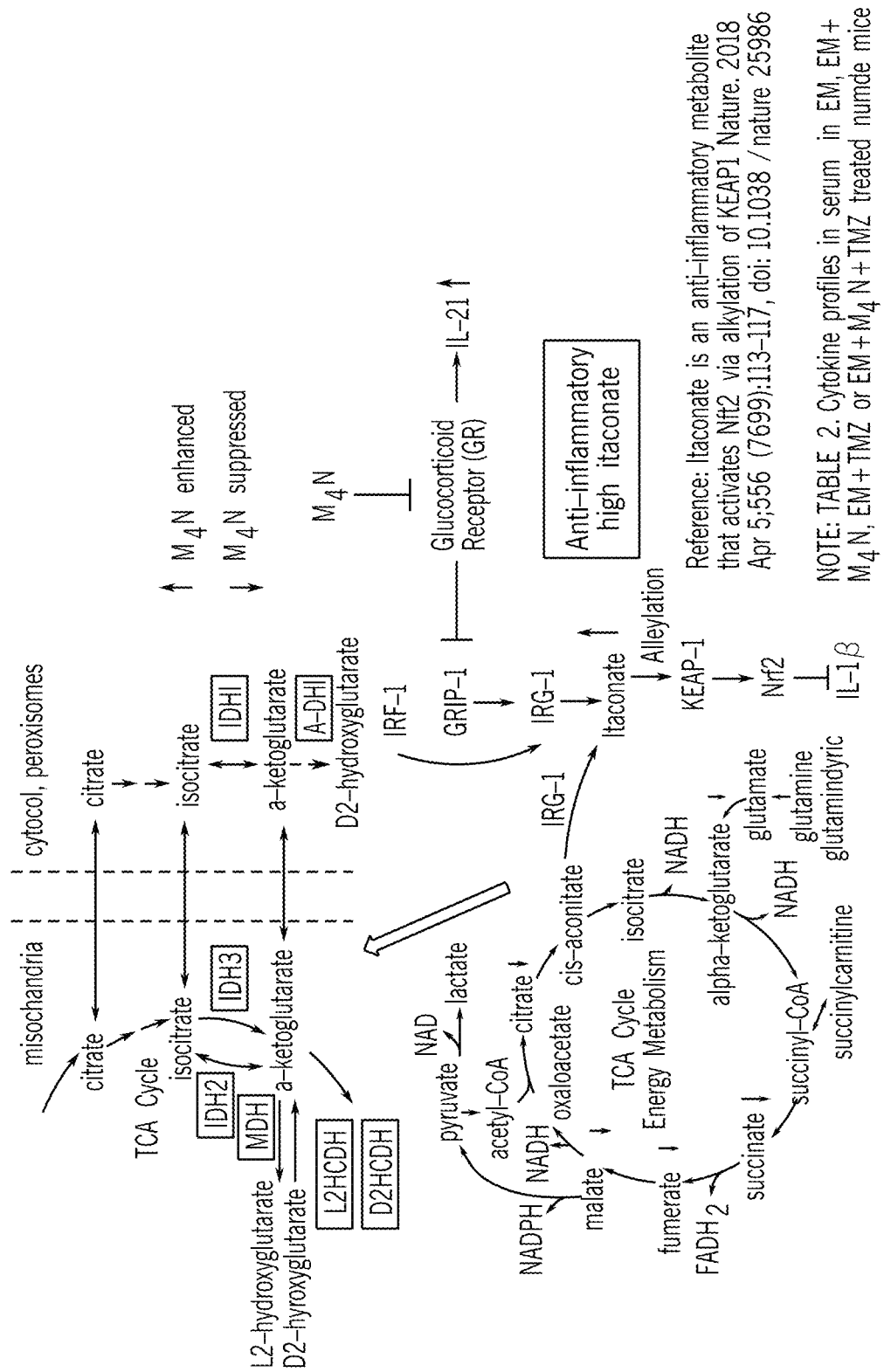
Figure 6B:
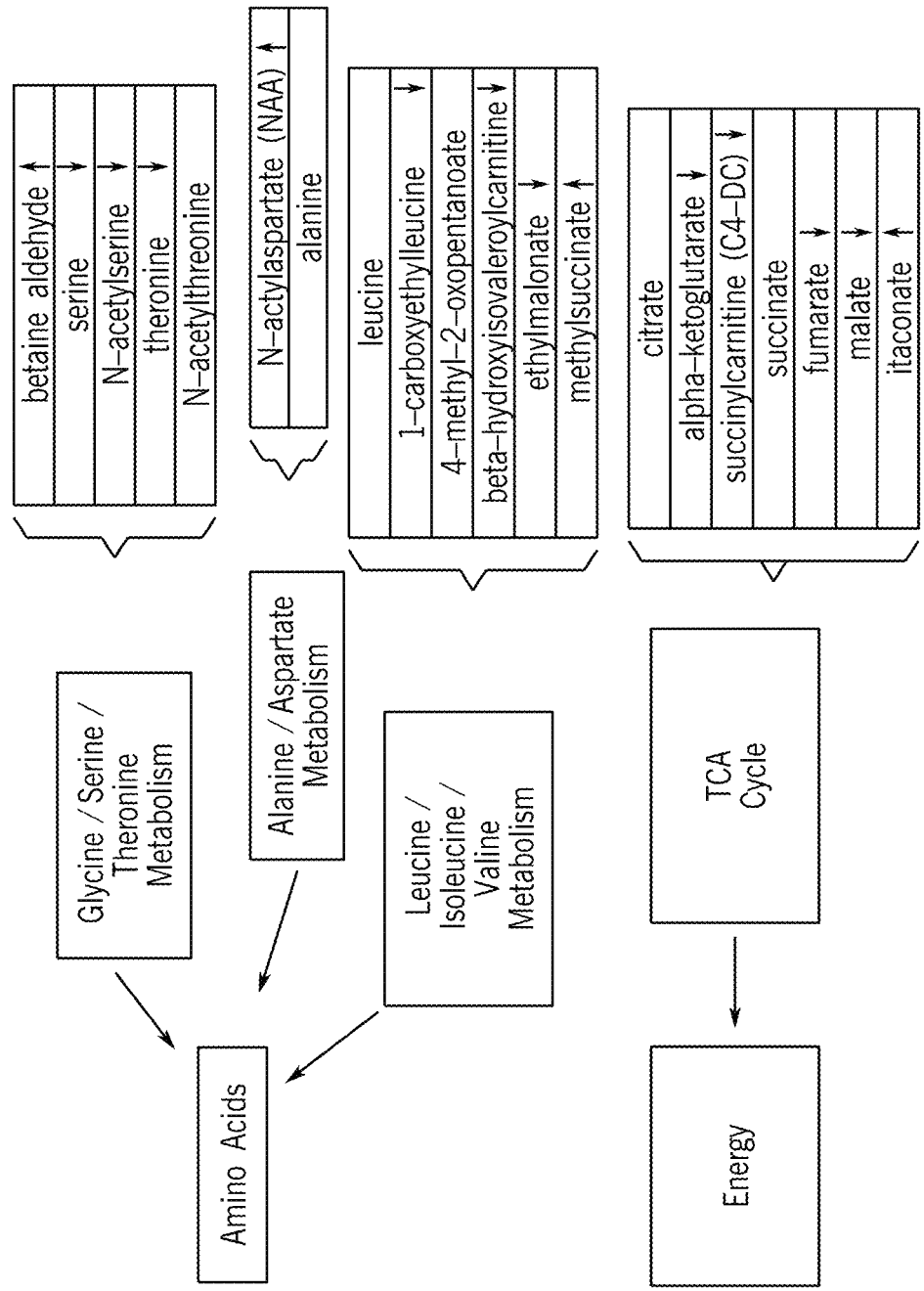
Figure 7D:
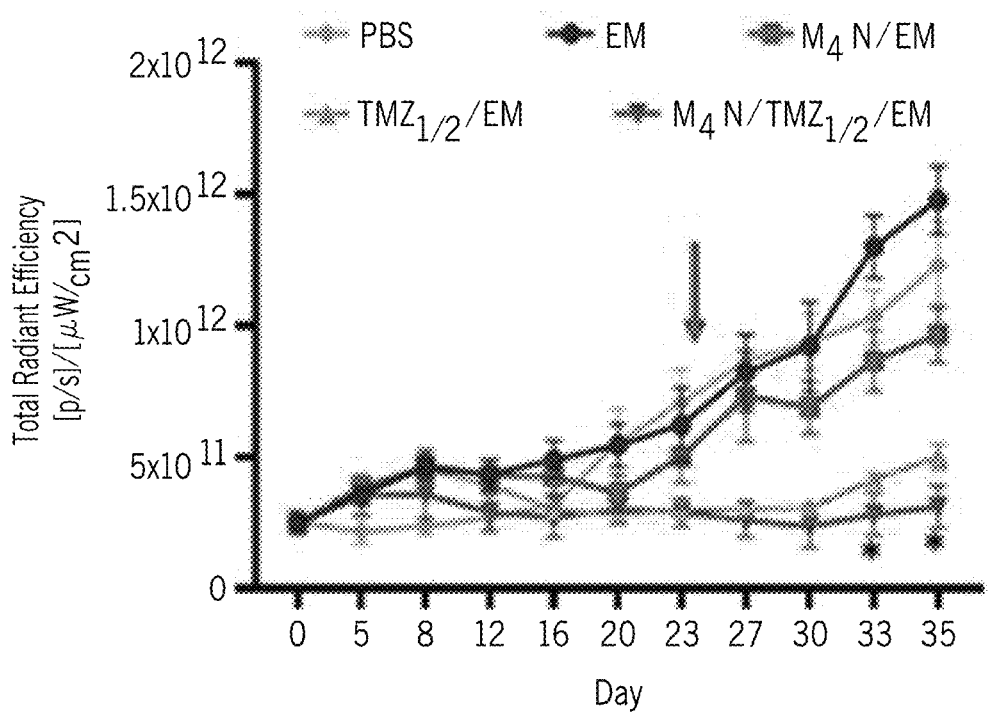
Figure 7E:
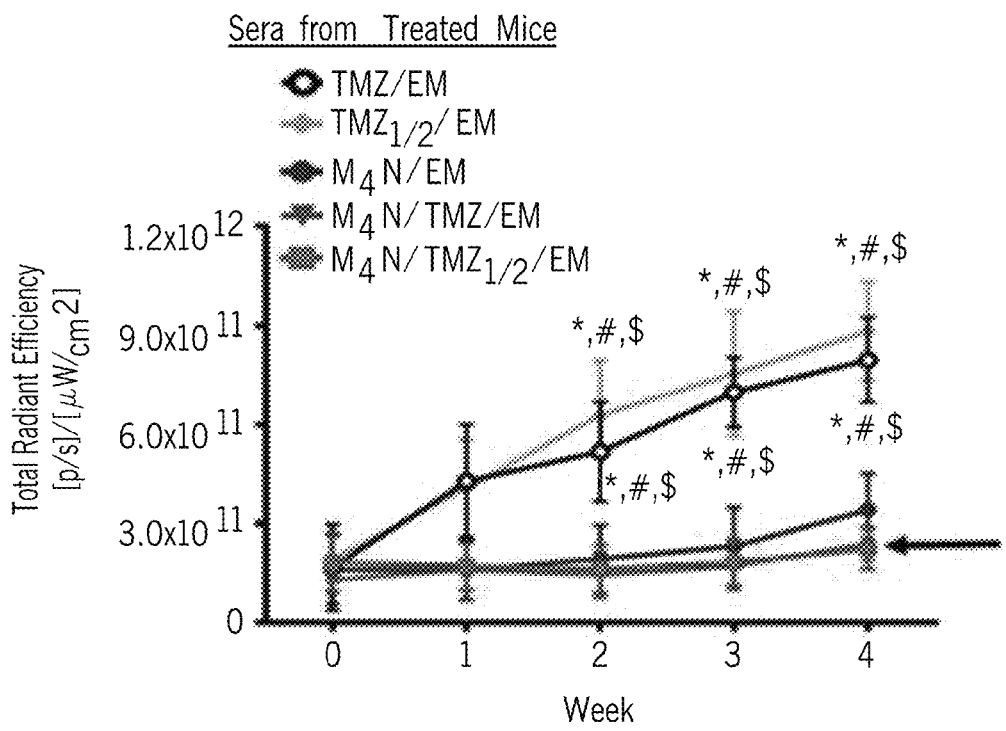
Figure 7F:
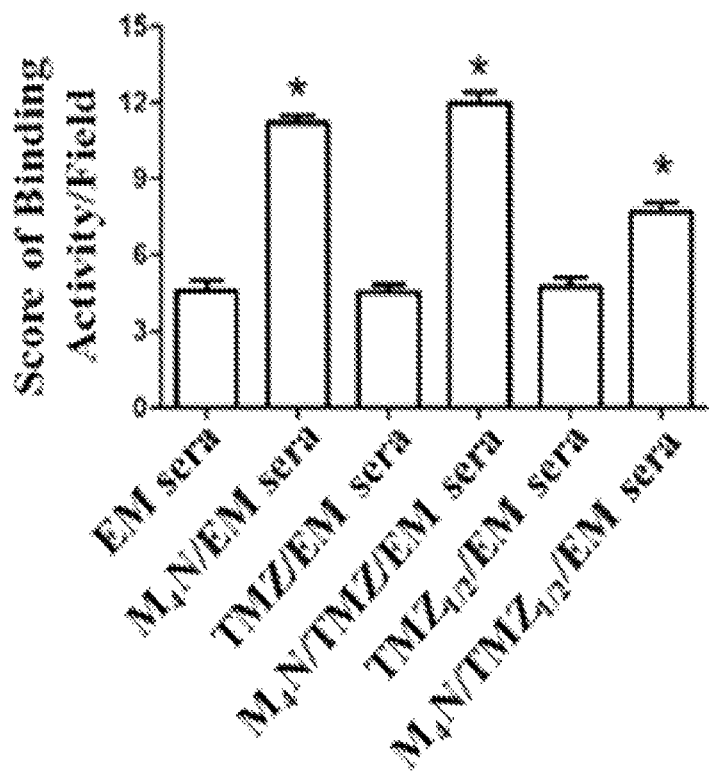
Figure 8:
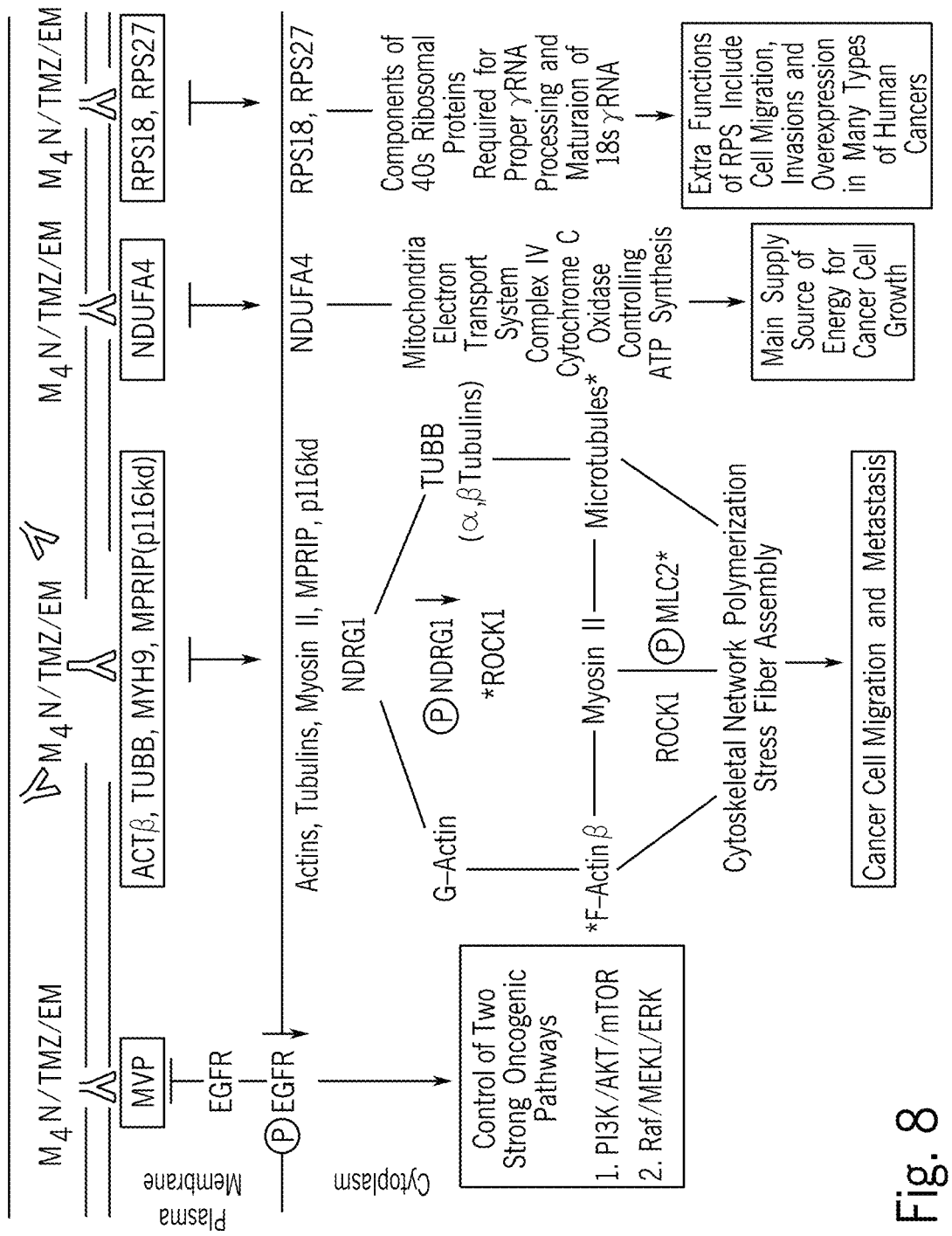
Figure 8:
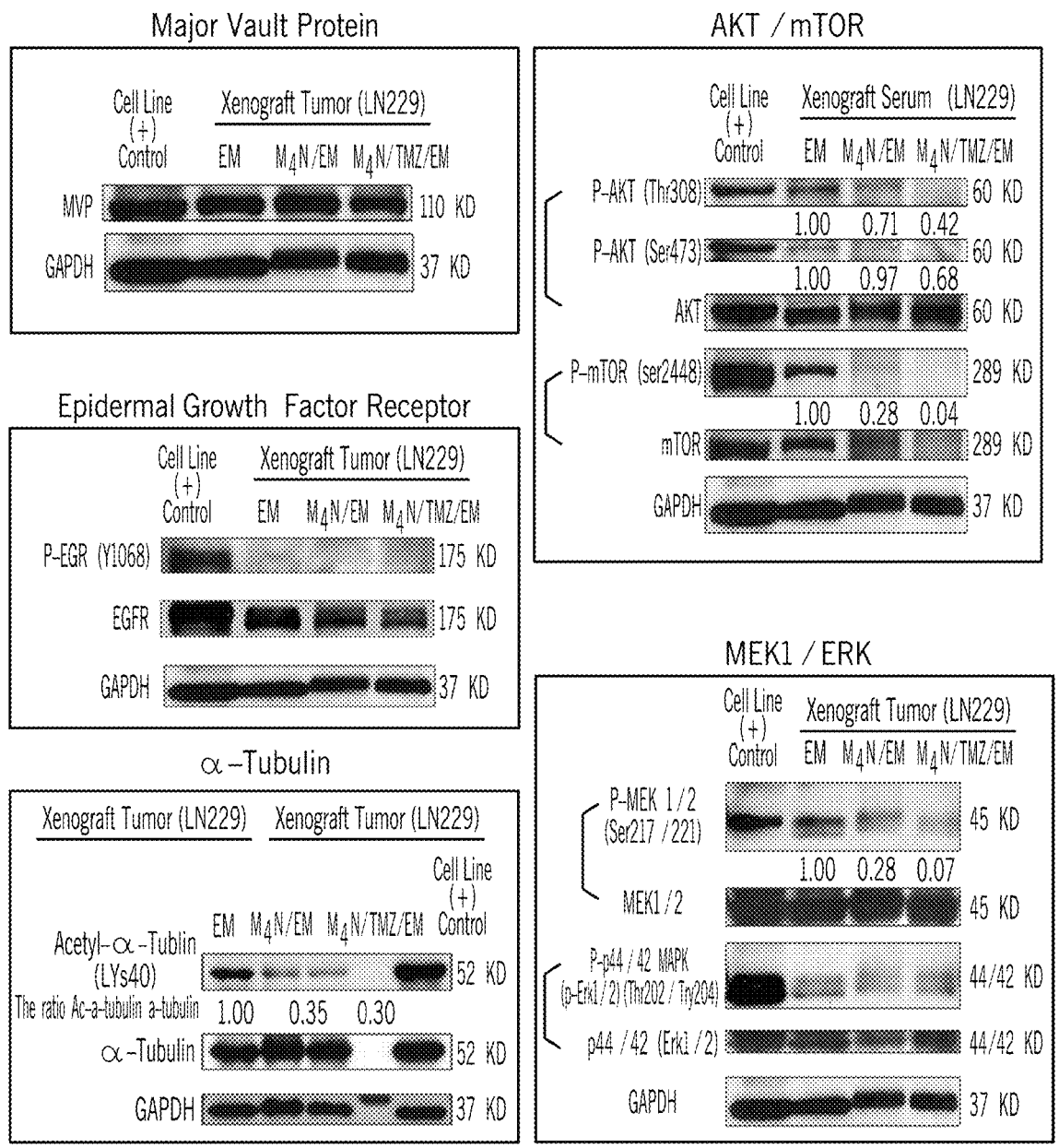
Figure 9:
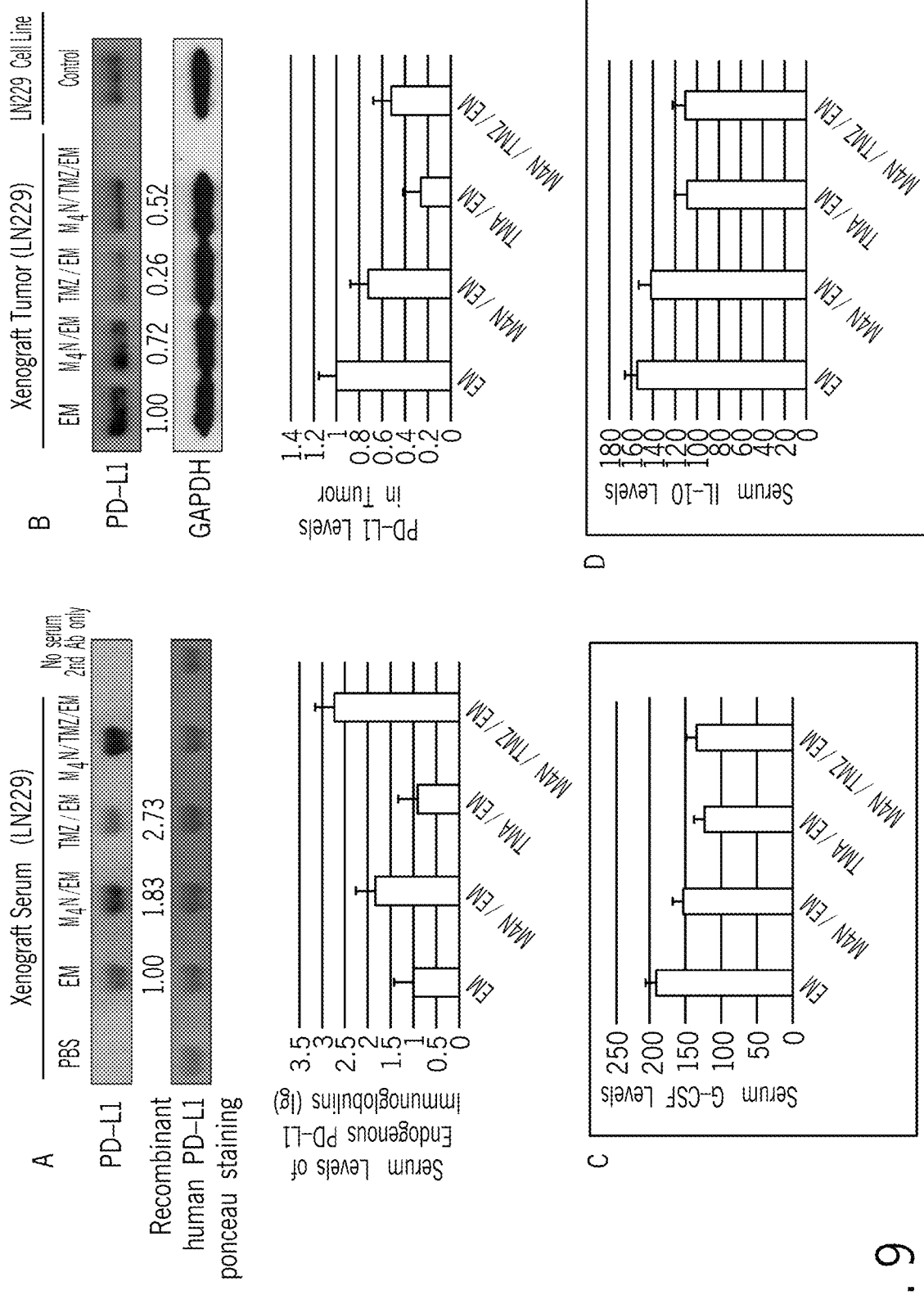
Figure 11A:
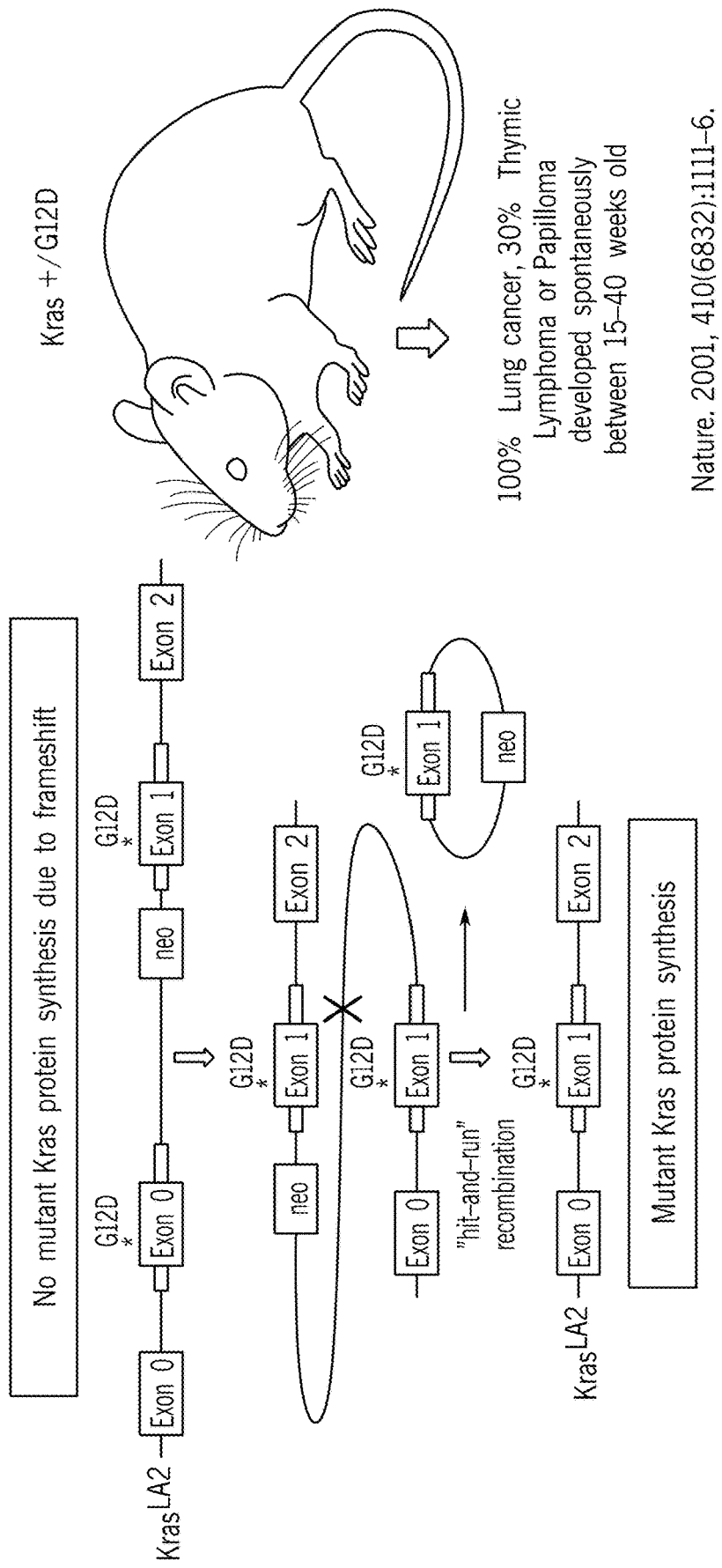
Figure 11B:
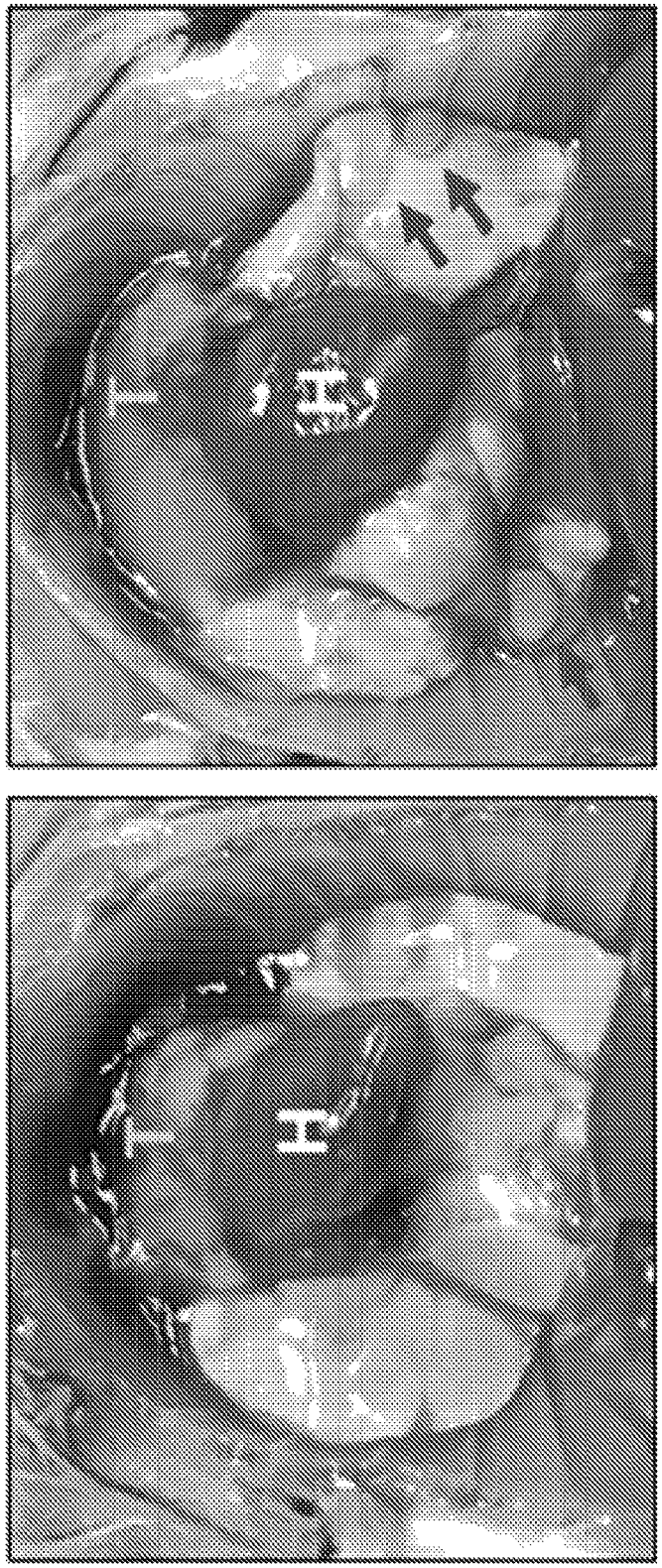
Figure 11C:
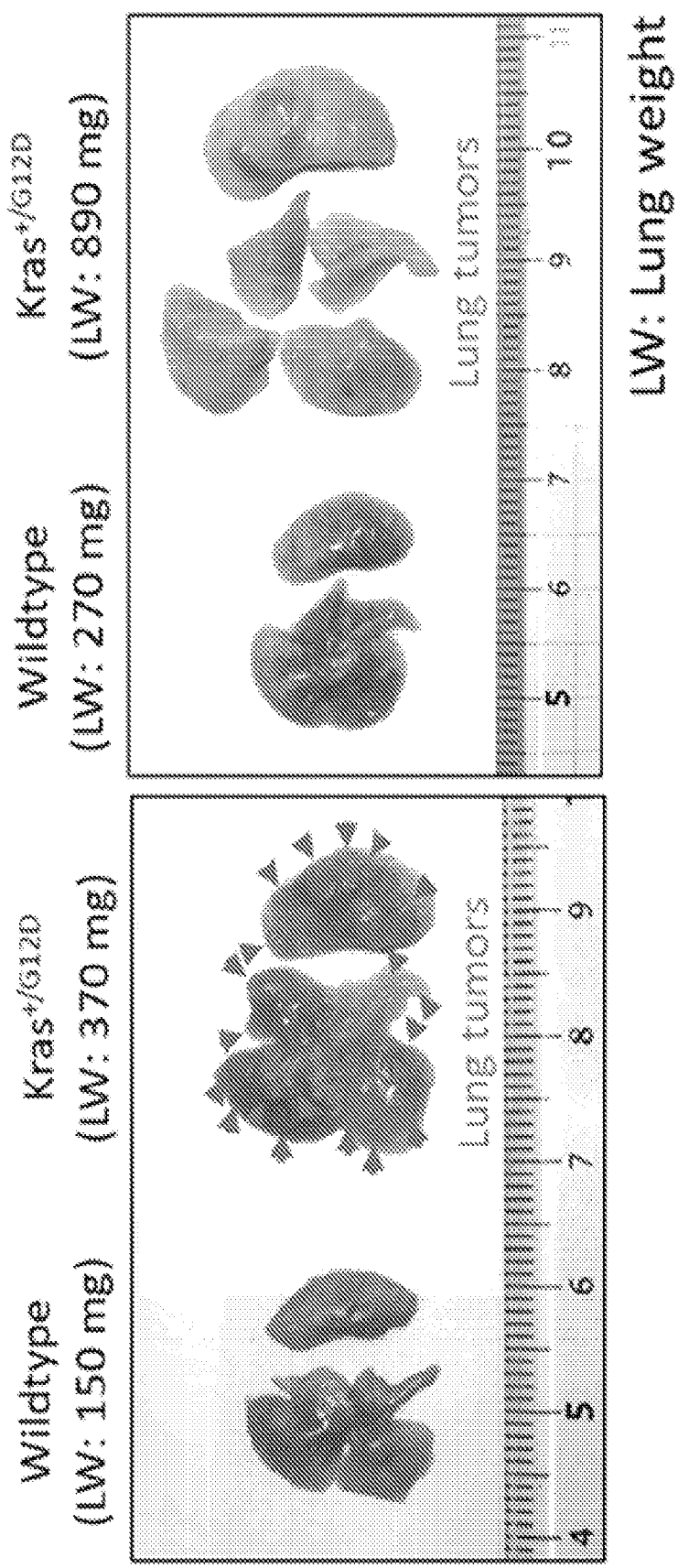
Figure 12A:
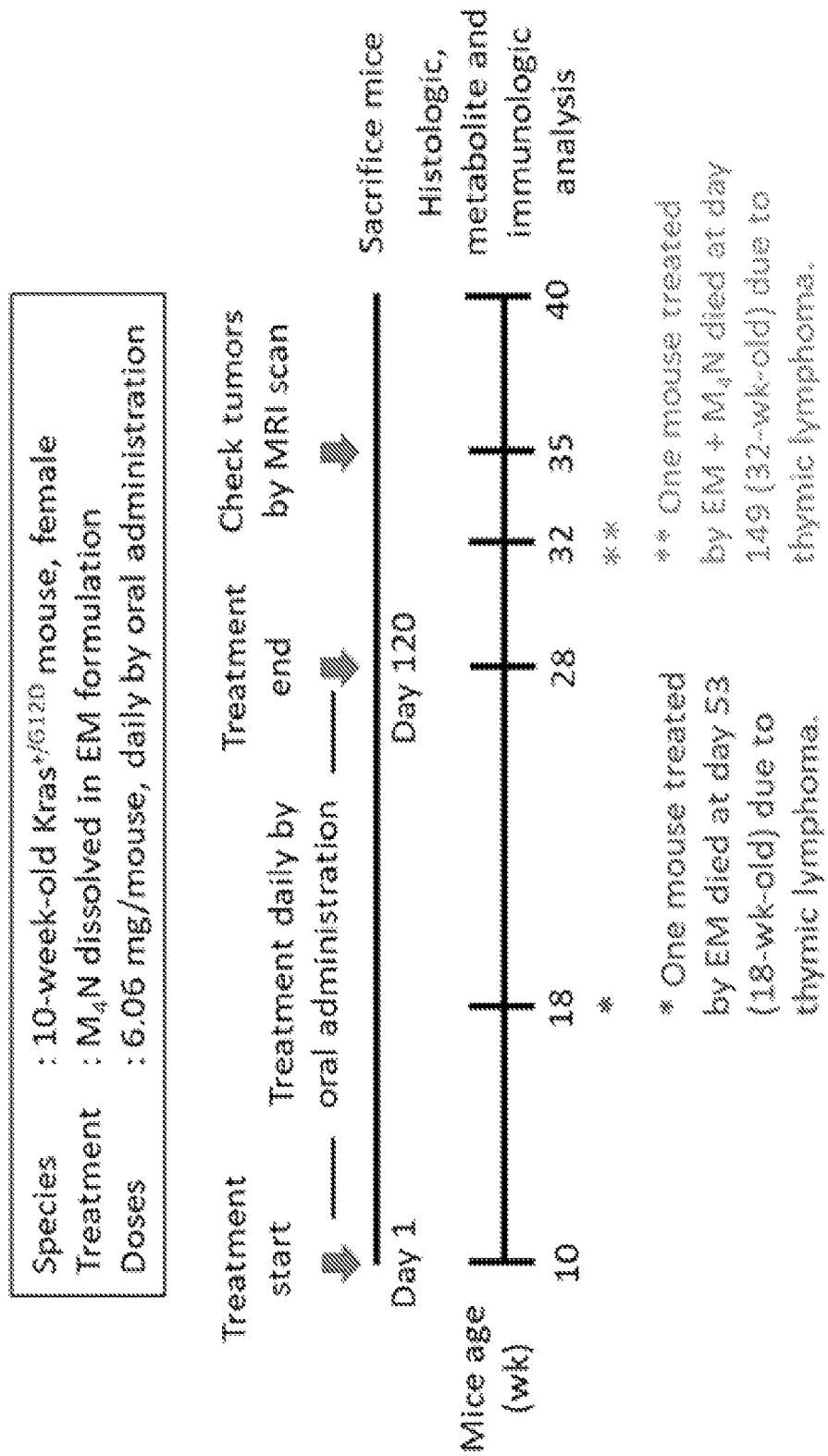
Figure 12B:
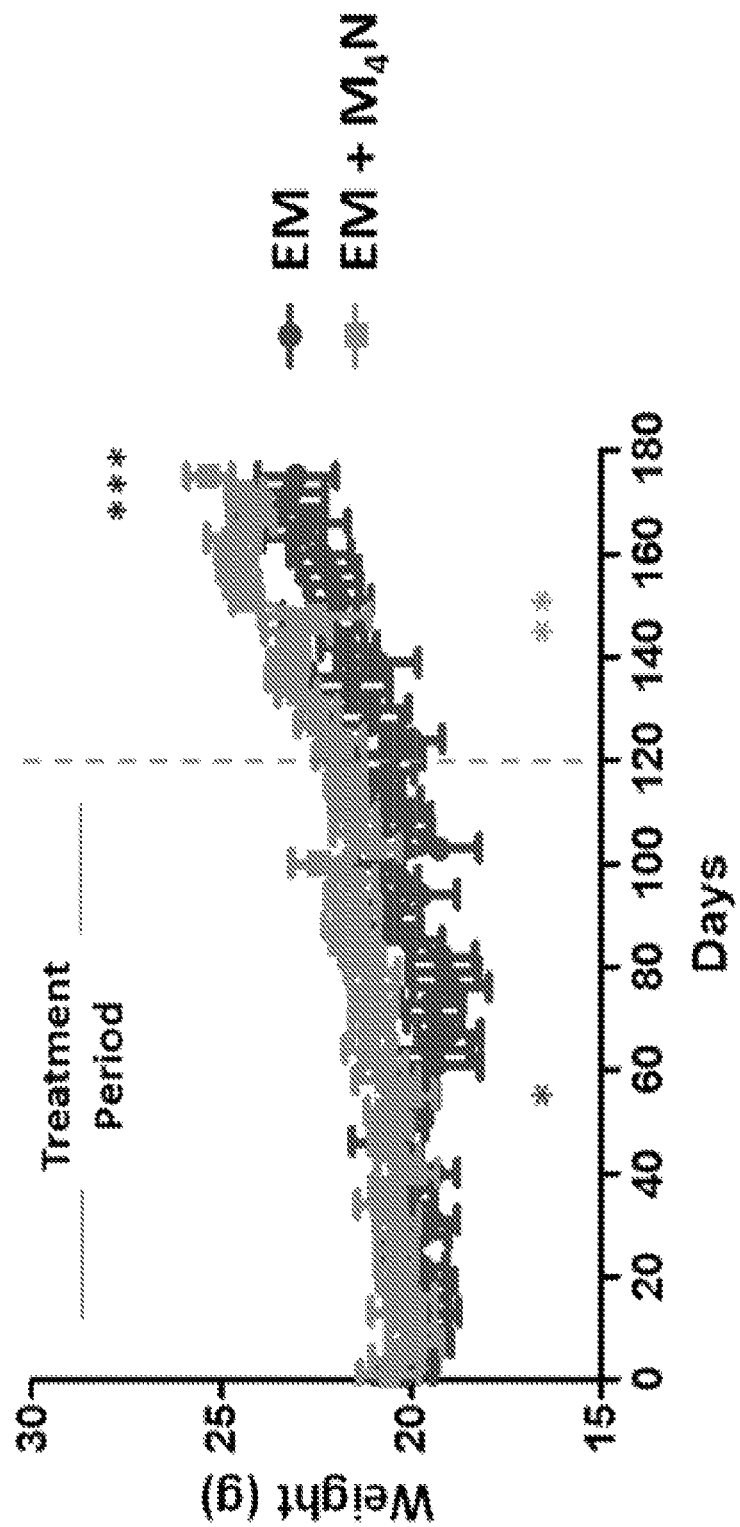
Figure 13:
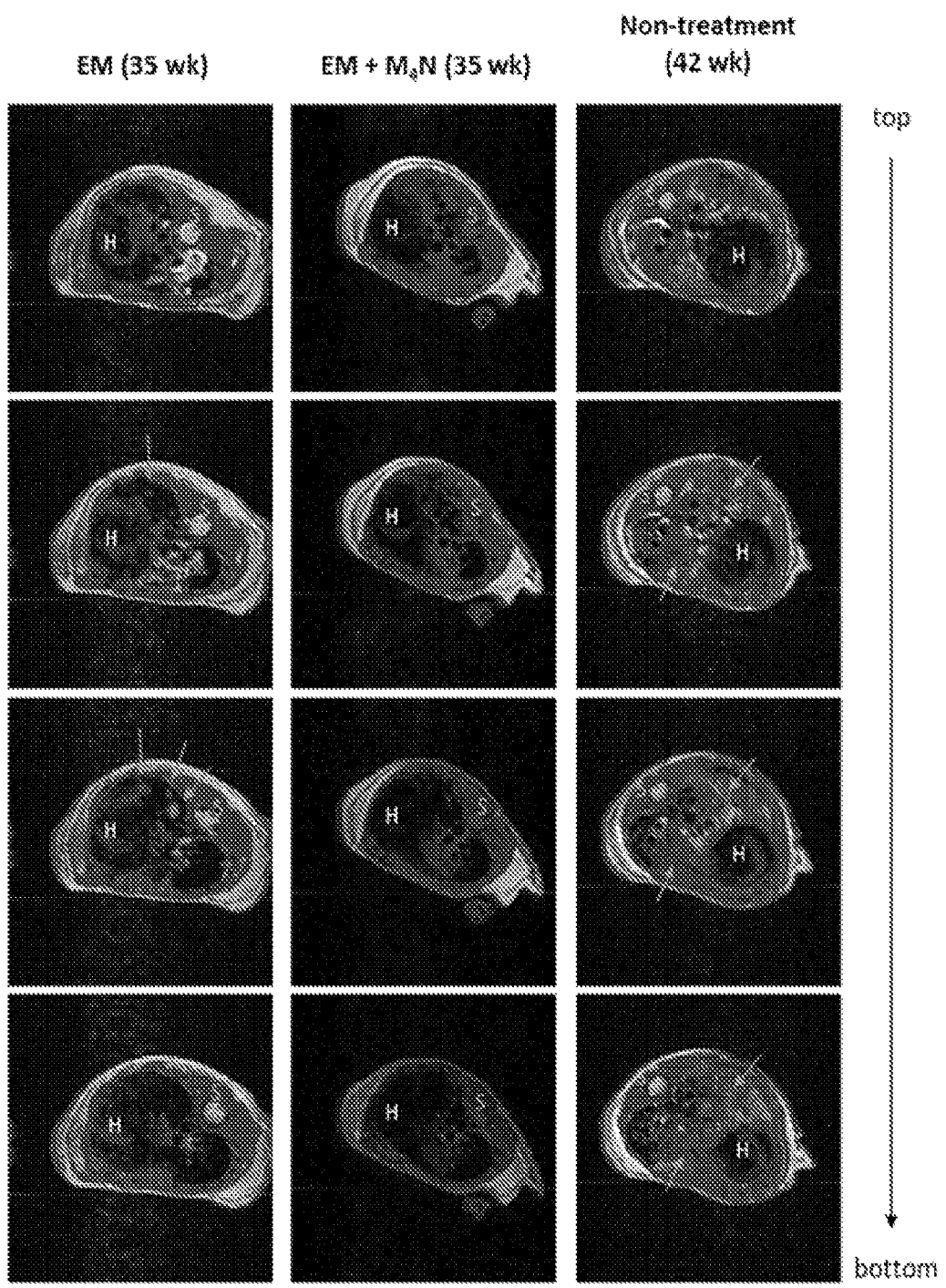
Figures 14A, 14B:
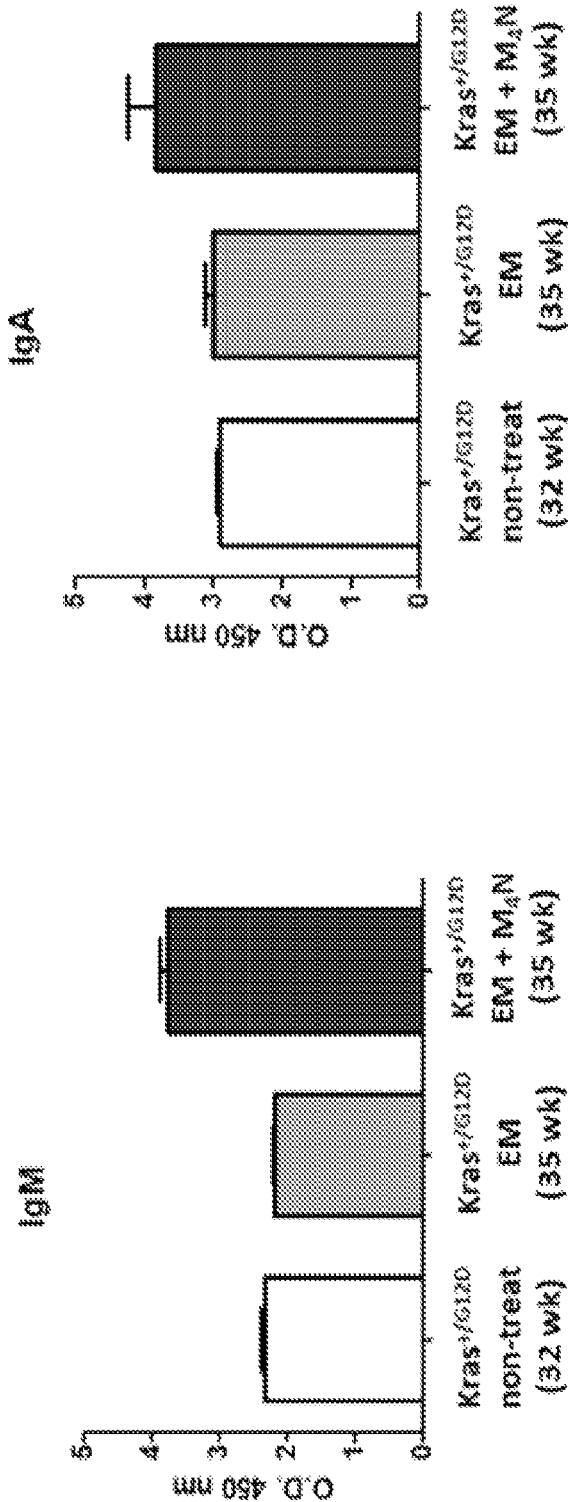
Figure 14D:
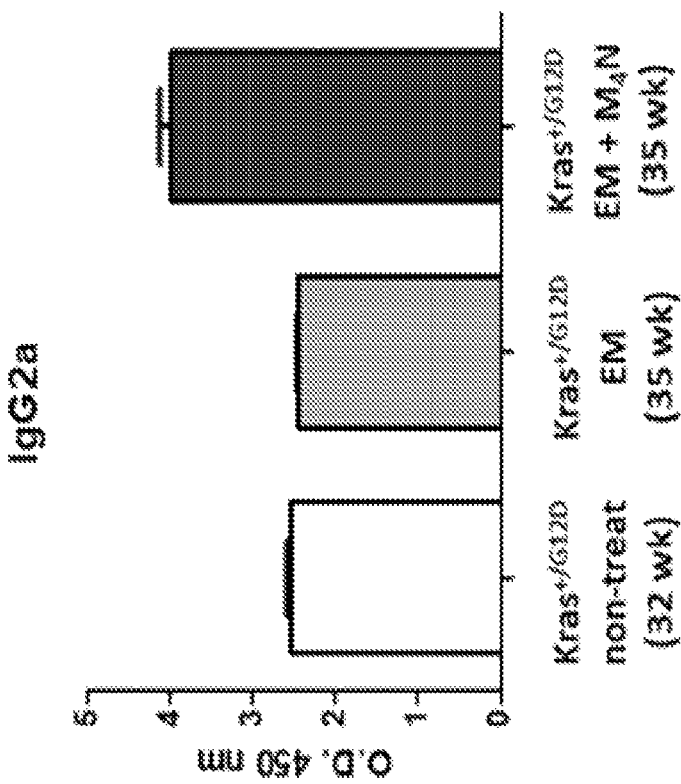
Figure 14C:
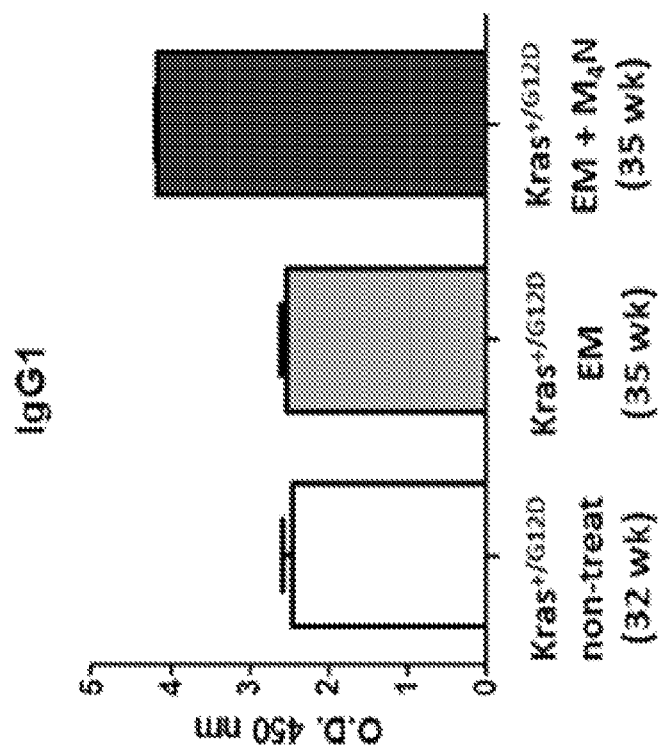
Figures 14E, 14F:
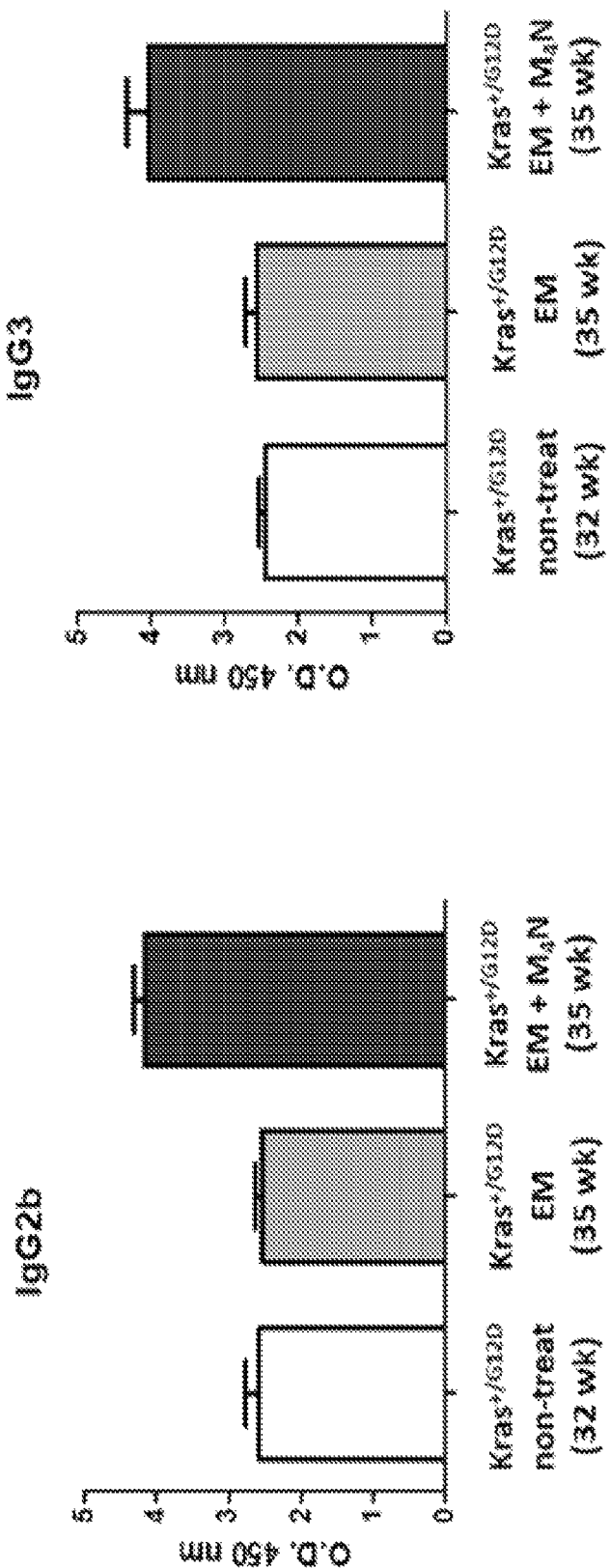
Figure 15A:
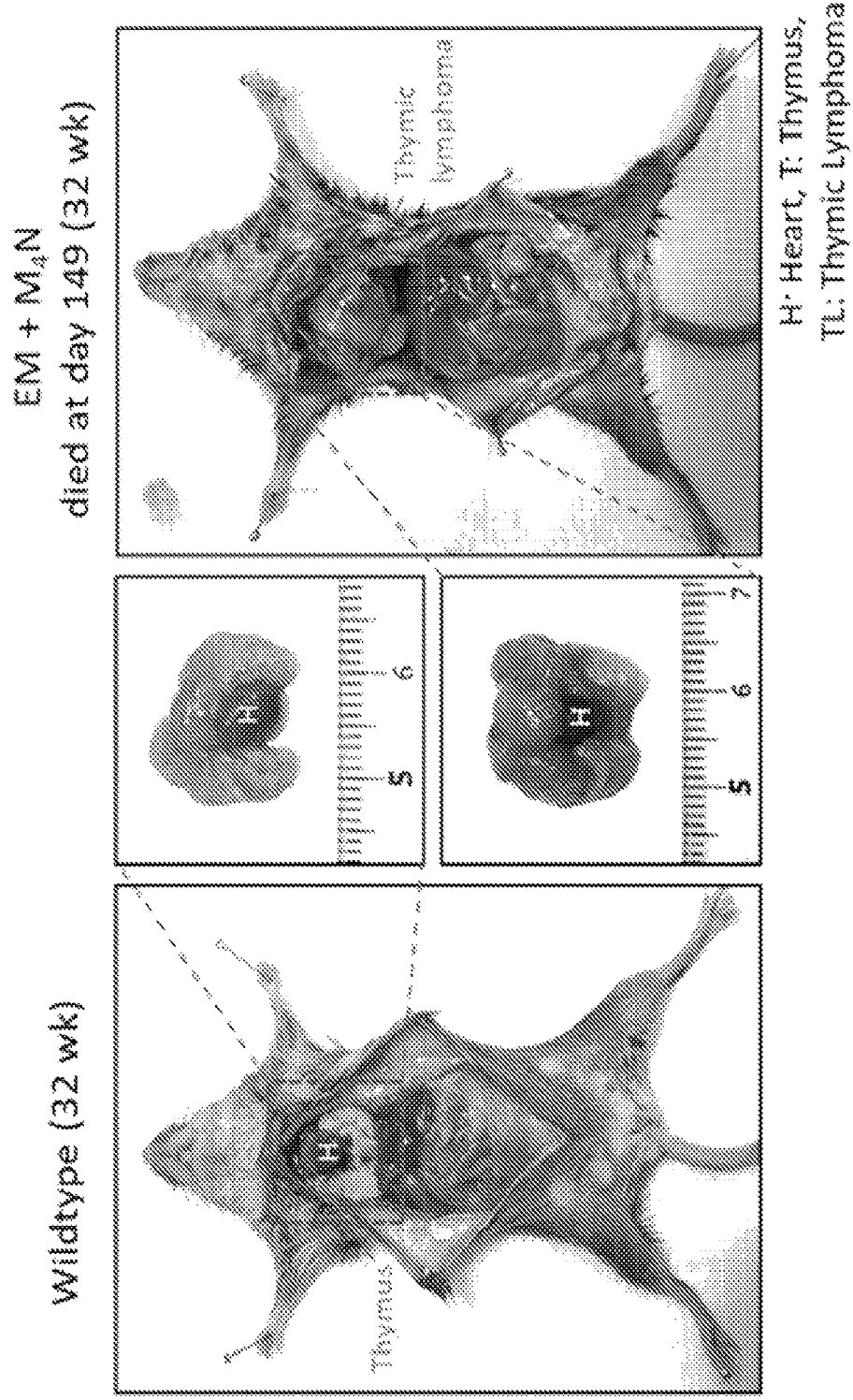

Having thus described the presently disclosed subject matter in general terms, reference will now be made to the accompanying Figures, which are not necessarily drawn to scale, and wherein:

FIG. 1A, FIG. 1B, FIG. 1C, FIG. 1D, FIG. 1E, FIG. 1F, FIG. 1G, FIG. 1H, FIG. 1I, FIG. 1J, and FIG. 1K demonstrate immune cells infiltration in LN229 tumors from xenograft mice after drug treatment. (FIG. 1A) Histological images of LN229 tumors from xenograft mice treated with EM formulation, EM+$M_4N$, EM+TMZ and EM+$M_4N$+TMZ (M/T). (FIG. 1B) Tumor infiltrating B cells (B220, red), (FIG. 1C) natural killer (NK) cells (NCR1, red), (FIG. 1D) macrophage (F4/80, green) and (FIG. 1E) gdT cells ($\gamma\delta$TCR, red). $M_4N$-induced IL-21 expression to regulate B cell proliferation and differentiation through downregulating GR transcription. (FIG. 1F) The expression of IL-21 in the tumor of LN229 xenograft mice after treatment was observed by IHC staining. (FIG. 1G) The tumor infiltrating B cells expressed IL-21R. (FIG. 1H) The scheme of $M_4N$-induced IL21/IL21R signaling for B cell activation. (FIG. 1I) The splenocytes of $M_4N$ or/and TMZ treated LN229 xenograft mice were isolated. The expression of Stat-3 and Prdm-1 were analyzed by RT-PCR (n=3). $M_4N$-GR binding assay: $M_4N$-GR-binding was determined by a PolarScreen Glucocorticoid Receptor Competitor Assay Kit (Thermo Fisher). Dexamethasone (Dex) was used as positive control. *$p<0.05$ compared to GR-GS group. (FIG. 1J) GR transcription assay. $M_4N$-GR transcriptional activity was measured by a GAL4 Reporter Kit (BPS Bioscience). GAL4 GR DNA binding domain (GR-DBD) Firefly-luciferase activities were calculated with internal control of Renilla luciferase activities (n=6). GAL4 DNA binding domain (mock-DBD) of firefly luciferase reporter plasmid was used as a control vector. Dex was used to induce GR transcription. Alsterpaullone (ALS) is a GR inhibitor and used as positive control. *$p<0.05$ compared to GR-DBD-Dex group. (FIG. 1K) Docking study shows $M_4N$ was docked in GR at the ligand binding site. The amino acids that potentially interact with $M_4N$ are noted. All figures are shown at 400× magnification;

FIG. 2 illustrates the chemical structures of $M_4N$, TMZ, Miglyol 812N and Vitamin E TPGS;

FIG. 3A and FIG. 3B show the anti-tumor effects of the presently disclosed drug combinations. Continuous oral treatments were given for 25 days and then treatment was stopped. No additional treatment was given for 38 days and on the 63rd day mice were sacrificed to collect tumors and sera samples for the analysis. (FIG. 3A) The difference of tumor size between 2 treatment groups (EM+$TMZ_{1/2}$ vs. EM+$M_4N$+$TMZ_{1/2}$) in LN229 xenograft mice. (FIG. 3B) The comparison of immunoglobulin levels in each treatment group (EM+$TMZ_{1/2}$ compared to EM+$M_4N$+$TMZ_{1/2}$). Western blot analysis as described in materials and methods. Quantification of ratio of Ig to transferrin, analyzed through areas in ImageJ plot curves. Error bars were plotted with standard error of mean (SEM, n=5) and two tailed, unpaired t-test by using GraphPad Prism software;

FIG. 4A, FIG. 4B, and FIG. 4C show biochemical fold change. EM+$TMZ_{1/2}$ and EM+$M_4N$+$TMZ_{1/2}$ showing the fold change of key metabolites analyzed for both treatments. Metabolite analysis was performed by Metabolon on tumor samples taken from LN229 xenograft mice. Continuous oral treatment was given for 25 days and then treatment was stopped and tumor samples were collected on the 63rd day after 38 days of no treatment. The sub-pathways for the listed metabolites are in bold type in the tables. Fold changes were calculated by taking the larger number and dividing it by the smaller number: (A/B) or (B/A). The calculated percent increases for EM+$TMZ_{1/2}$ that are above 1.20 are highlighted in green. The calculated percent increases for EM+$M_4N$+$TMZ_{1/2}$ that are above 1.20 are highlighted in red;

FIG. 5A and FIG. 5B are an illustration of the five metabolites that increased above 1.2-fold with EM+$M_4N$+$TMZ_{1/2}$ treatment. FIG. 5A. Illustration of the structures of metabolites affected by the drug treatment. FIG. 5B depicts a table showing the differences in metabolites due to treatment;

FIG. 6A and FIG. 6B illustrate changes in reprogrammed metabolism. FIG. 6A is a schematic showing the change in metabolites in the TCA cycle after treatment with $M_4N$. FIG. 6B is a chart showing the biochemical fold change after treatment;

FIG. 7A, FIG. 7B, FIG. 7C, FIG. 7D, FIG. 7E, FIG. 7F, and FIG. 7G depict the therapeutic effects of $M_4N$/TMZ combined treatments in vivo. (FIG. 7A) Tumor volumes in LN229 xenograft mice (n=5/group) treated with $M_4N$/EM or/and TMZ/EM by daily oral administration for 35 days. The antigen recognition ability by the $M_4N$/TMZ/EM induced endogenous antibodies were analyzed. (FIG. 7B) Co-immunoprecipitation of proteins from whole cell extracts of LN229 cells using antiserum from $M_4N$/TMZ/EM-treated LN229 xenograft mouse 423. The co-immunoprecipitated antigens were analyzed by 10% and 14% SDS polyacrylamide gel electrophoresis. These proteins were further identified by mass spectrometry, as the tumor associated antigens of LN229 cells that were recognized by the sera from $M_4N$/TMZ/EM treated mouse #23. (FIG. 7C) Combined antisera from another three $M_4N$/TMZ/EM-treated mice 4-1, 4-2 and 4-3 also were used to probe western blots of whole proteins of extracted from LN229 cells. FIG. 7B and FIG. 7C showed over ten similar molecules weight proteins that were displayed on these SDS-PAGEs. (FIG. 7D) In separate study, LN229 xenograft mice (n=5/group) treated with $M_4N$/EM or/and half dose of TMZ/EM by daily oral administration and treatment stopped at day 25 (red arrow). The tumor volumes of TMZ/EM, $M_4N$/TMZ/EM, $TMZ_{1/2}$/EM and $M_4N$/$TMZ_{1/2}$/EM were significantly different compared to EM group after day 23. *: $p<0.05$, compared to the $TMZ_{1/2}$/EM group. (FIG. 7E) Tumor volumes in LN229 xenograft mice (n=5/group) treated with i.v. injections of antisera from each drug treated group at week 0 and 2. Total radiant efficiency from nude mice at different time points were measured. *: $p<0.05$, compared to the $M_4N$/EM group; #: $p<0.05$, compared to $M_4N$/TMZ/EM group; $: $p<0.05$, compared to $M_4N$/$TMZ_{1/2}$/EM group. Binding activity of antisera to LN229 tumor tissues collected from LN299 tumor xenograft mice without any treatment. (FIG. 7F) Binding activity of antisera to LN229 tumor tissues collected from LN299 tumor xenograft mice without any treatment. (FIG. 7G) Table showing proteins identified by mass spectrometry, as the tumor associated antigens of LN229 cells that were recognized by the sera from $M_4N$/TMZ/EM treated mouse #23;

FIG. 8: (Left) Graphical representation of tumor associated antigens blocked by antibodies after $M_4N$/TMZ/EM treatment are known to affect metabolism and cell motility of cancer cells. FIG. 8 (Right) Western blots of Major Protein, AKT/mTOR, EGF, MEK1/ERK, and α-Tubulin showing changes after treatment regimen;

FIG. 9A. FIG. 9B, FIG. 9C, and FIG. 9D demonstrate inhibition of immunosuppressive proteins and cytokines by antibodies enriched in the sera of $M_4N$/TMZ/EM treated cice (FIG. 9A) PD-L1 mouse endogenous antibody against human recombinant PD-1 protein. (FIG. 9B) The level of PD-L1 protein antigen is high in LN229 tumors in EM alone treated mice compared to those from $M_4N$/EM, TMZ/EM or $M_4N$/TMZ/EM treated mice. Lowering the level of PD-L1 in LN229 tumors by treatment with the sera of $M_4N$/TMZ/EM treated mice. (FIG. 9C) Levels of G-CSF in serum of $M_4N$/EM, TMZ/EM or $M_4N$/TMZ/EM treated nude mice shows a decrease of G-CSF likely from immune suppressive neutrophils (see PNAS, E566-E575; Jan. 26, 2015) in all three compared to EM treated alone. (FIG. 9D) Levels of IL-10 (anti-inflammatory cytokine) in serum of TMZ/EM or $M_4N$/TMZ/EM treated nude mice shows a decrease of IL-10. Standard Error (+SE) calculations for (FIG. 9C) and (FIG. 9D) were done using data from five mice in each group (n=5);

FIG. 10A and FIG. 10B are tables showing representative treatment dosing regimens of mice used in the present study;

FIG. 11A, FIG. 11B, and FIG. 11C depict a Kras G12D-driven cancer mouse model. (FIG. 11A) The illustration of Kras G12D genetic engineering allele and "hit-and-run" recombination occurring spontaneously to induce cancers in mice. (FIG. 11B) The lung tumors in 32 weeks old Kras G12D mouse. H, heart; T, thymus; lung tumors were indicated by arrows. (FIG. 11C) The lungs in Kras G12D mice. Left, 44 weeks old, male Kras mouse; right, 40 weeks old, female Kras mouse; LW, the weight of lung;

FIG. 12A and FIG. 12B show $M_4N$ treatment in Kras G12D mice. (FIG. 12A) The treatment schedule of EM formulation or EM plus $M_4N$. Two mice died at day 53 and day 149 as indicated. (FIG. 12B) The weight curve of mice during and after treatment. The weight of each mouse was monitored every three days. EM formulation treated mice, n=4; EM+$M_4N$ treated mice, n=5;

FIG. 13 depicts MRI of lung tumors in mice. The axial images were taken by 9.4 T MRI; RARE T2-weighted; slice thickness=1 mm; total slice number=24. The scan started from neck to bottom of ribs. The tumor size ≥1 mm is detectable by this scan. H, heart; S, spine; Arrow: lung tumor;

FIG. 14A, FIG. 14B, FIG. 14C, FIG. 14D, FIG. 14E, and FIG. 14F show the serum levels of immunoglobulins in treated mice. The serum levels of six immunoglobulins IgM, IgA and the IgG subclasses (IgG1, IgG2a, IgG2b and IgG3) were detected using an uncoated ELISA Kit (ThermoFisher Scientific, The Mouse Immunoglobulin (Ig) Isotyping Ready-SET-Go: 88-50630). The serum samples were extracted from mice tail veins hours after MR Imaging; and FIG. 15A, FIG. 15B, and FIG. 15C depict the thymic lymphoma in Kras G12D mice. (FIG. 15A) The position and size of thymic lymphoma in EM+$M_4N$ treated mouse. (FIG. 15B and FIG. 15C) The thymic lymphomas and lungs from both treated mice compared to wildtype or untreated Kras G12D mice.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Novel Formulations of Terameprocol and Temozolomide and their Use in Stimulation of Humoral Immunity in Tumors Although it was found that $M_4N$ can suppress cancer cell lines in vitro and in tumor xenografts in vivo, how it modulates a primary tumor's metabolism and microenvironment to prevent or inhibit its growth is still unknown. In the presently disclosed subject matter, a Kras G12D-driven lung cancer mouse model was chosen to address these questions. KRAS protein is a GTPase and is one of the frequently mutated oncoproteins in various cancers. Approximately 25% of lung cancer patients are carriers for mutated KRAS, which has the substitution of Glycine at codon 12 that leads GTPase to remain constantly activated. KRAS mutations have been regarded as the initiating genetic event during tumorigenesis and its activation can increase cell proliferation, survival, and induce metabolic rewiring in cancer cells.

In lung cancer, KRAS activation can transcriptionally up-regulate NRF2, the antioxidant response transcription factor, to deal with oxidative stress and re-program the intermediary metabolism (Cancer Res; 74:24; 7430-41, 2014). On the other hand, the loss of LKB1, the activator of AMPK, frequently occurs simultaneously followed by KRAS mutation, which directly alters energy metabolism in lung cancer (Cancer Res; 79:13; 3251-67, 2019). As for the immune system and microenvironment; low B cell infiltration has been found in mutated KRAS-driven lung cancer, which might influence the immunotherapeutic strategies (Cancers; 11:8; 1145, 2019). To date, the efficient anti-cancer drugs against mutant KRAS-driven cancers is lacking due to the multiple roles of KRAS in maintaining cancer cell viability and which regulatory mechanisms are still elusive.

Thus, there still exists an unmet need for new strategies for treating brain cancers, such as malignant gliomas, and other serious cancers, such as lung cancer, which can provide sustained drug release, high tissue penetration, low morbidity, and introduce effective mechanisms to overcome multidrug resistance and improved outcome/survival for brain tumor and lung cancer patients.

As previously described in the literature, IL-21 is produced by NKT or CD4(+) T cells and has pleiotropic effects on both innate and adaptive immune responses including increasing the cytotoxicity of CD8(+) T cells, or the natural killer (NK) cells, and increasing the differentiation of B cells into plasma cells. In addition, follicular helper T (Tfh) and T helper 17 (Th17) cells also express IL-21 as an autocrine cytokine. Nude mice, however, are deficient for these thymus-derived T-cells.

In some embodiments, the presently disclosed subject matter demonstrates that in LN229 xenograft nude mice (a glioblastoma multiforme (GBM) tumor model), even in the absence of CD4(+) T cells, $M_4N$ (the NDGA derivative, tetra-methyl NDGA, Terameprocol) in low concentrations and in the presently disclosed formulations, which result in plasma or tissue concentrations below 1.5 nM, facilitate the expression of IL-21 through the STAT3/Blimp-1 pathway by targeting glucocorticoid receptor (GR). The concentration of $M_4N$ in plasma or tissue is at about 20 nM, which significantly facilitates the expression of IL-21 without any cytotoxicity.

In some embodiments, the presently disclosed subject matter demonstrates that at low concentrations, $M_4N$ is able to trigger class switch and somatic hypermutation of B cells to raise the quality of anti-tumor antibodies. Thus, $M_4N$ is a potent immunomodulator in LN229 xenograft nude mice model.

Further, in some embodiments, the presently disclosed subject matter demonstrates that $M_4N$ also is a potent immunomodulator in a KRAS G12D mutant mice lung and thymus cancer model. In fact, $M_4N$ in the presently disclosed formulations, was shown to boost the anti-tumor activity of TMZ not only through its cytotoxic activity, but from also activating host humoral immunity. Administration of $M_4N$ with TMZ enhances the titers of specific antitumor antibodies in the sera and promotes the antibody-dependent cell-mediated cytotoxicity of NK cells to suppress tumor growth. See, for example, Table 1, Table 2 and FIG. 1.

As stated in the literature, IL-21 is produced by NKT or CD4(+) T cells and has pleiotropic effects on both innate and adaptive immune responses including to increase cytotoxicity of CD8(+) T cells and natural killer (NK) cells, as well as the differentiation of B cells into plasma cells.

In addition, follicular helper T (Tfh) and T helper 17 (Th17) cells also express IL-21 as an autocrine cytokine. Nude mice, however, are deficient for these thymus-derived T-cells. Therefore, the presently disclosed subject matter demonstrates that $M_4N$-induced humoral anti-tumor immunity cannot be through such thymus-derived T-cells which mediate adaptive immunity. In the absence of CD4(+)T cells, $M_4N$ still can trigger the class switch and somatic hypermutation of B cells to raise the quality of anti-tumor antibodies.

Therefore, the presently disclosed subject matter demonstrates that the immunomodulative effects of $M_4N$ can be considered to be a potent immunomodulator for clinical therapy of cancer patients, especially when the immunities of cancer patients are suppressed after chemotherapeutic treatments or in the situation where tumor cells may also overexpress certain molecules for immuno-check points such as PD-L1 to suppress T-cell mediated immunity.

A. Compositions

In some embodiments, the presently disclosed subject matter provides compositions comprising an effective amount of temozolomide and an effective amount of an NDGA derivative dissolved or suspended in a formulation comprising at least one hydrophobic non-aqueous media and at least one hydrophilic non-aqueous media.

More particularly, in some embodiments, the presently disclosed subject matter provides a composition comprising an effective amount of a derivative of nordihydroguaiaretic acid (NDGA) of formula I:

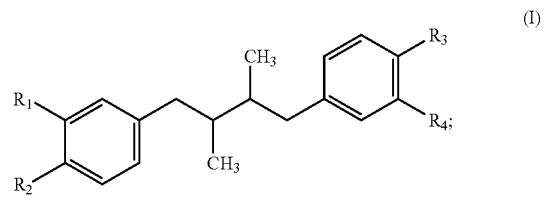

wherein $R_1$, $R_2$, $R_3$, and $R_4$ are each independently selected from the group consisting of straight-chain or branched lower alkyl, hydroxyl, alkoxyl, an amino acid residue, a substituted amino acid residue, a nitrogen-containing 5- or 6-membered heterocyclic ring or a saccharide residue; the amino acid residue, substituted amino acid residue, nitrogen-containing 5- or 6-membered heterocyclic ring or saccharide residue being optionally joined to the phenyl ring of the NDGA derivative by a linker of an oxygen atom and from 1 to 10 carbon atoms, including 1, 2, 3, 4, 5, 6, 7, 8, 9, and 10 carbon atoms; and an effective amount of temozolomide (TMZ) dissolved or suspended in a formulation comprising at least one hydrophobic non-aqueous media and at least one hydrophilic non-aqueous media.

As used herein, the term "dissolved" or "suspended" has its ordinary meaning, for example, it can mean the NDGA derivatives and TMZ may be dissolved or suspended in a volume of liquid comprising combinations of hydrophobic non-aqueous media and hydrophobic non-aqueous media, as well as aqueous media.

It will be understood by those of ordinary skill in the art that temozolomide is approved for use by the U.S. Food and Drug Administration for anaplastic astrocytoma, and glioblastoma multiforme. TMZ (3,4-dihydro-3-methyl-4-oxo-imidazo[5,1-d]-1,2,3,5-tetrazine-8-carboxamide) is a triazene analog of dacarbazine with antineoplastic activity. As a cytotoxic alkylating agent, temozolomide is converted at physiologic pH to the short-lived active compound, monomethyl triazeno imidazole carboxamide (MTIC). The cytotoxicity of MTIC is due primarily to methylation of DNA at the 06 and N7 positions of guanine, resulting in inhibition of DNA replication. Unlike dacarbazine, which is metabolized to MTIC only in the liver, temozolomide is metabolized to MTIC at all sites. Temozolomide is administered orally and penetrates well into the central nervous system.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

In particular embodiments, $C_1$-$C_4$ alkyl includes methyl, ethyl, n-propyl, isopropyl, n-butyl, isobutyl, sec-butyl, and tert-butyl.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Heterocyclic rings include those having from one to three nitrogen heteroatoms, in which the nitrogen heteroatoms may optionally be oxidized and the nitrogen heteroatom may optionally be quaternized. In certain embodiments, the term heterocylic refers to a non-aromatic 5- or 6-membered ring or a polycyclic group wherein at least one ring atom is a nitrogen heteroatom (wherein the nitrogen heteroatom may be optionally oxidized), including, but not limited to, a bi- or tri-cyclic group, comprising fused six-membered rings having between one and three nitrogen heteroatoms, wherein (i) each 5-membered ring has 0 to 2 double bonds, each 6-membered ring has 0 to 2 double bonds, (ii) the nitrogen heteroatom may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, and the like.

As used herein, the term "saccharide residue," includes a monosaccharide residue, which is the divalent organic group that is one constituent monosaccharide unit of an oligo- or poly-saccharide, formed by loss the anomeric hydroxy group and of H from one of the remaining hydroxy groups.

As used herein, the term "amino acid" includes moieties having a carboxylic acid group and an amino group. The term amino acid thus includes both natural amino acids (including proteinogenic amino acids) and non-natural amino acids. The term "natural amino acid" also includes other amino acids that can be incorporated into proteins during translation (including pyrrolysine and selenocysteine).

Additionally, the term "natural amino acid" also includes other amino acids, which are formed during intermediary metabolism, e.g., ornithine generated from arginine in the urea cycle. The natural amino acids are summarized below:

| Amino acid | 3 letter code | 1-letter code |
| --- | --- | --- |
| Alanine | ALA | A |
| Cysteine | CYS | C |
| Aspartic Acid | ASP | D |
| Glutamic Acid | GLU | E |
| Phenylalanine | PHE | F |
| Glycine | PHE | G |
| Histidine | GLY | H |
| isoleucine | HIS | I |
| Isoleucine | ILE | J |
| Lysine | LYS | K |
| Leucine | LEU | L |

-continued

| Amino acid | 3 letter code | 1-letter code |
| --- | --- | --- |
| Methionine | MET | M |
| Asparagine | ASN | N |
| Proline | PRO | P |
| Glutamine | GLN | Q |
| Arginine | ARG | R |
| Serine | SER | S |
| Threonine | THR | T |
| Valine | VAL | V |
| Tryptophan | TRP | W |
| Tyrosine | TYR | Y |

The natural or non-natural amino acid may be optionally substituted. In one embodiment, the amino acid is selected from proteinogenic amino acids.

Proteinogenic amino acids include gly cine, alanine, valine, leucine, isoleucine, aspartic acid, glutamic acid, serine, threonine, glutamine, asparagine, arginine, lysine, proline, phenylalanine, tyrosine, tryptophan, cysteine, methionine and histidine. The term amino acid includes alpha amino acids and beta amino acids, such as, but not limited to, beta alanine and 2-methyl beta alanine. The term amino acid also includes certain lactam analogues of natural amino acids, such as, but not limited to, pyroglutamine. The term amino acid also includes amino acids homologues including homocitrulline, homoarginine, homoserine, homotyrosine, homoproline and homophenylalanine.

The terminal portion of the amino acid residue or peptide may be in the form of the free acid i.e., terminating in a —COOH group or may be in a masked (protected) form, such as in the form of a carboxylate ester or carboxamide. In certain embodiments, the amino acid or peptide residue terminates with an amino group. In an embodiment, the residue terminates with a carboxylic acid group —COOH or an amino group —$NH_2$. In another embodiment, the residue terminates with a carboxamide group. In yet another embodiment, the residue terminates with a carboxylate ester.

As disclosed hereinabove, the term "amino acid" includes compounds having a —COOH group and an —$NH_2$ group. A substituted amino acid includes an amino acid which has an amino group which is mono- or di-substituted. In particular embodiments, the amino group may be mono-substituted. (A proteinogenic amino acid may be substituted at another site from its amino group to form an amino acid which is a substituted proteinogenic amino acid). The term substituted amino acid thus includes N-substituted metabolites of the natural amino acids including, but not limited to, N-acetyl cysteine, N-acetyl serine, and N-acetyl threonine.

For example, the term "N-substituted amino acid" includes N-alkyl amino acids (e.g., $C_{1-6}$ N-alkyl amino acids, such as sarcosine, N-methyl-alanine, N-methyl-glutamic acid and N-tert-butylglycine), which can include $C_{1-6}$ N-substituted alkyl amino acids (e.g., N-(carboxy alkyl) amino acids (e.g., N-(carboxymethyl)amino acids) and N-methylcycloalkyl amino acids (e.g., N-methylcyclopropyl amino acids)); N,N-di-alkyl amino acids (e.g., N,N-di-$C_{1-6}$ alkyl amino acids (e.g., N,N-dimethyl amino acid)); N,N,N-tri-alkyl amino acids (e.g., N,N,N-tri-$C_{1-6}$ alkyl amino acids (e.g., N,N,N-trimethyl amino acid)); N-acyl amino acids (e.g., $C_{1-6}$ N-acyl amino acid); N-aryl amino acids (e.g., N-phenyl amino acids, such as N-phenylglycine); N-amidinyl amino acids (e.g., an N-amidine amino acid, i.e., an amino acid in which an amine group is replaced by a guanidino group).

The term "amino acid" also includes amino acid alkyl esters (e.g., amino acid $C_{1-6}$ alkyl esters); and amino acid aryl esters (e.g., amino acid phenyl esters). For amino acids having a hydroxy group present on the side chain, the term "amino acid" also includes O-alkyl amino acids (e.g., $C_{1-6}$ O-alkyl amino acid ethers); O-aryl amino acids (e.g., O-phenyl amino acid ethers); O-acyl amino acid esters; and O-carbamoyl amino acids.

For amino acids having a thiol group present on the side chain, the term "amino acid" also includes S-alkyl amino acids (e.g., $C_{1-6}$ S-alkyl amino acids, such as S-methyl methionine, which can include $C_{1-6}$ S-substituted alkyl amino acids and S-methylcycloalkyl amino acids (e.g., S-methylcyclopropyl amino acids)); S-acyl amino acids (e.g., a $C_{1-6}$ S-acyl amino acid); S-aryl amino acid (e.g., a S-phenyl amino acid); a sulfoxide analogue of a sulfur-containing amino acid (e.g., methionine sulfoxide) or a sulfoxide analogue of an S-alkyl amino acid (e.g., S-methyl cysteine sulfoxide) or an S-aryl amino acid.

In other words, the presently disclosed subject matter also envisages derivatives of natural amino acids, such as those mentioned above which have been functionalized by simple synthetic transformations known in the art (e.g., as described in "Protective Groups in Organic Synthesis" by T W Greene and P G M Wuts, John Wiley & Sons Inc. (1999)), and references therein.

Examples of non-proteinogenic amino acids include, but are not limited to: citrulline, hydroxyproline, 4-hydroxyproline, β-hydroxyvaline, ornithine, β-amino alanine, albizziin, 4-amino-phenylalanine, biphenylalanine, 4-nitro-phenylalanine, 4-fluoro-phenylalanine, 2,3,4,5,6-pentafluoro-phenylalanine, norleucine, cyclohexylalanine, α-aminoisobutyric acid, α-aminobutyric acid, α-aminoisobutyric acid. 2-aminoisobutyric acid, 2-aminoindane-2-carboxylic acid, selenomethionine, lanthionine, dehydroalanine, γ-amino butyric acid, naphthylalanine, aminohexanoic acid, pipecolic acid, 2,3-diaminoproprionic acid, tetrahydroisoquinoline-3-carboxylic acid, tert-leucine, tert-butylalanine, cyclopropylglycine, cyclohexylglycine, 4-aminopiperidine-4-carboxylic acid, diethylglycine, dipropylglycine and derivatives thereof wherein the amine nitrogen has been mono- or di-alkylated.

In some embodiments, the NDGA derivative is tetra-o-methyl nordihydroguaiaretic acid ($M_4N$) or maltose-$M_3N$.

In some embodiments, the NDGA derivative has the following formula:

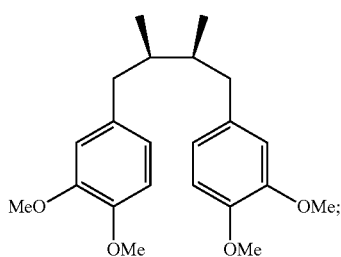

(II)

or a salt, solvate, or stereoisomer thereof.

In some embodiments, the derivative of NDGA used in the presently disclosed methods includes embodiments wherein $R_1$, $R_2$, $R_3$, and $R_4$ are each 2-(piperidino)ethoxyphenyl groups. In such embodiments, the NDGA derivative is $P_4N$ (tetrapiperidino NDGA, meso-2,3-dimethyl-1,4-bis (3,4-[2-(piperidino)ethoxyphenyl])butane tetrakishydrochloride salt) having the following formula:

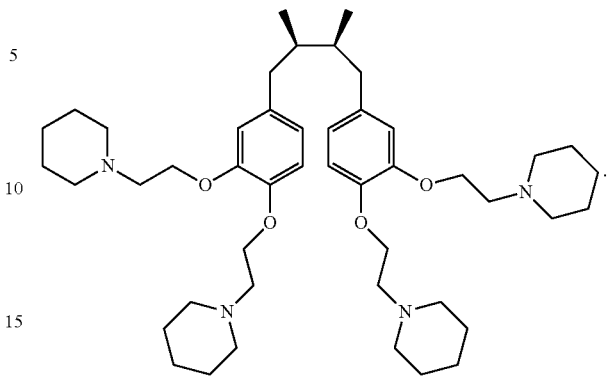

($P_4N$)

The synthesis of $P_4N$ is detailed in U.S. Pat. No. 7,741,357, issued Jun. 22, 2010, which is incorporated herein by reference in its entirety.

In some embodiments, the amount of temozolomide in the composition is between about 50 mg/m² to about 200 mg/m², including about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, and 200 mg/m² orally.

In some embodiments, the dosage of the NDGA derivative is between about 0.1 mg/kg to about 10 mg/kg, including about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, and 10 mg/kg.

In some embodiments, the concentration of the NDGA derivative is between about 0.01 µM to about 50 µM, including about 0.01, 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 µM.

In some embodiments, the dosage of the NDGA derivative is between about 100 mg/kg to about 1000 mg/kg, including about 100, 150, 200, 250, 300, 350, 400, 450, 500, 550, 600, 650, 700, 750, 800, 850, 900, 950, and 1000 mg/kg, or between about 300 mg/kg to about 600 mg/kg, including 300, 325, 350, 375, 400, 425, 450, 475, 500, 525, 550, 575, and 600 mg/kg.

In one embodiment, the concentration of the NDGA derivative, $M_4N$ is between about 303 mg/kg (about 6.06 mg per 20 g of mouse body weight) to about 606 mg/kg (about 12.12 mg per 20 g of mouse body weight).

As used herein, the pharmaceutical compositions described herein comprise a combination of hydrophobic non-aqueous media and hydrophobic non-aqueous media. It will be understood by those of skill in the art that the combinations of hydrophobic non-aqueous media and hydrophobic non-aqueous media can also include aqueous solutions.

As used herein, the term "hydrophobic non-aqueous media" includes a media predominantly comprising oil, that is to say an edible animal, vegetable or mineral oil; it can be solid or liquid at ambient temperature; however, preference is given to oils which are liquid from 15° C. Use may be made, among vegetable oils, of soybean oil, coconut oil, palm oil, sunflower oil or their mixture. See, for example, Methods and Composition for Treatment of Intraepithelial Neoplasia, U.S. Pat. No. 8,440,648, which is incorporated herein by reference in its entirety.

In some embodiments, a lipid solution of short and medium chain fatty acids may be used. The fatty acids having 14 or fewer carbon atoms, including 14, 13, 12, 11, 10, 9, 8, 7, 6, 5, or 4 carbons, in the backbone are generally referred to as short chain and medium chain fatty acids. Non-limiting examples include caproic acid, heptanoic acid, caprylic acid, nonanoic acid and capric acid, and these fatty acids can also be modified or derived, as in Miglyol® products (SASOL), which are esters derived from fatty acid, which is found, for example, in palm oil or coconut oil, coupled with glycerol or propylene glycol; the oil of animal origin can be chosen from fish oils or cod liver oil and the mineral oil can be paraffin oil. In particular embodiments, the hydrophobic non-aqueous media is a Miglyol. In more particular embodiments, the hydrophobic non-aqueous media comprises Miglyol 812N.

In some embodiments, the hydrophobic non-aqueous media are selected from the group consisting of refined specialty oils such as arachis oil, castor oil, cottonseed oil, maize (corn) oil, olive oil, sesame oil, soybean oil and sunflower oil; medium-chain triglycerides and related esters such as caprylic/capric triglycerides (Akomed E, Akomed R, Miglyol 810, and Captex 355), medium-chain triglyceride (Labrafac CC), propylene glycol diester of caprylic/capric acid (Labrafac PG), propylene glycol monolaurate (Lauroglycol FCC), fractionated coconut oil (Miglyol 812), caprylic/capric/diglyceryl succinate (Miglyol 829), medium-chain diesters of propylene glycols (Miglyol 840), partial ester of diglycerides with natural fatty acids (Softisan 645), and medium-chain mono- and diglycerides (Akoline MCM and Capmul MCM).

As used herein, the term "hydrophilic non aqueous media" means a solubilizer compound which includes, but is not limited to, hydrophilic surfactants or lipophilic surfactants or mixtures thereof. The surfactants may be anionic, nonionic, cationic, and zwitterionic surfactants.

In some embodiments, the hydrophilic non aqueous media are selected from the group consisting of: linoleoyl macrogolglycerides (Labrafil M 2125 CS), PEG-8 caprylic/capric glycerides (Labrasol), lauric acid, propylene glycol laurate (Lauroglycol 90), oleic acid, PEG MW>4000, polyglycerol dioleate (Plurol Oleique CC 497), polyoxyethylene-polyoxypropylene copolymer (Poloxamer 124 and 188), partial glycerides of hydroxylated unsaturated fatty acids (Softigen 701), PEG-6 caprylic/capric glycerides (Softigen 767), polyoxyethylene glyceryl trioleate (Tagat TO), polyoxyethylene(20)sorbitan monooleate (Tween 80), D-α-tocopheryl polyethylene glycol succinate (Vitamin E TPGS), hydrogenated polyoxyl castor oil (Cremophor EL), glycerin (with a content>5%), glycofurol 75, PEG MW<4000, N-methyl-2-pyrrollidone (Pharmasolve), propylene glycol, sorbitan monooleate (Span 80), and diethylene glycol monoethylether (Transcutol P). In particular embodiments, the hydrophilic non-aqueous media is Vitamin E TPGS.

In some embodiments, the presently disclosed subject matter provides the compositions comprising NDGA derivatives and TMZ and at least one additional therapeutic agent.

It will be understood to those of skill in the art that the term "therapeutic agent" is any agent capable of affecting the structure or function of the body of a subject or is an agent useful for the treatment or modulation of a disease or condition in a subject suffering therefrom. Examples of therapeutic agents can include any drugs known in the art for treatment of disease indications.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the presently disclosed subject matter includes the active agent per se, as well as pharmaceutically acceptable, pharmacologically active salts, esters, amides, prodrugs, metabolites, analogs, and the like.

In a further embodiment, the presently disclosed compositions and methods can be used in combination with one or more additional therapeutically active agents which, are known to be capable of treating conditions or diseases discussed above. For example, the presently disclosed compositions could be used in combination with one or more known therapeutically active agents, to treat a proliferative disease, such as a tumor or cancer. Non-limiting examples of other therapeutically active agents that can be readily combined in a pharmaceutical composition with the presently disclosed compositions and methods are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

As used herein, therapeutically active agents encompass "chemotherapeutic agents" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids. Further examples of chemotherapeutic agents include asparaginase, busulfan, carboplatin, cisplatin, daunorubicin, doxorubicin, fluorouracil, gemcitabine, hydroxyurea, methotrexate, paclitaxel, rituximab, vinblastine, vincristine, and the like.

Examples of other active agents which can be used in the inventive compositions and methods are one or more immune checkpoint blockers. The immune checkpoint blockers can be an antibody which can be the same or different and selected from the group consisting of anti-CTLA-4, anti-B7-H4, anti-B7-H1, anti-LAG3 and anti-PD1 antibodies.

In some embodiments, the PD-1 inhibitors are anti-PD1 antibodies which can be the same or different and selected from the group consisting of pembrolizumab, nivolumab, cemiplimab, avelumab, durvalumab, atezolizumab, spartalizumab (PDR001), camrelizumab (SHR1210), sintilimab (IBI308), tislelizumab (BGB-A317), toripalimab (JS 001), MPDL3280A, MEDI4736, AMP-224, AMP-514, and MSB0010718C.

In some embodiments, the anti-CTLA-4 antibodies which can be the same or different and selected from the group consisting of ipilimumab (MDX-010), L3D10, tremelimumab (CP-675,206), and 9H10.

The term "combination" is used in its broadest sense and means that a subject is administered at least two agents, more particularly a composition of formula (I) or formula (II) and at least one additional therapeutic agent. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compositions of formula (I) or formula (II) described herein can be administered alone or in combination with adjuvants that enhance stability of the compositions of formula (I) or formula (II), alone or in combination with one or more agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compositions of formula (I) or formula (II) and at least one additional therapeutic agent can be varied so long as the beneficial effects of the combination of these agents are achieved. Accordingly, the phrase "in combination with" refers to the administration of a composition of formula (I) or formula (II) and at least one additional therapeutic agent either simultaneously, sequentially, or a combination thereof. Therefore, a subject administered a combination of a composition of formula (I) or formula (II) and at least one additional therapeutic agent can receive composition of formula (I) or formula (II) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the composition of formula (I) or formula (II) and at least one additional therapeutic agent are administered simultaneously, they can be administered to the subject as separate pharmaceutical compositions, each comprising either a composition of formula (I) or formula (II) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a composition of formula (I) or formula (II) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

The presently disclosed compositions can comprise various pharmaceutically acceptable salts, ether derivatives, ester derivatives, acid derivatives, and aqueous solubility altering derivatives of the active compound. The presently disclosed compositions can comprise all individual enantiomers, diastereomers, racemates, and other isomer of compounds of formula (I) or formula (II). The presently disclosed compositions also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Included within the compounds of the presently disclosed subject matter are the tautomeric forms of the disclosed compounds, isomeric forms including diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the presently disclosed compounds include, for example, acid addition salts which may, for example, be formed by mixing a solution of the presently disclosed compounds with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding presently disclosed compounds.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the presently disclosed compounds.

For use in medicines, the salts of the presently disclosed compounds can be pharmaceutically acceptable salts. Other salts may, however, be useful in the preparation of the presently disclosed compounds or of their pharmaceutically acceptable salts.

In addition, embodiments of the presently disclosed compounds include hydrates. The term "hydrate" includes but is not limited to hemihydrate, monohydrate, dihydrate, trihydrate and the like. Hydrates of the presently disclosed compounds may be prepared by contacting the compounds with water under suitable conditions to produce the hydrate of choice.

With respect to the pharmaceutical compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use.

In some embodiments, the presently disclosed subject matter provides a use of the compositions described herein, an amount effective for use in a medicament, and most preferably for use as a medicament for treating a disease or disorder associated with a neoplastic disease in a subject.

B. Methods of Treatment

In some embodiments, the methods of treatment disclosed herein are useful against many mammalian tumors, including, for example, lung cancer, breast cancer, prostate cancer, pancreatic cancer, colon cancer, hepatoma, glioblastoma, ovarian cancer, leukemia, Hodgkin's lymphoma and multiple myeloma.

With regard to the presently disclosed compositions and methods, the term cancer, includes cancers of the CNS and brain, including gliomas, glioblastoma, gliosarcoma, astrocytoma, oligodendroglioma, ependymoma, meningioma, medulloblastoma, ganglioma, Schwannoma, craniopharyngioma, chordomas and pituitary tumors.

With regard to the term lung cancer, the term includes non-small cell lung cancer (NSCLC) where about 80% to 85% of lung cancers are NSCLC. The main subtypes of NSCLC are adenocarcinoma, squamous cell carcinoma, and large cell carcinoma. It also includes small cell lung cancers and other cancers of the lung.

It will be understood by those of ordinary skill in the art that the term "tumor" as used herein means a neoplasia or neoplastic growth which may or may not be malignant. Additionally, the compositions and methods provided herein are not only useful in the treatment of tumors, but in their micrometastses and their macrometastses. Typically, micrometastasis is a form of metastasis (the spread of a cancer from its original location to other sites in the body) in which the newly formed tumors are identified only by histologic examination; micrometastases are detectable by neither physical exam nor imaging techniques. In contrast, macrometastses are usually large secondary tumors.

In some embodiments, the presently disclosed subject matter provides compositions and methods for the prevention and/or treatment of tumors, and their micrometastses and their macrometastses.

Accordingly, in some embodiments, the presently disclosed subject matter provides a method for treating brain cancer in a subject in need thereof, comprising administering to the subject a presently disclosed composition.

In some embodiments, the presently disclosed subject matter provides a method for increasing expression of IL-21 in one or more tissues of a subject, comprising administering to the subject and effective amount of a presently disclosed composition.

In some embodiments, the presently disclosed subject matter provides a method to increase B cell proliferation and differentiation in one or more tissues of a subject, comprising administering to the subject and effective amount of a presently disclosed composition.

In some embodiments, the presently disclosed subject matter provides a method for increasing secretion of anti-tumor immunoglobulins in one or more tissues of a subject having a tumor. In particular embodiments, the anti-tumor immunoglobulins are of the IgA and IgG2a subtypes.

In some embodiments, the presently disclosed subject matter provides a method for increasing expression of anti-tumor immunoglobulins in one or more tissues of a subject, comprising administering to the subject an effective amount of a presently disclosed composition.

The anti-tumor immunoglobulin can be any type of immunoglobulin that is known in the art. For instance, the immunoglobulin can be of any isotype, e.g., IgA, IgD, IgE, IgG, IgM, and the like. The immunoglobulin can be a monoclonal or polyclonal antibody. The antibody can be a naturally-occurring antibody, e.g., an antibody isolated and/or purified from a mammal, e.g., mouse, rabbit, goat, horse, chicken, hamster, human, and the like. As used herein, the term "antibody" means a polypeptide comprising a framework region from an immunoglobulin gene or fragments thereof that specifically binds and recognizes an antigen. Use of the term antibody is meant to include whole antibodies, including single-chain whole antibodies, antibody fragments such as Fab fragments, and other antigen-binding fragments thereof.

In some embodiments, the immunoglobulins are of the IgA and IgG2a subtypes.

The term "antigen" or "antigenic epitope" as used herein refers to any molecule (e.g., protein, peptide, lipid, carbohydrate, etc.) solely or predominantly expressed or over-expressed by a target cell of interest (e.g., a tumor cell), such that the antigen is associated with the target cell.

Methods of testing antibodies for the ability to bind to any functional portion of the tumor antigens are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

In some embodiments, the presently disclosed subject matter provides a method for treating a glioblastoma in a subject in need thereof, comprising administering to the subject a presently disclosed composition.

In some embodiments, the presently disclosed subject matter provides a method for suppressing one or more major reprogrammed metabolic pathways of the tumor including those affecting the TCA cycle, fatty acid synthesis, and fatty acid metabolism in a subject in need thereof, comprising administering to the subject a presently disclosed composition.

It will be understood by those of skill in the cancer art that cancer metabolic reprogramming has been recognized as one of the ten cancer hallmarks by Drs. Hanahan and Weinberg in their seminal review paper published in 2011 (Cell 2011; 144:646-674). Some of the most striking changes of tumor cellular bioenergetics include elevation of glycolysis, increase in glutaminolytic flux, upregulation of amino acid and lipid metabolism, enhancement of mitochondrial biogenesis, induction of pentose phosphate pathway and macromolecule biosynthesis. These cancer metabolic programs provide tumor cells with not only necessary energy but also crucial materials to support large-scale biosynthesis, rapid proliferation, survival, invasion, metastasis and resistance to anti-cancer therapies. Given the vital role of metabolic reprogramming for tumorigenesis, targeting cancer bioenergetics is a very promising and rapidly rising direction for anti-cancer therapy development nowadays. Many compounds have been developed to selectively and effectively inhibit metabolic enzymes that are important for tumors. One of the most common trends in anti-cancer metabolism therapies is to inhibit enzymes that are exclusively or mostly expressed or used in tumor cells. This therapeutic strategy would effectively eliminate tumors while minimizing damage to normal cells.

The dose of the presently disclosed compositions also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated.

As used herein, the terms "effective amount" or "sufficient amount" are equivalent phrases which refer to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease, such as a neoplastic disease or tumor.

The presently disclosed pharmaceutical compositions are useful for prophylaxis or treatment of a condition. Accordingly, the presently disclosed compositions are useful as a drug or as information for structural modification of existing compounds, e.g., by rational drug design.

For therapeutic uses, the compositions or agents identified using the methods disclosed herein may be administered systemically, for example, formulated for oral administration or parenteral administration.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques. Compositions for parenteral use may be provided in unit dosage forms (e.g., in single-dose ampules), or in vials containing several doses and in which a suitable preservative may be added. The composition may be in the form of a solution, a suspension, an emulsion, an infusion device, or a delivery device for implantation or it may be presented as a dry powder to be reconstituted with water or another suitable vehicle before use. The composition may include suitable parenterally acceptable carriers and/or excipients.

The dose of the presently disclosed compositions also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration and are not to be construed as limiting in any manner to make compounds of the disclosure by other methods.

Example 1

Oral Formulations 1.1 EM Oral Formulation

In one exemplary embodiment, approximately 440 mg of a vitamin E component [TPGS NF (D-alpha-Tocopherol Polyethylene glycol (PEG) 1000 succinate, BioXtra, water soluble vitamin E conjugate (MilliporeSigma—SKU: 57668-5G)] was heated to about 50° C. To this mixture was added about 5 mL Miglyol 812 N (IOI Oleo GmbH, Oleochemicals) and stirred for about 15 minutes at room temperature. If solids were noted in the formulation, gentle warming was used (up to approximately 37-40° C.) until complete dissolution.

The EM oral formulation was stored at room temperature. On the day of dosing the control formulation as placed was heated to approximately 37-40° C. and stirred for at least 30 minutes before dosing.

1.2 TMZ in EM Oral Formulation

To the above EM formulation was added either about 2.5 mg (12 dose) or 5 mg (full dose) of TMZ (Millipore Sigma—SKU: T2577-100 mg) in about 5 mL EM oral formulation. The mixture was stirred until completely dissolved. The TMZ in EM oral formulation was stored at room temperature. On the day of dosing the TMZ formulation was heated to about 37-40° C. and stirred for at least about 30 minutes before dosing.

1.3 $M_4N$ in EM Oral Formulation

To the above EM formulation was added about 303 mg/kg of Terameprocol ($M_4N$, Erimos Pharmaceuticals). The $M_4N$ mixture was stirred until completely dissolved. The $M_4N$ in EM oral formulation was stored at room temperature. On the day of dosing the $M_4N$ formulation was heated to about 37-40° C. and stirred for at least about 30 minutes before dosing.

1.4 $M_4N$ Plus TMZ in EM Oral Formulation

To the above EM formulation was added about 303 mg/kg (6.06 mg per 20 g of mouse body weight) of Terameprocol ($M_4N$, Erimos Pharmaceuticals) and either about 2.5 mg/kg (50 μg per 20 g of mouse body weight) of TMZ (2 dose) or 5 mg/kg (100 μg per 20 g of mouse body weight) of TMZ (full dose). The $M_4N$ and TMZ mixture was stirred until completely dissolved. The $M_4N$ and TMZ in EM oral formulation was stored at room temperature. On the day of dosing the $M_4N$ and TMZ formulation was heated to about 37-40° C. and stirred for at least about 30 minutes before dosing.

The formulations stored at room temperature were used within two to three weeks and new mixtures were made as needed.

Example 2

Examination of Control of LN229 Tumor Progression in Xenograft Nude Mice

Three sets of treatment procedures were used:
Set 1—EM formulation alone and EM+$M_4N$ formulation;
Set 2—EM+TMZ formulation and EM+TMZ+$M_4N$ formulation; and
Set 3—EM+$TMZ_{1/2}$ formulation and EM+$M_4N$+$TMZ_{1/2}$ formulation.

The treatment duration for treatment sets 1 and 2 were 35 days, with tumors and sera of treated mice harvested (sera collected from living mice) for analysis 24 hours later. In treatment set 3, the treatment duration was only 25 days, and tumors in xenograft mice were allowed to grow for another 38 days before the collection of tumors/sera at day 63.

The tumor size, drug concentrations in tumors/serums, the level of serum immunoglobulins (IgM, IgG, IgA and IgG subtypes IgG1, IgG2a, IgG2b and IgG3) and the metabolic reprogramming profiles were analyzed in a total 32 tumors (see Table 1 and Table 2). In EM+$M_4N$+$TMZ_{1/2}$ (Set 3), the total stopping of the growth of LN229 tumors was observed even in the absence of drug treatment for the last 38 days (FIG. 3A).

TABLE 1

$M_4N$ (nM) concentration in the blood and tumor of LN229 tumor bearing mice in each treatment group.

| Groug | Sample | Blood | Tumor |
|---|---|---|---|
| Contineus treatment (day 35) | | | |
| EM | | — | — |
| EM + $M_4N$ | | 510 ± 280 | 26.7 ± 10.3 |
| EM + TMZ | | — | — |
| EM + $M_4N$ + TMZ | | 670 ± 350 | 18.8 ± 13.2 |
| After stop treatment at day 25 (day 63) | | | |
| EM + $TMZ_{1/2}$ | | | |
| EM + $M_4N$ + $TMZ_{1/2}$ | | | |

Example 3

Determination of the Presence of Immunoglobulins in Sera of Drug-Treated Mice

Two sets of treatment procedures were used. Each treatment used ten LN229 xenograft mice. The first treatment set was EM+$TMZ_{1/2}$ and the second treatment set was EM+M$_4$N+TMZ$_{1/2}$. In both treatment sets there were immunoglobulins in all ten mice. Compared to EM+TMZ$_{1/2}$, there were increased levels of IgA and IgG2a subtype following EM+M$_4$N+TMZ$_{1/2}$ treatment (FIG. 3B). These results agree with well-known antibody research done in the 1980's, which showed that monoclonal antibodies of the IgG2a isotype could specifically inhibits the growth of human tumors in nude mice.

Figure 1A:
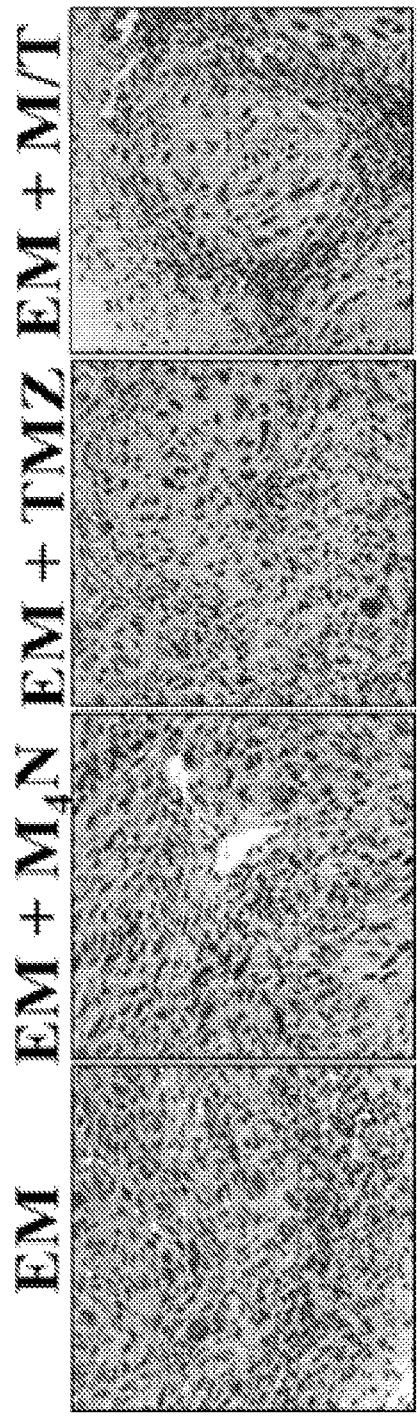
Figure 1B:
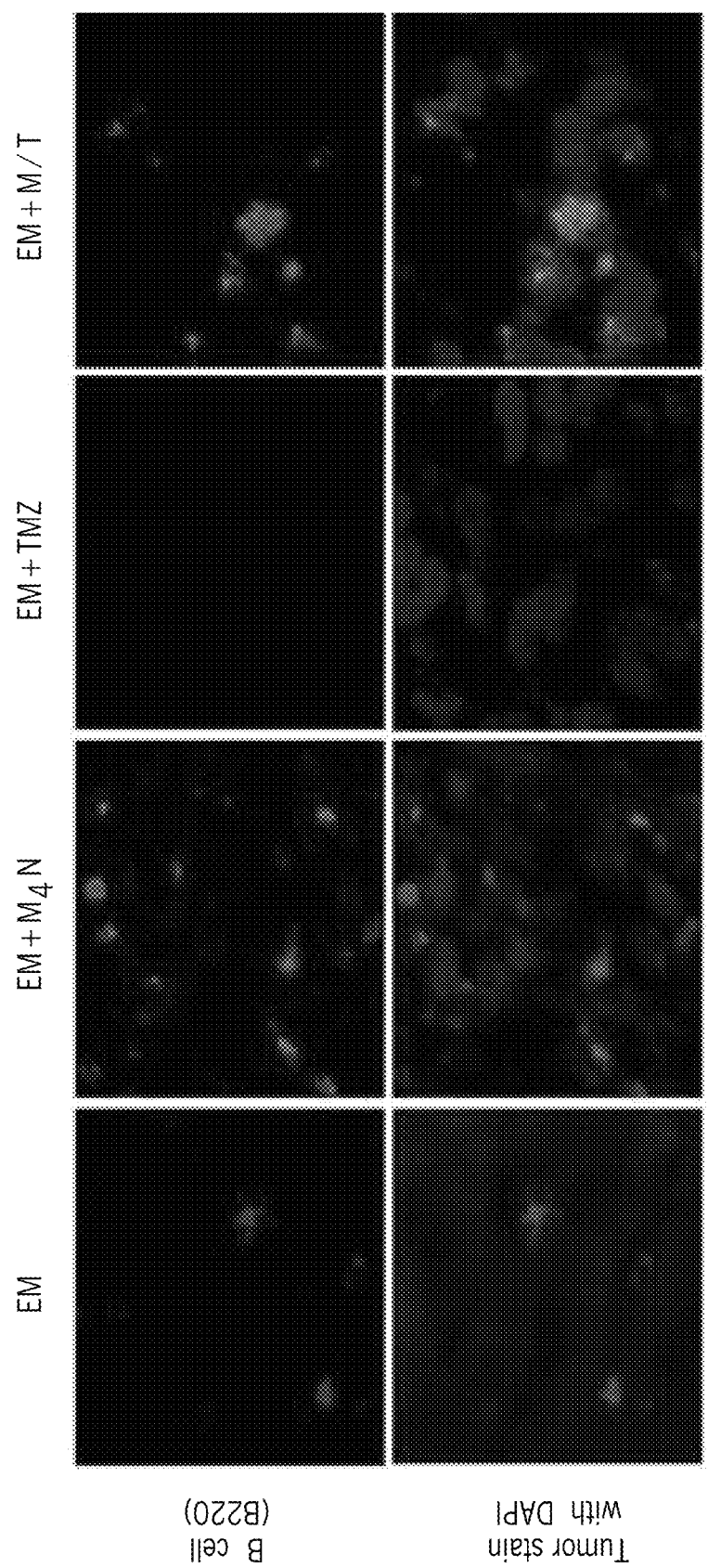
Figure 1C:
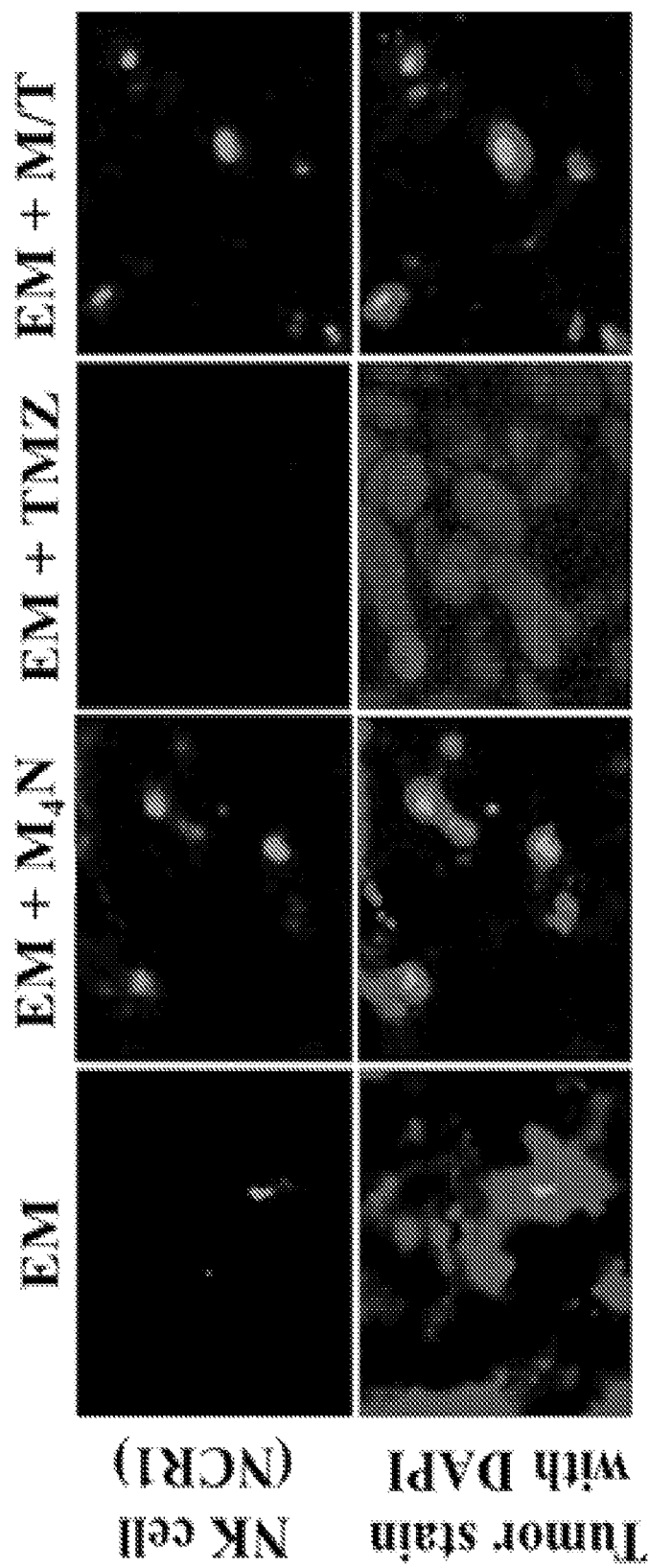
Figure 1D:
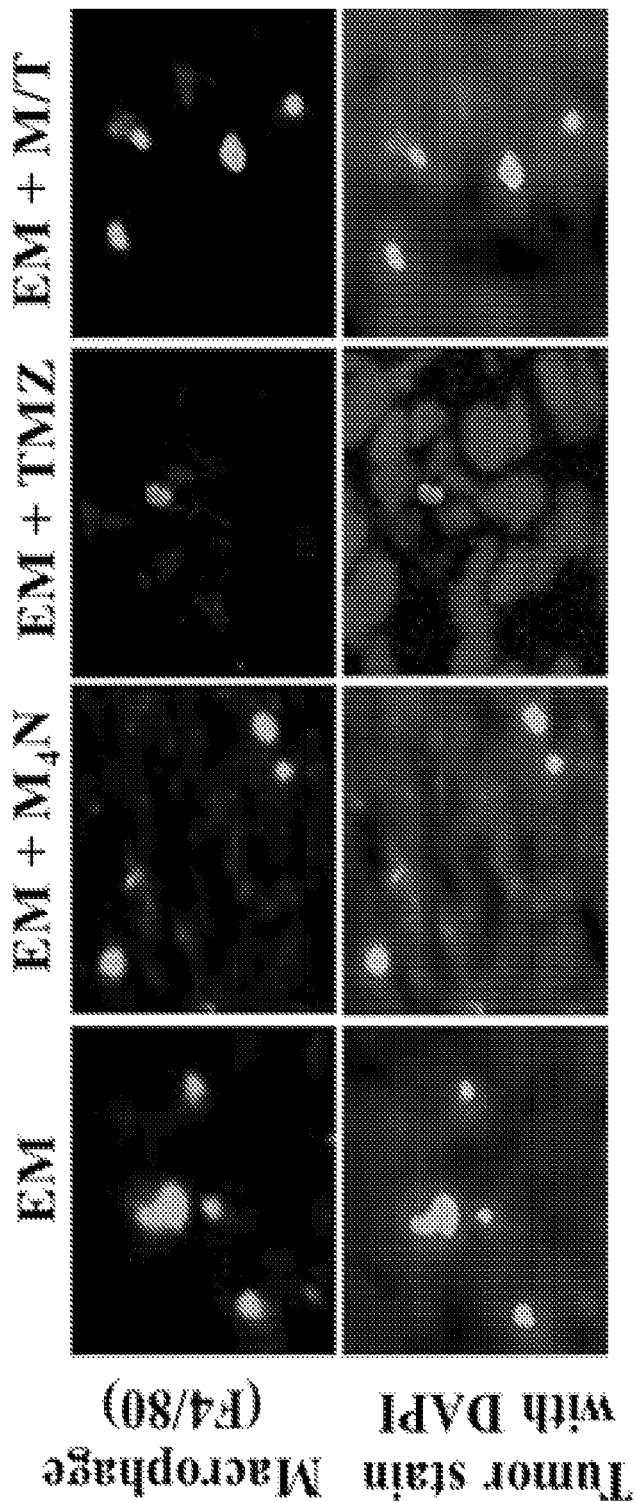
Figure 1E:
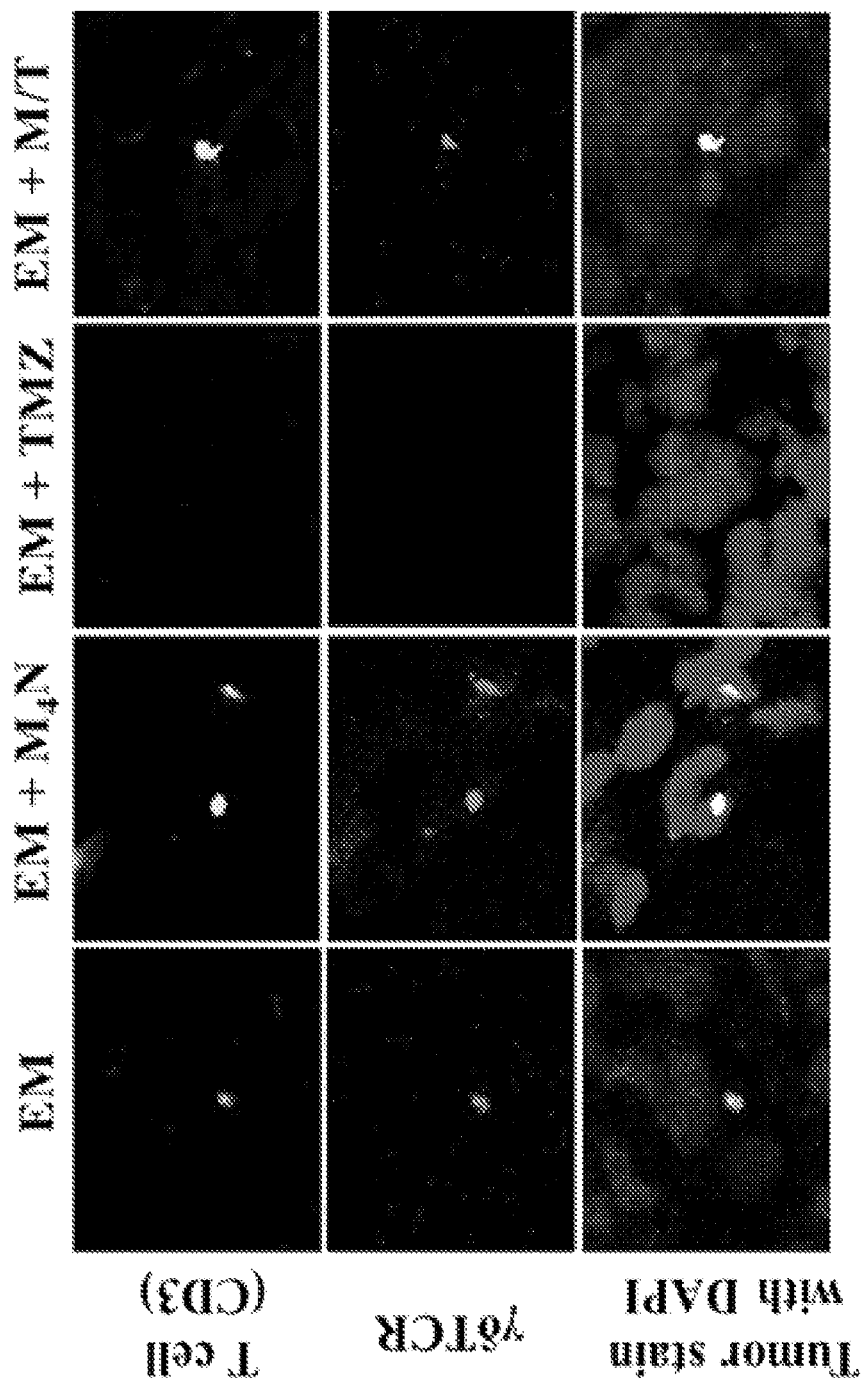
Figure 1F:
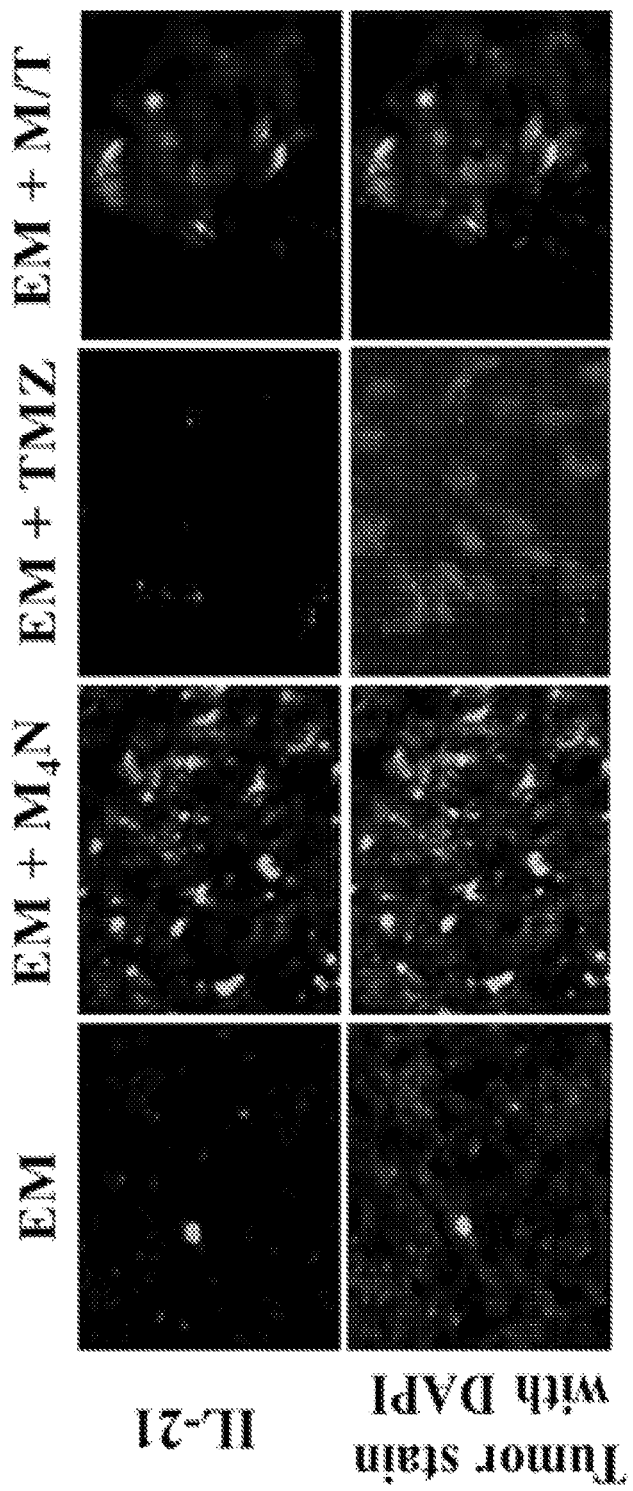

Tumor infiltrating macrophages and B cells, as well as other immune cells (FIG. 1), were observed in the tumor microenvironment from M$_4$N and M$_4$N/TMZ combination treatments attacking LN229 tumors (FIG. 1B, FIG. 1D and FIG. 1E). Results of the examination of cytokine profiles of sera from LN229 tumor xenograft mice showed that the level of IL-21 was significantly increased after M$_4$N or M$_4$N/TMZ treatment.

Figure 1G:
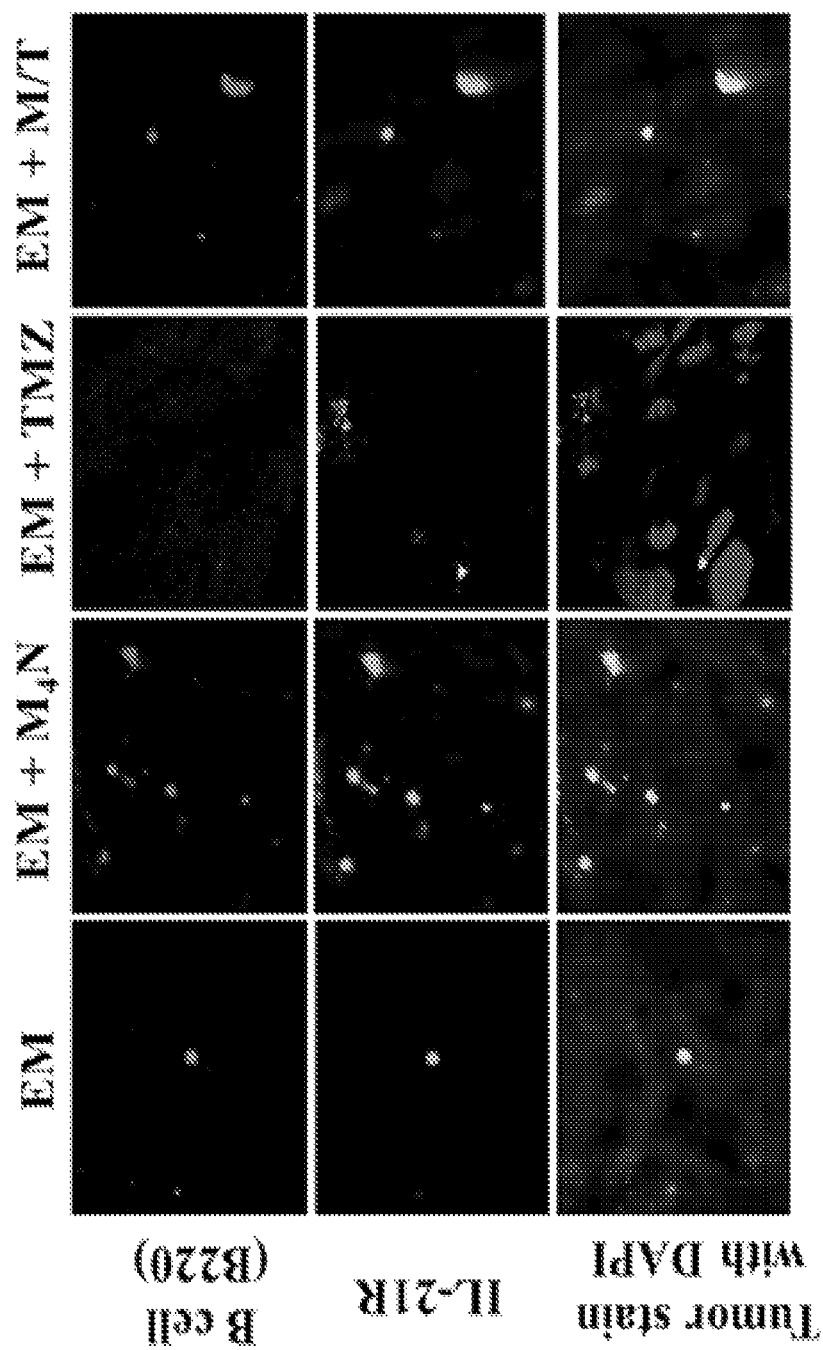
Figure 1H:
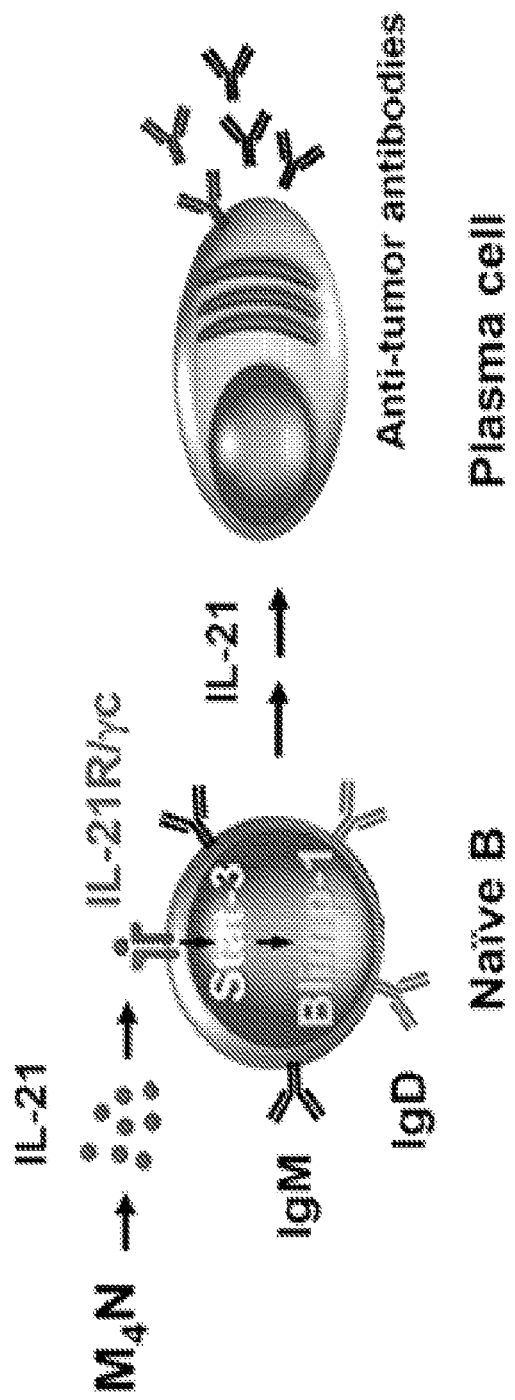
Figure 1I:
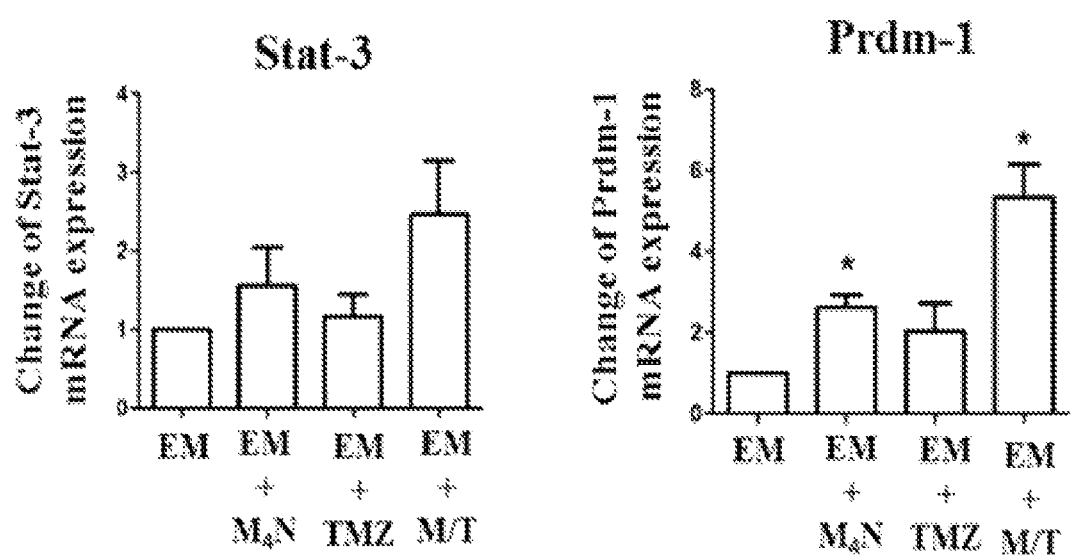
Figure 1J:
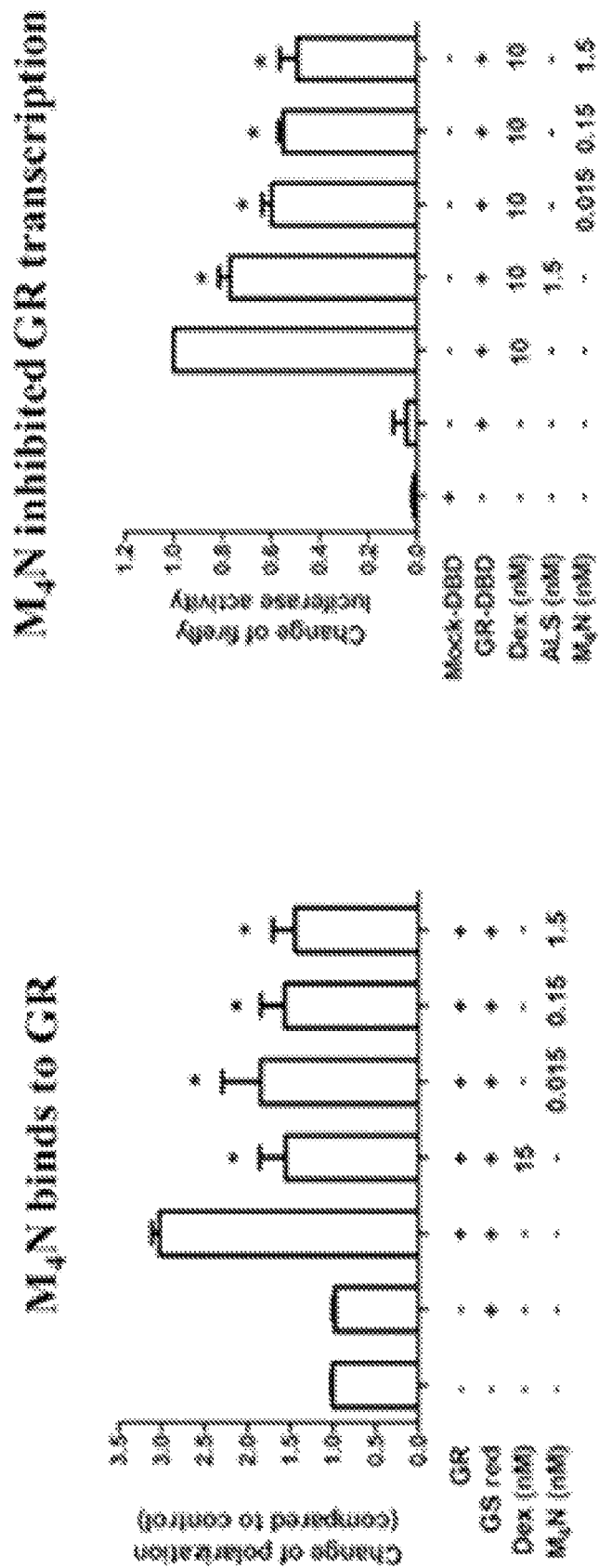

In the tumors, it was found that EM+M$_4$N or EM+M$_4$N+TMZ treatment enhanced the expression levels of IL-21 in the tumor of LN229 xenograft mice. In both sera and tumor it showed that IL-21 was a mediator to regulate B cell proliferation and differentiation. The M$_4$N-induced tumor infiltration of B cells also expresses IL-21 receptor (FIG. 1G). The activation of IL-21/IL-21R/STAT3 signaling pathway in primary human B cells induced BLIMP-1 expression to initiate B cell differentiation and enhanced the secretion of immunoglobulins. After treatment with EM+M$_4$N or EM+M$_4$N+TMZ, the mRNA expression of STAT3 and PRDM-1 also were increased. Therefore, EM+M$_4$N stimulated IL-21 release and activated STAT3/BLIMP-1 signaling to increase B cell proliferation, differentiation and immunoglobulin production (FIG. 1, Table 2).

TABLE 2

Cytokine profiles in serum in EM, EM + M$_4$N, EM + TMZ or EM + M$_4$N + TMZ treated nude mice.

| Cytokines and chemokines | EM | EM + M$_4$N | EM + TMZ | EM + M$_4$N + TMZ |
|---|---|---|---|---|
| IL-1β | 147.4 ± 33.5 | 146.5 ± 15.2 | 104.4 ± 40.5 | 122.9 ± 43.8 |
| IL-2 | 57.8 ± 33.3 | 53.2 ± 7.9 | 30.2 ± 16.5 | 37.5 ± 23.3 |
| IL-3 | 69.9 ± 18.1 | 52.3 ± 8.0 | 38.7 ± 15.6 | 48.6 ± 25.7 |
| IL-4 | 51.4 ± 15.7 | 45.5 ± 6.9 | 34.5 ± 11.0 | 37.7 ± 15.5 |
| IL-5 | 72.2 ± 38.6 | 46.5 ± 11.1 | 13.5 ± 12.6 | 54.2 ± 32.7 |
| IL-6 | 26.1 ± 17.6 | 20.1 ± 5.7 | 14.9 ± 10.2 | 15.6 ± 6.9 |
| IL-9 | 181.2 ± 46.5 | 165.8 ± 15.9 | 126.3 ± 31.7 | 146.9 ± 61.1 |
| IL-10 | 154.6 ± 50.4 | 141.9 ± 24.9 | 109.0 ± 50.0 | 110.8 ± 57.5 |
| IL-12 (p40) | 326.4 ± 87.1 | 262.3 ± 50.7 | 368.0 ± 105.2 | 329.1 ± 100.6 |
| IL-12 (p70) | 382.5 ± 101.8 | 314.9 ± 200.3 | 190.0 ± 122.0 | 323.4 ± 115.0 |
| IL-13 | 228.1 ± 154.5 | 281.8 ± 171.1 | 155.6 ± 67.9 | 151.6 ± 40.1 |
| IL-17 | 148.9 ± 44.4 | 105.7 ± 47.3 | 126.5 ± 46.9 | 103.6 ± 40.4 |
| IL-21 | 139.3 ± 25.9 | 209.2 ± 37.2 | 144.9 ± 71.6 | 291.1 ± 67.4 |
| Eotaxin | 986.2 ± 219.6 | 783.5 ± 168.3 | 1159.4 ± 431.5 | 1185.8 ± 381.1 |
| G-CSF | 190.9 ± 42.3 | 152.9 ± 37.5 | 123.1 ± 19.7 | 134.3 ± 47.1 |
| GM-CSF | 104.9 ± 53.3 | 95.6 ± 21.7 | 59.6 ± 30.5 | 91.7 ± 30.0 |
| IFN-γ | 91.2 ± 28.0 | 87.0 ± 22.9 | 65.2 ± 30.9 | 82.7 ± 45.3 |
| KC | 90.2 ± 26.6 | 75.2 ± 19.9 | 78.8 ± 32.2 | 64.9 ± 17.9 |
| MCP-1 | 367.2 ± 140.7 | 370.4 ± 78.5 | 207.5 ± 101.2 | 315.1 ± 72.7 |
| MIP-1α | 11.7 ± 4.8 | 11.9 ± 1.9 | 59 ± 50 | 9.9 ± 7.2 |
| MIP-1β | 134.0 ± 73.8 | 110.6 ± 28.3 | 74.7 ± 37.4 | 91.3 ± 32.5 |
| RANTES | 12.1 ± 3.1 | 7.57 ± 5.2 | 13.6 ± 3.6 | 11.3 ± 8.7 |
| TNF-α | 1054.3 ± 4445.8 | 828.3 ± 273.0 | 751.1 ± 362.5 | 829.8 ± 291.5 |

All values are mean ± SD of five mouse in each group (n = 5).

Example 4

Identification of Metabolite Changes in LN229 Tumors During Treatment

Figure 6B:
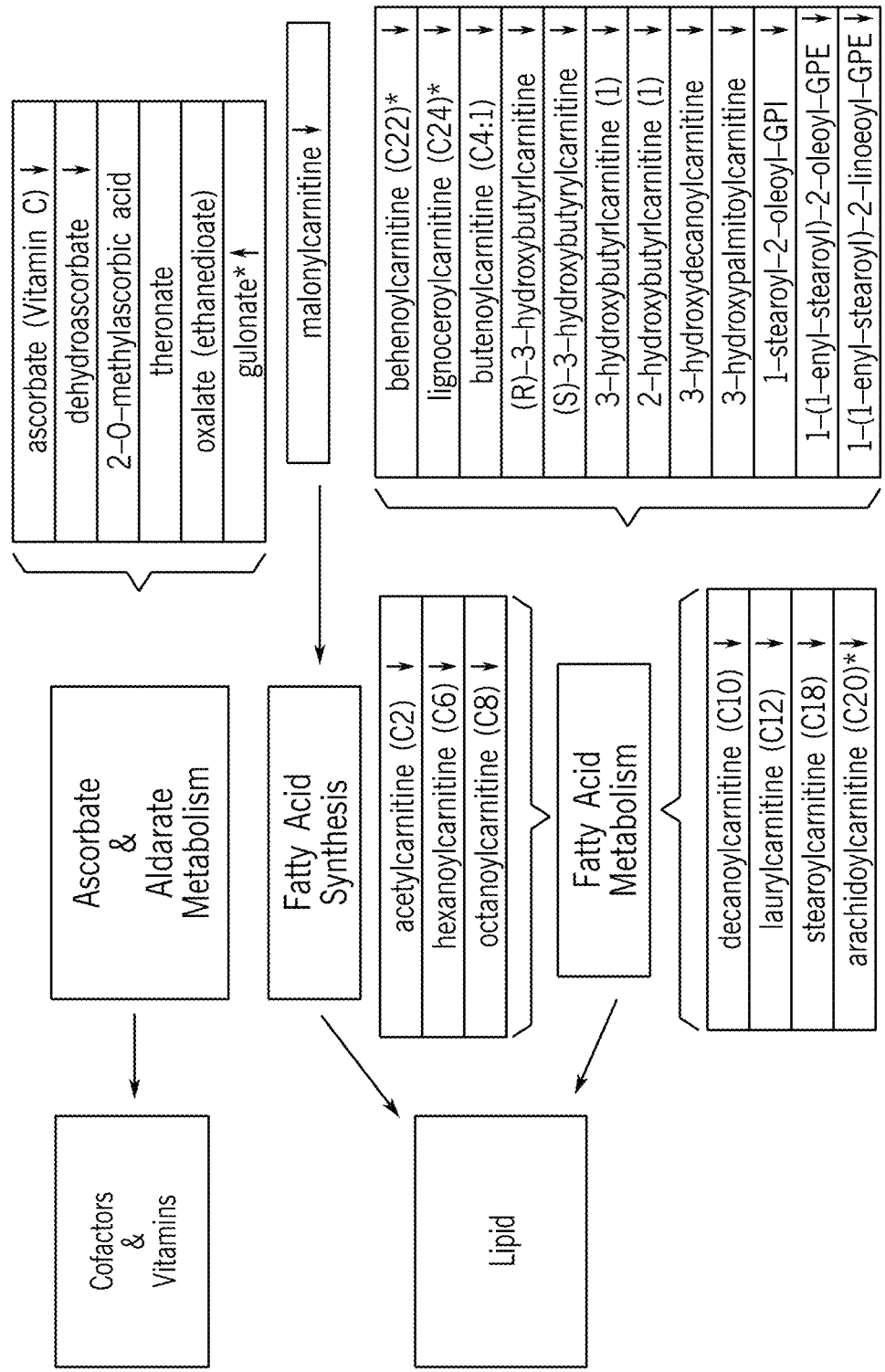

The tumor metabolite changes affected by the EM+M$_4$N+TMZ$_{1/2}$ treatment as compared to treatment with EM+TMZ$_{1/2}$ in the absence of M$_4$N was examined. From a total of 735 metabolites, 160 metabolites showing a fold change greater than 1.20 were selected (FIG. 4). In these results, M$_4$N suppressed most of the metabolic pathways under this treatment schedule, while only five metabolites were increased in the EM+M$_4$N+TMZ$_{1/2}$ treatment significantly when compared to the EM+TMZ$_{1/2}$ treatment. These metabolites are betaine aldehyde, N-acetyl aspartate (NAA), methyl succinate, itaconate, and gulonate (FIG. 5A). These five metabolites are key metabolites related to the suppression of the major reprogrammed metabolic pathways of the tumor including those affecting the TCA cycle, fatty acid synthesis, and fatty acid metabolism. Syntheses of the metabolic enzymes for the progression of these pathways likely can be controlled by the specific immunoglobulins produced through host acquired immunity (FIG. 6).

Example 5

Therapeutic Effects of M$_4$N/TMZ Combined Treatments In Vivo

BALB/c nu mice were inoculated subcutaneously with 1×10$^7$ GFP-labeled LN229 in 100 μL PBS. When the average tumor mass reached 200-300 mm$^3$, tumor bearing mice were randomly divided into four groups. Animals were treated with 150 mg/kg of M$_4$N or/and 5 mg/kg of TMZ by daily oral administration for 35 days. In another set of experiments, BALB/c nu mice were treated with 150 mg/kg of M$_4$N or/and 2.5 mg/kg of TMZ (half dose of TMZ) by daily oral administration and then stop treatment at day 25. The PBS and EM solvent formulation, Vitamin E TPGS NF with Miglyol 812 N, were used as control and solvent control. Tumor measurements will be recorded once a week using a Xenogen IVIS image system (Xenogen, Alameda, CA). Individual mouse weight was measured weekly. (FIG. 7A) Tumor volumes in LN229 xenograft mice (n=5/group) treated with M$_4$N/EM or/and TMZ/EM by daily oral administration for 35 days. The antigen recognition ability by the M$_4$N/TMZ/EM induced endogenous antibodies were analyzed. (FIG. 7B) Co-immunoprecipitation of proteins from whole cell extracts of LN229 cells using antiserum from M$_4$N/TMZ/EM-treated LN229 xenograft mouse #23. The co-immunoprecipitated antigens were analyzed by 10% and 14% SDS polyacrylamide gel electrophoresis. These proteins were further identified by mass spectrometry, as the tumor associated antigens of LN229 cells that were recognized by the sera from M$_4$N/TMZ/EM treated mouse #23. (FIG. 7C) Combined antisera from another three M$_4$N/TMZ/EM-treated mice 4-1, 4-2 and 4-3 also were used to probe western blots of whole proteins of extracted from LN229 cells. FIG. 7B and FIG. 7C showed over ten similar molecules weight proteins that were displayed on these SDS-PAGEs. (FIG. 7D) In a separate study, LN229 xenograft mice (n=5/group) treated with M$_4$N/EM or/and half dose of TMZ/EM by daily oral administration and treatment stopped at day 25 (red arrow). The tumor volumes of TMZ/EM, M$_4$N/TMZ/EM, TMZ$_{1/2}$/EM and M$_4$N/TMZ$_{1/2}$/EM were significantly different compared to EM group after day 23. *: p<0.05, compared to the TMZ$_{1/2}$/EM group. (FIG. 7E) Tumor volumes in LN229 xenograft mice (n=5/group) treated with i.v. injections of antisera from each drug treated group at week 0 and 2. Total radiant efficiency from nude mice at different time points were measured. *: p<0.05, compared to the M$_4$N/EM group; #: p<0.05, compared to M$_4$N/TMZ/EM group; $: p<0.05, compared to M$_4$N/TMZ$_{1/2}$/EM group. Binding activity of antisera to LN229 tumor tissues collected from LN299 tumor xenograft mice without any treatment. (FIG. 7F) Binding activity of antisera to LN229 tumor tissues collected from LN299 tumor xenograft mice without any treatment. (FIG. 7G) Table showing proteins identified by mass spectrometry, as the tumor associated antigens of LN229 cells that were recognized by the sera from M$_4$N/TMZ/EM treated mouse #23.

FIG. 8 shows how binding the tumor related antigens to the serum antibodies at the plasma membranes following EM/TMA/M$_4$N treatment, there is no entrance of these proteins to cytoplasm for many different metabolic pathways. As a result, tumor metabolisms are greatly inactivated.

FIG. 9A. FIG. 9B, FIG. 9C, and FIG. 9D show inhibition of the immune suppressive protein PD-L1 and lowering the serum level of two immunosuppressive cytokines G-CSF and IL 10 in TMZ treated mice. Overall, this approach offers a way, in addition to activating humoral immunity, to also block Ln229 tumor growth. It also stops the "tumor defense" by the inhibition of immunosuppressive PD-L1, IL-10, and G-CSFα.

Example 6

In the present Kras-driven lung cancer model, since mice carry homozygous mutant Kras are embryonic lethal, all Kras mice bred are heterozygous Kras$^{+/G12D}$ that one genetic engineering allele can synthesize the Kras G12D protein by "hit-and-run" recombination and cause cancers spontaneously (FIG. 11A). According to previous reports and experience, lung lesions could be found in mice as young as one-week old. In this group of mice, 100% of the mice will develop lung cancer between 15 to 40 weeks of age (FIG. 11B), and about 30% may also develop thymic lymphoma and papilloma (Nature; 410:6832; 1111-6, 2001). As shown in FIG. 11C, either multiple tumors can be seen on lung surface (left) or tumor cells infiltrate into whole lung (right) at the late stage that causes mice to have breathing problem and die around 200 to 300 days old. The thymic lymphoma occurs much earlier and develops more quickly than lung cancer, the results are large thymic tumor masses that will compress the heart and may also cause lung metastasis; this may result in the mice dying at less than 25 weeks old (FIG. 12 and FIG. 15).

In this study, 10-week old, female, Kras G12D mice were chosen; which lung cancer had not been well developed in at this age. For the treatment with M$_4$N (6.06 mg per mouse) dissolved in EM formulation (Vit. E TPGS plus Miglyol 812N) and given by oral administration daily (FIG. 12A). After consecutive treatments for 120 days, treatment for mice that reached 28 weeks old was stopped in both groups and the mice were monitored and weighed continuously. During treatment, no dramatic weight loss appeared for either group of mice; however, the weight increased consistently after stopping treatment. This observation was attributed to the mice growing, but not due to a tumor mass increase, and the mice activity did not appear to be affected as well as previous reports (FIG. 12B). During this study, two mice lost weight and became moribund quickly; so the mice were sacrificed before they died. One was an EM treated mouse that died at day 53 (18 weeks old) and the other one was an EM+M$_4$N treated mouse that died at day 149 (29 days after treatment stopped, 32 weeks old), both mice had developed thymic lymphoma (FIG. 15).

To examine whether there was lung tumor progression after treatment with EM+M$_4$N, two mice were selected from each group and subjected to MRI scans at age 35 weeks old. As shown in FIG. 13, at least three lung tumors (size ≥1 mm) were found in the EM treated mouse, but none were detected in the EM+M$_4$N treated one. The 42 weeks old, non-treated Kras G12D mouse was used as positive control because both its right and left lungs become white under imaging, indicating the inflammation might have occurred or that tumor cells might have spread out into the entire lung, which was the case with other mice at a similar age (FIG. 11C—right). As was found in brain tumors, when M$_4$N is combined with temozolomide (TMZ) and dissolved in EM formulation for the treatment of glioblastoma, the treatment triggered B cell infiltration around tumors and increased the concentration of immunoglobulins in serum. Thus, without wishing to be bound to any one particular theory, it is thought that M$_4$N could be an immunomodulator for cancer therapy. To verify if M$_4$N had similar effects in the mice that was observed by MRI in FIG. 13, serum samples were taken from the EM treated mice and the EM+M$_4$N treated mice to determine if endogenous immunoglobulin levels by ELISA could be detected the same day after imaging.

Using ELISA for analysis, results indicate that EM+M$_4$N treatment increased serum levels of immunoglobulin (IgM, IgA, IgG1, IgG2a, IgG2b and IgG3) compared to EM treatment and non-treatment controls, indicating that even when M$_4$N treatment was stopped for more than one month, the immunoglobulins triggered by M4N can be produced and maintained continuously. The data for the Kras+/G12D mouse model showed that there were no significant differences in the amount of immunoglobulins detected in the serum of the untreated mouse (32 weeks) model compared to the mouse model that was treated with the EM formulation (35 weeks) solvent alone. The Kras+/G12D mouse model that was treated with M$_4$N, however, dissolved in the EM formulation (35 weeks) showed a noticeable increase in all immunoglobulins compared to both the untreated mouse and the mouse that was only treated with the EM formulation (FIG. 14). Previous research in mouse models has shown that inflammation can increase the likelihood for the growth and progression of lesions in KRAS-mutant mice (Cancer Res; 78:1; 7-14, 2018).

Many studies have been conducted to show that immunoglobulins have anti-inflammatory and pro-inflammatory abilities; however in this study it appears that the immunoglobulins may be functioning in an anti-inflammatory capacity based on the fewer lesions present in the Kras+/G12D mouse model that was treated with $M_4N$ dissolved in the EM formulation compared to the other mouse models in our study (FIG. 13).

It was confirmed that the two mice with thymic lymphoma that were previously discussed (FIG. 12), the cause of their moribund was due to tumors developed from the thymus; which compressed the heart and occupied the thoracic cavity. Tumors, however, did not spread out to the whole lung (FIG. 15A and FIG. 15C). As shown in FIG. 15B, the size and weight of thymic lymphoma increased significantly compared to the thymuses either from wildtype or lung cancer only mice. Due to thymic lymphoma progressing faster than lung cancer, the mice usually died at around 25 weeks old before lung tumors were well developed. During this study, it was observed that one mouse treated with EM+$M_4N$ developed lethal thymic lymphoma, but did not die until it was 32 weeks old compared to an EM treated mouse that died at 18 weeks old. It also was found the EM+$M_4N$ treated mouse had fewer lung tumors compared to the untreated Kras G12D mouse at same age (FIG. 15C). Further research needs to be done to investigate whether higher doses of $M_4N$ can slow down or even prevent both thymic lymphoma and lung cancer progression simultaneously.

While not being bound to any particular theory, according to the results so far, it was found that $M_4N$ can trigger various immunoglobulins synthesis in primary lung tumor mouse models, even after treatment stops. Additional studies are needed to verify if $M_4N$ can improve the immune cell infiltration to the cancer microenvironment, thus triggering antibody production. During treatment, no significant weight loss was found, except for the two mice that developed thymic lymphoma. The weight in those two mice dropped dramatically before they became moribund, indicating the safety of long-term treatment of $M_4N$. Based on our current study in glioblastoma, $M_4N$ not only can modulate immune response but can also alter metabolism in tumor xenografts. By considering the reports that Kras mutation induces metabolic re-programming in lung cancer, and how $M_4N$ plays a role in targeting cancer metabolism here is unknown, the metabolite analysis between two treatment groups is ongoing. Further studies will help to clarify the pharmacologic mechanism of $M_4N$.

Currently, MRI is being used to trace the lung cancer development in each group continuously. Once the mice become moribund or when their age reaches 40 weeks old, the mice will be sacrificed for pathologic analysis to see if lung tumor tissue or immune cell infiltration would have changed under $M_4N$ treatment. While xenograft experiments are the usual method of study, this research is using primary tumor mouse models to test $M_4N$'s therapeutic effect and the length of time for the animal study is longer than any other experiments that have been previously done. For this experiment the start time for treatment was at an early stage of tumorigenesis because it was desired to establish the therapeutic strategy using $M_4N$ at an earlier time point to prevent cancer formation in this mouse model. These results will benefit us as the potential of immunotherapeutic and the preventive role of $M_4N$ treatment from cancer initiation to progression in both preclinical and clinical cancer trials is continued to be studied.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±150%, in some embodiments ±20%, in some embodiments ±10%, in some embodiments ±5%, in some embodiments ±10%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Tao S, Wang S, Moghaddam S J, Ooi A, Chapman E, Wong P K, Zhang D D. Oncogenic KRAS confers chemoresistance by upregulating NRF2. Cancer Res. 2014 Dec. 15; 74(24):7430-41.

Ana Galan-Cobo, Piyada Sitthideatphaiboon, Xiao Qu, Alissa Poteete, Marlese A. Pisegna, Pan Tong, Pei-Hsuan Chen, Lindsey K. Boroughs, Mima L. M. Rodriguez, Winter Zhang, Francesco Parlati, Jing Wang, Varsha Gandhi, Ferdinandos Skoulidis, Ralph J. DeBerardinis, John D. Minna and John V. Heymach. LKB1 and KEAP1/NRF2 Pathways Cooperatively Promote Metabolic Reprogramming with Enhanced Glutamine Dependence in KRAS-Mutant Lung Adenocarcinoma. Cancer Res Jul. 1, 2019 (79) (13) 3251-3267.

Pinto R, Petriella D, Lacalamita R, Montrone M, Catino A, Pizzutilo P, Botticella M A, Zito F A, Del Bene G, Zonno A, Tommasi S, De Summa S. KRAS-Driven Lung Adenocarcinoma and B Cell Infiltration: Novel Insights for Immunotherapy. Cancers (Basel). 2019 Aug. 9; 11(8): 1145.

Johnson L, Mercer K, Greenbaum D, Bronson R T, Crowley D, Tuveson D A, Jacks T. Somatic activation of the K-ras oncogene causes early onset lung cancer in mice. Nature. 2001 Apr. 26; 410(6832):1111-6.

Hanahan D, Weinberg R A. Hallmarks of cancer: the next generation. Cell. 2011 Mar. 4; 144(5):646-74.

Patricia Dias Carvalho, Carlos F. Guimaraes, Ana P. Cardoso, Susana Mendonga, Ângela M Costa, Maria J. Oliveira and Sérgia Velho. KRAS Oncogenic Signaling Extends beyond Cancer Cells to Orchestrate the Microenvironment. Cancer Res Jan. 1, 2018 (78) (1) 7-14.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a glioblastoma or lung cancer in a subject in need thereof, the method comprising administering to the subject an effective amount of a composition comprising

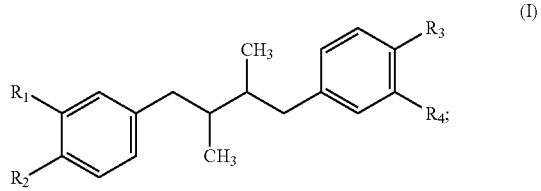

(I)

tetra-o-methyl nordihydroguaiaretic acid (M4N) and an effective amount of temozolomide (TMZ), wherein the composition is dissolved or suspended in a formulation comprising a medium chain triglyceride and D-α-tocopheryl polyethylene glycol succinate (Vitamin E TPGS) to treat the glioblastoma or the lung cancer.

2. The method of claim 1, wherein the amount of temozolomide in the composition is between about 50 mg/m$^2$ to about 200 mg/m$^2$.

3. The method of claim 1, wherein the dosage of $M_4N$ is between about 0.1 mg/kg to about 10 mg/kg.

4. The method of claim 1, wherein the concentration of $M_4N$ is between about 0.01 μM to about 50 μM.

5. The method of claim 1, wherein the dosage of $M_4N$ is selected from a dosage between about 100 mg/kg to about 1000 mg/kg and between about 300 mg/kg to about 600 mg/kg.

6. The method of claim 1, wherein the composition is administered orally.

7. A method for treating a KRAS+/G12D lung cancer in a subject in need thereof, the method comprising administering to the subject having a KRAS+/G12D lung cancer an effective amount of a composition comprising
tetra-o-methyl nordihydroguaiaretic acid (M4N) and an effective amount of temozolomide (TMZ), wherein the composition is dissolved or suspended in a formulation comprising a medium chain triglyceride and D-α-tocopheryl polyethylene glycol succinate (Vitamin E TPGS) to treat lung cancer.

8. The method of claim 7, wherein the amount of temozolomide in the composition is between about 50 mg/m$^2$ to about 200 mg/m$_2$ and the wherein the dosage of MAN is between about 0.1 mg/kg to about 10 mg/kg.

9. The method of claim 7, wherein the composition is administered orally.

10. The method of claim 7, wherein the dosage of $M_4N$ is selected from a dosage between about 100 mg/kg to about 1000 mg/kg and between about 300 mg/kg to about 600 mg/kg.

11. A method for treating a glioblastoma in a subject in need thereof, the method comprising orally administering to the subject in need thereof an effective amount of a composition comprising
tetra-o-methyl nordihydroguaiaretic acid (M4N) and an effective amount of temozolomide (TMZ), wherein the composition is dissolved or suspended in a formulation comprising a medium chain triglyceride and D-α-tocopheryl polyethylene glycol succinate (Vitamin E TPGS) to treat the glioblastoma.

12. The method of claim 11, wherein the amount of temozolomide in the composition is between about 50 mg/m$^2$ to about 200 mg/m$^2$ and the wherein the dosage of $M_4N$ is between about 0.1 mg/kg to about 10 mg/kg.

13. The method of claim 11, wherein the dosage of the $M_4N$ is selected from a dosage between about 100 mg/kg to about 1000 mg/kg and between about 300 mg/kg to about 600 mg/kg.

14. The method of claim 1, wherein administration of the composition increases expression of IL-21 in one or more tissues of the subject.

15. The method of claim 1, wherein administration of the composition increases B cell proliferation and differentiation in one or more tissues of the subject.

16. The method of claim 1, wherein administration of the composition increases secretion of anti-tumor immunoglobulins in one or more tissues of the subject.

17. The method of claim 1, wherein the anti-tumor immunoglobulins are IgA and IgG2a subtypes.

18. The method of claim 1, wherein administration of the composition suppresses one or more major reprogrammed metabolic pathways of a tumor in a subject including major reprogrammed metabolic pathways affecting the TCA cycle, fatty acid synthesis, and fatty acid metabolism.

19. The method of claim 18, wherein the one or more major reprogrammed metabolic pathways of a tumor is selected from a major reprogrammed metabolic pathway affecting the TCA cycle, fatty acid synthesis, and fatty acid metabolism.

20. The method of claim 1, wherein the lung cancer is a KRAS+ lung cancer.

21. The method of claim 1, wherein the lung cancer is a KRAS+ lung cancer.

* * * * *